US011555189B2

(12) United States Patent
Schnell et al.

(10) Patent No.: US 11,555,189 B2
(45) Date of Patent: Jan. 17, 2023

(54) ANTISENSE OLIGOMER COMPOUNDS

(71) Applicant: SAREPTA THERAPEUTICS, INC., Cambridge, MA (US)

(72) Inventors: Frederick J. Schnell, Corvallis, OR (US); Baozhong Cai, Cambridge, MA (US); Jason Gatlin, Cambridge, MA (US); Patrick L. Iversen, Grand Junction, CO (US)

(73) Assignee: SAREPTA THERAPEUTICS, INC., Cambridge, MA (US)

( * ) Notice: Subject to any disclaimer, the term of this patent is extended or adjusted under 35 U.S.C. 154(b) by 75 days.

(21) Appl. No.: 16/754,805

(22) PCT Filed: Oct. 18, 2018

(86) PCT No.: PCT/US2018/056572
§ 371 (c)(1),
(2) Date: Apr. 9, 2020

(87) PCT Pub. No.: WO2019/079637
PCT Pub. Date: Apr. 25, 2019

(65) Prior Publication Data
US 2021/0130822 A1 May 6, 2021

Related U.S. Application Data

(60) Provisional application No. 62/573,985, filed on Oct. 18, 2017.

(51) Int. Cl.
*C12N 15/113* (2010.01)

(52) U.S. Cl.
CPC .... *C12N 15/113* (2013.01); *C12N 2310/3513* (2013.01)

(58) Field of Classification Search
None
See application file for complete search history.

(56) References Cited

U.S. PATENT DOCUMENTS

| | | |
|---|---|---|
| 4,426,330 A | 1/1984 | Sears |
| 4,534,899 A | 8/1985 | Sears |
| 5,013,556 A | 5/1991 | Woodle et al. |
| 5,034,506 A | 7/1991 | Summerton et al. |
| 5,108,921 A | 4/1992 | Low et al. |
| 5,142,047 A | 8/1992 | Summerton et al. |
| 5,166,315 A | 11/1992 | Summerton et al. |
| 5,185,444 A | 2/1993 | Summerton et al. |
| 5,213,804 A | 5/1993 | Martin et al. |
| 5,217,866 A | 6/1993 | Summerton et al. |
| 5,227,170 A | 7/1993 | Sullivan |
| 5,264,221 A | 11/1993 | Tagawa et al. |
| 5,354,844 A | 10/1994 | Beug et al. |
| 5,356,633 A | 10/1994 | Woodle et al. |
| 5,395,619 A | 3/1995 | Zalipsky et al. |
| 5,416,016 A | 5/1995 | Low et al. |
| 5,417,978 A | 5/1995 | Tari et al. |
| 5,459,127 A | 10/1995 | Felgner et al. |
| 5,462,854 A | 10/1995 | Coassin et al. |
| 5,469,854 A | 11/1995 | Unger et al. |
| 5,506,337 A | 4/1996 | Summerton et al. |
| 5,512,295 A | 4/1996 | Kornberg et al. |
| 5,521,063 A | 5/1996 | Summerton et al. |
| 5,521,291 A | 5/1996 | Curiel et al. |
| 5,527,528 A | 6/1996 | Allen et al. |
| 5,534,259 A | 7/1996 | Zalipsky et al. |
| 5,539,082 A | 7/1996 | Nielsen et al. |
| 5,543,152 A | 8/1996 | Webb et al. |
| 5,543,158 A | 8/1996 | Gref et al. |
| 5,547,932 A | 8/1996 | Curiel et al. |
| 5,556,948 A | 9/1996 | Tagawa et al. |
| 5,580,575 A | 12/1996 | Unger et al. |
| 5,583,020 A | 12/1996 | Sullivan |
| 5,591,721 A | 1/1997 | Agrawal et al. |
| 5,595,756 A | 1/1997 | Bally et al. |
| 5,698,685 A | 12/1997 | Summerton et al. |
| 5,714,331 A | 2/1998 | Buchardt et al. |
| 5,719,262 A | 2/1998 | Buchardt et al. |
| 5,770,713 A | 6/1998 | Imbach et al. |
| 6,245,747 B1 | 6/2001 | Porter et al. |
| 6,287,860 B1 | 9/2001 | Monia et al. |

(Continued)

FOREIGN PATENT DOCUMENTS

| | | |
|---|---|---|
| WO | WO-9301286 A2 | 1/1993 |
| WO | WO-9324510 A1 | 12/1993 |

(Continued)

OTHER PUBLICATIONS

Osman, Erkan Y et al. ("Bifunctional RNAs targeting the intronic splicing silencer N1 increase SMN levels and reduce disease severity in an animal model of spinal muscular atrophy." Molecular Therapy 20.1 (2012): 119-126).*

(Continued)

*Primary Examiner* — Kimberly Chong

(74) *Attorney, Agent, or Firm* — Sterne, Kessler, Goldstein & Fox P.L.L.C.

(57) ABSTRACT

A modified antisense oligonucleotide of about 10 to about 40 nucleobases is disclosed. The oligonucleotide comprises a targeting sequence having a region complementary to at least one string of three or more identical contiguous nucleobases in a target sequence, wherein the target sequence comprises at least one additional nucleobase compared to the region of the targeting sequence and the at least one additional nucleobase has no complementary nucleobase in the region of the targeting sequence, and wherein the targeting region complementary to the at least one string of three or more identical contiguous nucleobases is internal to the targeting sequence.

9 Claims, 7 Drawing Sheets

Specification includes a Sequence Listing.

(56) References Cited

U.S. PATENT DOCUMENTS

| | | |
|---|---|---|
| 6,670,461 B1 | 12/2003 | Wengel et al. |
| 6,747,014 B2 | 6/2004 | Teng et al. |
| 6,794,499 B2 | 9/2004 | Wengel et al. |
| 6,887,906 B1 | 5/2005 | Teng |
| 6,965,025 B2 | 11/2005 | Gaarde et al. |
| 6,969,400 B2 | 11/2005 | Rhee et al. |
| 6,969,766 B2 | 11/2005 | Kim et al. |
| 7,022,851 B2 | 4/2006 | Kim et al. |
| 7,034,133 B2 | 4/2006 | Wengel et al. |
| 7,053,207 B2 | 5/2006 | Wengel |
| 7,060,809 B2 | 6/2006 | Wengel et al. |
| 7,084,125 B2 | 8/2006 | Wengel |
| 7,125,994 B2 | 10/2006 | Kim et al. |
| 7,145,006 B2 | 12/2006 | Kim et al. |
| 7,179,896 B2 | 2/2007 | Kim et al. |
| 7,211,668 B2 | 5/2007 | Kim et al. |
| 7,569,575 B2 | 8/2009 | Sorensen et al. |
| 7,572,582 B2 | 8/2009 | Wengel et al. |
| 7,838,657 B2 | 11/2010 | Singh et al. |
| 7,935,816 B2 | 5/2011 | Li |
| 7,943,762 B2 | 5/2011 | Weller et al. |
| 8,076,476 B2 | 12/2011 | Reeves et al. |
| 8,299,206 B2 | 10/2012 | Fox et al. |
| 10,179,912 B2 | 1/2019 | De Visser et al. |
| 2003/0027780 A1 | 2/2003 | Hardee et al. |
| 2003/0045488 A1 | 3/2003 | Brown et al. |
| 2005/0288246 A1 | 12/2005 | Iversen et al. |
| 2010/0016215 A1 | 1/2010 | Moulton et al. |
| 2011/0269820 A1 | 11/2011 | Singh et al. |

FOREIGN PATENT DOCUMENTS

| | | |
|---|---|---|
| WO | WO-9426764 A1 | 11/1994 |
| WO | WO-2004043977 A2 | 5/2004 |
| WO | WO-2006000057 A1 | 1/2006 |
| WO | WO-2007002390 A2 | 1/2007 |
| WO | WO-2008036127 A2 | 3/2008 |
| WO | WO-2009008725 A2 | 1/2009 |
| WO | WO-2009064471 A1 | 5/2009 |
| WO | WO-2010064146 A2 | 6/2010 |
| WO | WO-2010115993 A1 | 10/2010 |
| WO | WO-2010120820 A1 | 10/2010 |
| WO | WO-2010148249 A1 | 12/2010 |
| WO | WO-2011005761 A1 | 1/2011 |
| WO | WO-2011034072 A1 | 3/2011 |
| WO | WO-2011150408 A2 | 12/2011 |
| WO | WO-2012039448 A1 | 3/2012 |
| WO | WO-2012043730 A1 | 4/2012 |
| WO | WO-2012150960 A1 | 11/2012 |
| WO | WO-2013012758 A1 | 1/2013 |
| WO | WO-2013053928 A1 | 4/2013 |
| WO | WO-2013074834 A1 | 5/2013 |
| WO | WO-2013086207 A1 | 6/2013 |
| WO | WO-2013112053 A1 | 8/2013 |
| WO | WO-2014010250 A1 | 1/2014 |
| WO | WO-2014012081 A2 | 1/2014 |
| WO | WO-2014153220 A2 | 9/2014 |
| WO | WO-2015107425 A2 | 7/2015 |
| WO | WO-2015108046 A1 | 7/2015 |
| WO | WO-2015108047 A1 | 7/2015 |
| WO | WO-2015108048 A1 | 7/2015 |
| WO | WO-2017040271 A1 | 3/2017 |
| WO | WO-2017184529 A1 | 10/2017 |

OTHER PUBLICATIONS

Yin et al. ("Cell-penetrating peptide-conjugated antisense oligonucleotides restore systemic muscle and cardiac dystrophin expression and function." Human molecular genetics 17.24 (2008): 3909-3918).*

Altschul, Stephen F., et al., "Gapped BLAST and PSI-BLAST: a new generation of protein database search programs," Nucleic acids research 25(17): 3389-3402, Oxford Academic, England (1997).

Benner, S.A. and Sismour, A.M., "Synthetic Biology," Nature Reviews. Genetics 6(7):553-543, Nature Pub. Group, England (2005).

Brand, Rhonda M., et al., "Transdermal delivery of antisense oligonucleotides can induce changes in gene expression in vivo," Antisense and Nucleic Acid Drug Development 11(1): 1-6, Mary Ann Liebert Publishing, United States (2001).

Chiu, Y.L. and Rana, T.M., "SiRNA Function in RNAi: A Chemical Modification Analysis," RNA 9(9): 1034-1048, Cold Spring Harbor Laboratory Press, United States (2003).

Deruisseau, Lara R., et al., "Neural deficits contribute to respiratory insufficiency in Pompe disease," Proceedings of the National Academy of Sciences 106(23): 9419-9424, National Academy of Sciences, United States (2009).

Devereux, John, Paul Haeberli, and Oliver Smithies, "A comprehensive set of sequence analysis programs for the VAX," Nucleic acids research 12(1Part1): 387-395, IRL Press Limited, England (1984).

Devi, Gayathri R., et al., "Inhibition of human chorionic gonadotropin β-subunit modulates the mitogenic effect of c-myc in human prostate cancer cells," The Prostate 53(3): 200-210, John Wiley and Sons, United States (2002).

Dokka, Sujatha, and Yon Rojanasakul, "Novel non-endocytic delivery of antisense oligonucleotides," Advanced drug delivery reviews 44(1): 35-49, Elsevier, Netherlands (2000).

Egholm, M., et al., "PNA Hybridizes to Complementary Oligonucleotides Obeying the Watson-crick Hydrogen-bonding Rules," Nature 365(6446):566-568, Nature Publishing Group, England (Oct. 1993).

Forte, A., et al., "Small interfering RNAs and antisense oligonucleotides for treatment of neurological diseases," Current Drug Targets 6(1): 21-29, Bentham Science Publisher, United Arab Emirates (2005).

Genbank, "Leishmania donovani strain MHOM/IN/1983/AG83 isolate early passage chromosome 4 sequence," Accession No. CP018606.1, accessed at https://www.ncbi.nlm.nih.gov/nuccore/CP018606.1, accessed on Mar. 3, 2021, 91 pages.

Gregoriadis, G., Drug Carriers in Biology and Medicine, Chapter 14, Liposomes, Drug Carriers in Biology and Medicine, pp. 287-341, Academic Press, England, 1979.

Hames et al., Nucleic Acid Hybridization, Chapter 4, IRL Press, England, 1985, pp. 107-108.

Hirao, I., "Unnatural Base Pair Systems for DNA/RNA-based Biotechnology," Current Opinion in Chemical Biology 10(6):622-627, Elsevier, England (2006).

International Search Report and Written Opinion for International Application No. PCT/US2018/056572, International Search Authority, United States, dated May 6, 2019, 12 pages.

Iyer, R.P., et al., "The Automated Synthesis of Sulfur-Containing Oligodeoxyribonucleotides Using 3H-1,2-Benzodithiol-3-one 1,1-Dioxide as a Sulfur-Transfer Reagent," The Journal of Organic Chemistry 55(15):4693-4699, American Chemical Society, United States (1990).

Jaeger, Laura B., and William A. Banks, "Transport of antisense across the blood-brain barrier," Antisense Therapeutics: 237-251, Springer Publishing, United States (2005).

Kool, E.T., "Replacing the Nucleobases in DNA with Designer Molecules," Accounts of Chemical Research 35(11):936-943, American Chemical Society, United States (2002).

Krueger, A.T., et al., "Synthesis and Properties of Size-expanded DNAs: Toward Designed, Functional Genetic Systems," Accounts of Chemical Research 40(2):141-150, American Chemical Society, United States (2007).

Lappalainen, Katriina, et al., "Cationic liposomes mediated delivery of antisense oligonucleotides targeted to HPV 16 E7 mRNA in CaSki cells," Antiviral research 23(2): 119-130, Elsevier, Netherlands (1994).

Limbach, P.A., et al., "Summary: the Modified Nucleosides of RNA," Nucleic Acids Research 22(12):2183-2196, Oxford University Press, England (1994).

Martin, P., "New Access to 2'-O-alkylated Ribonucleosides and Properties of 2'-O-alkylated Oligoribonucleotides," Helvetica Chimica Acta 78(2):486-504, John Wiley & Sons, Switzerland (1995).

(56) References Cited

OTHER PUBLICATIONS

Miyada C. G. and Wallace R. B., Oligomer Hybridization Techniques, Methods Enzymol. vol. 154 pp. 94-107 Academic Press Inc., United States (1987).

Nielsen, P.E., et al., "Sequence-Selective Recognition of DNA by Strand Displacement with a Thymine-Substituted Polyamide," Science 254(5037):1497-1500, American Association for the Advancement of Science, United States (1991).

Obika, S., et al., "Synthesis and Properties of 3'-amino-2',4'-BNA, a Bridged Nucleic Acid with a N3'→P5' Phosphoramidate Linkage," Bioorganic Medicinal Chemistry 16(20):9230-9237, Elsevier Science, England (2008).

Obika, S., et al., "Synthesis of 2'-O,4'-C-methyleneuridine and -cytidine. Novel Bicyclic Nucleosides having a Fixed C3, -endo Sugar Puckering," Tetrahedron Letters 38(50):8735-8738, Elsevier, United Kingdom (1997).

Obika, S., et al., "Stability and Structural Features of the Duplexes Containing Nucleoside Analogues With a Fixed N-type Conformation, 2'-O,4'- C-methyleneribonucleosides ," Tetrahedron Letters 39(1998):5401-5404, Elsevier, United Kingdom (Jul. 1998).

Revankar, G.R. and Rao, T.S., DNA with Altered Bases: in Comprehensive Natural Products Chemistry, vol. 7, pp. 313-339, Elsevier, United Kingdom (1999).

Romesberg, Floyd E. and Henry, Allison A., "Beyond A, C, G and T: augmenting nature's alphabet," Current opinion in chemical biology 7(6): 727-733, Elsevier, Netherlands (2003).

Stein, David A., et al. "Inhibition of Vesivirus infections in mammalian tissue culture with antisense morpholino oligomers." Antisense and Nucleic Acid Drug Development 11(5): 317-325, Mary Ann Liebert Publishing, United States (2001).

Summerton, J. and D. Weller. "Morpholino antisense oligomers: design, preparation, and properties," Antisense Nucleic Acid Drug Dev 7(3): 187-95, Mary Ann Liebert Publishing, United States (1997).

T.W. Greene, P.G.M. Wuts, Protective Groups in Organic Synthesis, Table of Contents, Chapter 1; pp. 1-16, Chapter 7; pp. 503-653, 3rd ed. John Wiley & Sons, United States (1999).

Uhlmann et al., "Antisense oligomers: a new therapeutic principle," Chemical Reviews 90(4): 544-584, The American Chemical Society, United States (1990).

Vanin, Elio F., and Tae H. Ji, "Synthesis and application of cleavable photoactivatable heterobifunctional reagents," Biochemistry 20(24): 6754-6760, American Chemical Society, United States (1981).

Vinogradov, Serguei V., et al., "Nanogels for oligonucleotide delivery to the brain," Bioconjugate chemistry 15(1): 50-60, American Chemical Society, United States (2004).

Wengel, et al., "Synthesis of 3'-C- and 4'-C-Branched Oligodeoxynucleotides and the Development of Locked Nucleic Acid (LNA)," Accounts of Chem. Research 32(4):301-10, American Chemical Society, United States (1999).

Koshkin, Alexei A., et al. "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron 54(14): 3607-3630, Elsevier, United Kingdom (1998).

Singh; S.K., et al., "LNA (locked nucleic acids): synthesis and high-affinity nucleic acid recognition," Chemical Communications 4:455-6, Royal Chemistry Society, England (1998).

Williams, S. A., et al. "Cationic lipids reduce time and dose of c-myc antisense oligodeoxynucleotides required to specifically inhibit Burkitt's lymphoma cell growth." Leukemia 10(12): 1980-1989, Stockton Press, United States (1996).

Wu, George Y., and Catherine H. Wu., "Receptor-mediated in vitro gene transformation by a soluble DNA carrier system," Journal of Biological Chemistry 262(10): 4429-4432, Elsevier, Netherlands (1987).

Yamada, T., et al., "Synthesis of 2'-O-[2-(N-methylcarbamoyl)ethyl]ribonucleosides Using Oxa-michael Reaction and Chemical and Biological Properties of Oligonucleotide Derivatives Incorporating These Modified Ribonucleosides," The Journal of Organic Chemistry 76(9):3042-3053, American Chemical Society, United States (2011).

Yoo, B.H., et al., "2'-O-methyl-modified Phosphorothioate Antisense Oligonucleotides Have Reduced Non-specific Effects in Vitro," Nucleic Acids Research 32(6):2008-2016, Oxford University Press, England (2004).

* cited by examiner

FIG.2

ANTISENSE OLIGOMER COMPOUNDS

REFERENCE TO A SEQUENCE LISTING SUBMITTED ELECTRONICALLY VIA EFS-WEB

The content of the electronically submitted sequence listing in ASCII text file (Name: 4010_0430001_Seq-listing_ST25; Size: 34,337 bytes; and Date of Creation: Feb. 2, 2022) is herein incorporated by reference in its entirety.

CROSS REFERENCE TO RELATED APPLICATION

This application is a U.S. national phase of International Application No. PCT/US2018/056572, filed on Oct. 18, 2018, which claims priority to U.S. Provisional Patent Application No. 62/573,985 filed on Oct. 18, 2017 entitled ANTISENSE OLIGOMER COMPOUNDS, the disclosure of which is incorporated herein by reference.

FIELD OF THE DISCLOSURE

The present disclosure relates to an antisense oligomer compound in which a string of nucleobases present in the oligomer compound is broken by a deletion of at least one nucleobase, and methods of using such compound.

BACKGROUND

Antisense oligomers offer great potential as pharmaceutical drugs, as evidenced by the number of antisense drugs currently in clinical development, and aided by the fact that a number of potential limitations of antisense oligomers have been successfully addressed over the past several years (see, for e.g.: Devi et al., 2002; Antisense Nucleic Acid Drug Dev.; see also, for e.g.: Stein et al., 2001; Antisense Nucleic Acid Drug Dev.). Novel uncharged oligomer backbones have been developed to improve uptake into cells, and to increase resistance to nuclease degradation (see, for e.g.: Iversen et al., 2001; Antisense Drug Technology). For some oligomer structures, for example, morpholino based structures, the modified backbone has been found to give enhanced binding affinity to its target nucleic acid (see, for e.g.: Iversen et al., 2001; Antisense Drug Technology; see also: Summerton et al., 1997; Antisense Nucleic Acid Drug Dev.).

In some antisense applications, the optimal targeting sequence against which the antisense oligomer is directed to may include a biological palindrome sequence or, alternately, a string of three or four or more nucleobases. Surprisingly, it has been found that antisense oligomer compounds directed towards a target sequence having a string of three or more identical contiguous nucleobases, or alternatively a biological palindrome sequence, can compromise the antisense activity of the compound, as well as present difficulties in a manufacturing process.

SUMMARY

In various aspects, modifications to an antisense oligomer compound, having a string of three or four or more nucleobases, or alternatively, a biological palindrome sequence, is provided. In various embodiments, the modification enhances antisense activity of the compound and/or its methods of manufacture, including but not limited to aggregations that can occur during certain methods of manufacture.

In further aspects, a modified antisense oligonucleotide of about 10 to about 40 nucleobases is provided. The subject oligonucleotide comprises a targeting sequence having a region complementary to at least one string of three or more identical contiguous nucleobases in a target sequence, wherein the target sequence comprises at least one additional nucleobase compared to the region of the targeting sequence and the at least one additional nucleobase has no complementary nucleobase in the region of the targeting sequence, and wherein the targeting region complementary to the at least one string of three or more identical contiguous nucleobases is internal to the targeting sequence. In embodiments, the targeting sequence comprises at least one string of three nucleobases. In embodiments, the targeting sequence comprises at least one string of four nucleobases. In embodiments, the at least one string of three or more nucleobases comprises at least one string of three or more guanine bases. In embodiments, the modified antisense oligonucleotide is conjugated to a peptide. In embodiments, the target sequence comprises an exon target associated with Duchenne muscular dystrophy (DMD). In embodiments, the target sequence comprises exon 44 in the processing of human dystrophin pre-processed mRNA. In embodiments, the targeting sequence comprises any one of SEQ ID NOs: 2-7. In embodiments, the target sequence comprises exons 45, 51 or 53 of human dystrophin pre-processed mRNA. In embodiments, the targeting sequence comprises any one of SEQ ID NOs: 72-120. In embodiments, the target sequence comprises an exon target associated with spinal muscular atrophy (SMA). In embodiments, the target sequence comprises a region adjacent to exon 7 in the processing of human SMN2 pre-processed mRNA. In embodiments, the targeting sequence comprises any one of SEQ ID NOs: 9-25. In embodiments, the target sequence comprises an exon target associated with glycogen storage disease type II (GSD-II). In embodiments, the target sequence comprises a region associated with exon 2 of the human acid alpha-glucosidase pre-processed mRNA. In embodiments, the targeting sequence comprises any one of SEQ ID NOs: 26-68

In further aspects, the subject nucleotide comprises a targeting sequence having a region complementary to at least one biological palindrome sequence in a target sequence, wherein the target sequence comprises at least one additional nucleobase has no complementary nucleobase in the region of the targeting sequence, and wherein the targeting region complementary to the at least one biological palindrome sequence is internal to the targeting sequence. In embodiments, the at least one biological palindrome sequence comprises at least five, at least six, or at least seven or more nucleobases. In embodiments, the modified antisense oligonucleotide is conjugated to a peptide. In embodiments, the target sequence comprises an exon target associated with Duchenne muscular dystrophy. In embodiments, the target sequence comprises exon 44 in the processing of human dystrophin pre-processed mRNA. In embodiments, the targeting sequence comprises any one of SEQ ID NOs: 2-7. In embodiments, the target sequence comprises exons 45, 51 or 53 of human dystrophin pre-processed mRNA. In embodiments, the targeting sequence comprises any one of SEQ ID NOs: 72-120. In embodiments, the target sequence comprises an exon target associated with spinal muscular atrophy. In embodiments, the target sequence comprises a region adjacent to exon 7 in the processing of human SMN2 pre-processed mRNA. In embodiments, the targeting sequence comprises any one of SEQ ID NOs: 9-25. In embodiments, the target sequence comprises an exon target associated with glycogen storage disease type II. In embodiments, the target sequence comprises a region associated with exon 2 of the human acid alpha-glucosidase pre-processed mRNA. In embodiments, the targeting sequence comprises any one of SEQ ID NOs: 26-68.

In various aspects and embodiments, the subject oligonucleotide is referred to as a deletion sequence. The deletion sequence comprises any one of SEQ ID NOs: 1-128, wherein at least one nucleobase in any one of SEQ ID NOs: 1-128 has been deleted. In embodiments, the at least one nucleobase that has been deleted is internal to the sequence of any one of SEQ ID NOs: 1-128. In various embodiments, the deletion sequence comprises CTCCAACAT-CAAGGAAGATGGCATTTCTAG (SEQ ID NO: 69; Eteplirsen); GTTGCCTCCGGTTCTGAAGGTGTTC (SEQ ID NO: 70; Golodirsen); or CAATGCCATCCTG-GAGTTCCTG (SEQ ID NO: 71; Casimersen). In various embodiments, the deletion sequence comprises any one of SEQ ID NOs: 69-71, wherein at least one nucleobase in any one of SEQ ID NOs: 69-71 has been deleted. In embodiments, the at least one nucleobase that has been deleted is internal to the sequence of any one of SEQ ID NOs: 69-71.

These and other objects and features of the present disclosure will become more fully apparent when the following detailed description is read in conjunction with the accompanying drawings.

BRIEF DESCRIPTION OF THE FIGURES

FIG. 2 details certain deletion sequences.

DETAILED DESCRIPTION

I. Definitions and Interpretation

Figure 1:
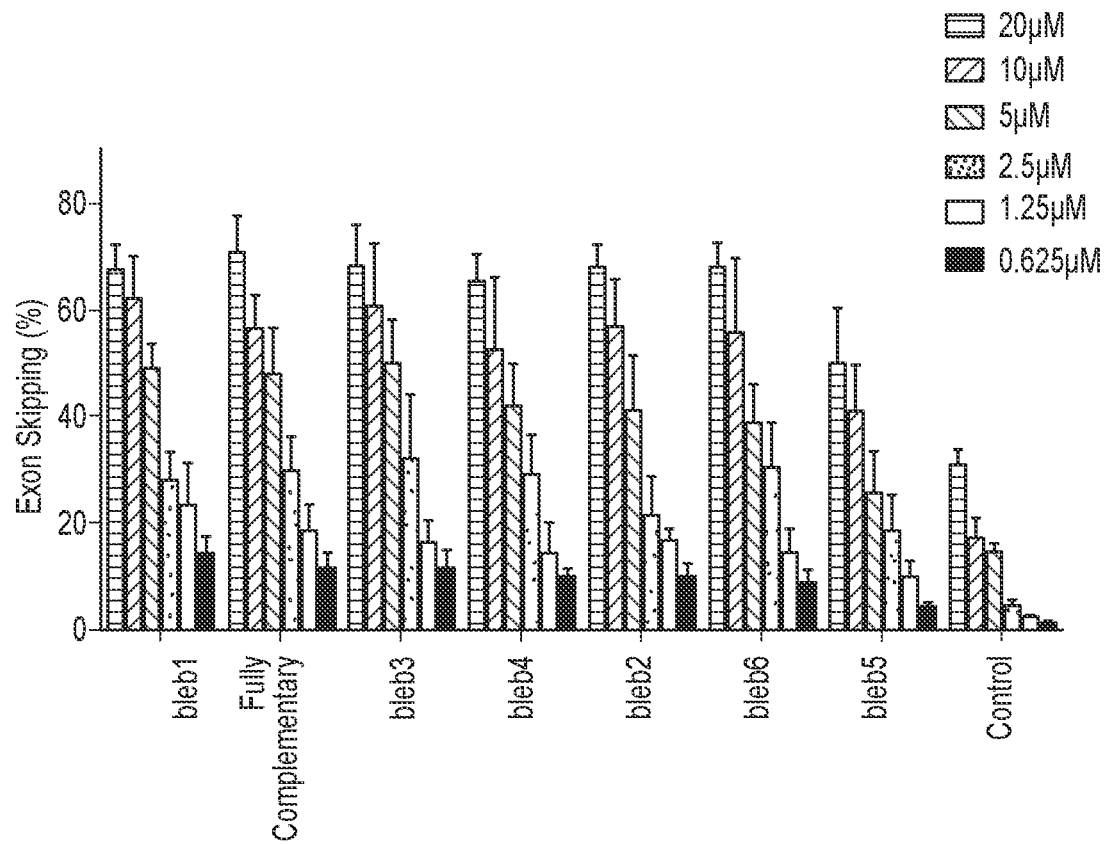
FIG. 1 details exon skipping percentages for deletion sequences directed against exon 44.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the subject matter of the present disclosure, preferred methods and materials are described. For the purposes of the present disclosure, the following terms are defined below.

As used herein, the articles "a" and "an" are used herein to refer to one or to more than one (i.e., to at least one) of the grammatical object of the article. By way of example, "an element" means one element or more than one element.

As used herein, "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level; value, number, frequency, percentage, dimension, size, amount, weight or length.

As used herein, unless the context requires otherwise, the words "comprise," "comprises," and "comprising" will be understood to imply the inclusion of a stated step or element or group of steps or elements but not the exclusion of any other step or element or group of steps or elements.

As used herein, "consisting of" is meant including, and limited to, whatever follows the phrase "consisting of:" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

As used herein, an "antisense oligonucleotide," "antisense oligomer" or "oligonucleotide" refers to a linear sequence of nucleotides, or nucleotide analogs, which allows the nucleobase to hybridize to a target sequence in an RNA by Watson-Crick base pairing, to form an oligomer RNA heteroduplex within the target sequence. The terms "antisense oligonucleotide", "modified antisense oligonucleotide", "antisense oligomer", "oligomer" and "compound" may be used interchangeably to refer to an oligomer. The cyclic subunits may be based on ribose or another pentose sugar or, in certain embodiments, a morpholino group (see description of morpholino oligomers herein). Also contemplated are peptide nucleic acids (PNAs), locked nucleic acids (LNAs), tricyclo-DNA oligomers, tricyclo-phosphorothioate oligomers, and 2'-O-Methyl oligomers, among other antisense agents known in the art. Included are non-naturally-occurring oligomers, or "oligonucleotide analogs," including oligomers having (i) a modified backbone structure, e.g., a backbone other than the standard phosphodiester linkage found in naturally-occurring oligo- and polynucleotides, and/or (ii) modified sugar moieties, e.g., morpholino moieties rather than ribose or deoxyribose moieties. Oligomer analogs support bases capable of hydrogen bonding by Watson-Crick base pairing to standard polynucleotide bases, where the analog backbone presents the bases in a manner to permit such hydrogen bonding in a sequence-specific fashion between the oligomer analog molecule and bases in a standard polynucleotide (e.g., single-stranded RNA or single-stranded DNA). Preferred analogs are those having a substantially uncharged, phosphorus containing backbone.

As used herein, a "nuclease-resistant" oligomer refers to one whose backbone is substantially resistant to nuclease cleavage, in non-hybridized or hybridized form; by common extracellular and intracellular nucleases in the body (for example, by exonucleases such as 3'-exonucleases, endonucleases, RNase H); that is, the oligomer shows little or no nuclease cleavage under normal nuclease conditions in the body to which the oligomer is exposed. A "nuclease-resistant heteroduplex" refers to a heteroduplex formed by the binding of an antisense oligomer to its complementary target, such that the heteroduplex is substantially resistant to in vivo degradation by intracellular and extracellular nucleases, which are capable of cutting double-stranded RNA/RNA or RNA/DNA complexes. A "heteroduplex" refers to a duplex between an antisense oligomer and the complementary portion of a target RNA.

As used herein, "coding sequence" means any nucleic acid sequence that contributes to the code for the polypeptide product of a gene. By contrast, the term "non-coding sequence" refers to any nucleic acid sequence that does not directly contribute to the code for the polypeptide product of a gene.

As used herein, the terms "contacting a cell", "introducing" or "delivering" include delivery of the oligomers of the disclosure into a cell by methods routine in the art, e.g., transfection (e.g., liposome, calcium-phosphate, polyethyleneimine), electroporation (e.g., nucleofection), microinjection.

As used herein, the term "alkyl" is intended to include linear (i.e., unbranched or acyclic), branched, cyclic, or polycyclic non-aromatic hydrocarbon groups, which are optionally substituted with one or more functional groups. Unless otherwise specified, "alkyl" groups contain one to eight, and preferably one to six carbon atoms. C1-C6 alkyl, is intended to include C1, C2, C3, C4, C5, and C6 alkyl groups. Lower alkyl refers to alkyl groups containing 1 to 6 carbon atoms. Examples of Alkyl include, but are not limited to, methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, etc. Alkyl may be substituted or unsubstituted. Illustrative substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl, phenethyl, substituted phenethyl, etc.

As used herein, "alkenyl" refers to an unsaturated monovalent radical containing carbon and hydrogen, which may be branched, linear, or cyclic. The alkenyl group may be monounsaturated or polyunsaturated. Generally preferred are alkenyl groups having one to six carbon atoms, referred to as "lower alkenyl".

As used herein, the term "alkoxy" means a subset of alkyl in which an alkyl group as defined above with the indicated number of carbons attached through an oxygen bridge. For example, "alkoxy" refers to groups —O-alkyl, wherein the alkyl group contains 1 to 8 carbons atoms of a linear, branched, cyclic configuration. Examples of "alkoxy" include, but are not limited to, methoxy, ethoxy, n-propoxy, i-propoxy, t-butoxy, n-butoxy, s-pentoxy and the like.

As used herein, the term "aryl" used alone or as part of a larger moiety as in "aralkyl", "aralkoxy", or "aryloxyalkyl", refers to aromatic ring groups having six to fourteen ring atoms, such as phenyl, 1-naphthyl, 2-naphthyl, 1-anthracyl and 2-anthracyl. An "aryl" ring may contain one or more substituents. The term "aryl" may be used interchangeably with the term "aryl ring". "Aryl" also includes fused polycyclic aromatic ring systems in which an aromatic ring is fused to one or more rings. Non-limiting examples of useful aryl ring groups include phenyl, hydroxyphenyl, halophenyl, alkoxyphenyl, dialkoxyphenyl, trialkoxyphenyl, alkylenedioxyphenyl, naphthyl, phenanthryl, anthryl, phenanthro and the like, as well as 1-naphthyl, 2-naphthyl, 1-anthracyl and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring. "Aralkyl" refers to an alkyl, preferably lower (C1-C4, more preferably C1-C2) alkyl, substituent which is further substituted with an aryl group; examples are benzyl (—CH2C6H5) and phenethyl (—CH2CH2C6H5).

As used herein, the term "substituted", with respect to an alkyl, alkenyl, alkynyl, aryl, aralkyl, or alkaryl group, refers to replacement of a hydrogen atom with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic.

As used herein, the term "acyl" means a C(O)R group (in which R signifies H, alkyl or aryl as defined above). Examples of acyl groups include formyl, acetyl, benzoyl, phenylacetyl and similar groups.

As used herein, the term "homolog" means compounds differing regularly by the successive addition of the same chemical group. For example, a homolog of a compound may differ by the addition of one or more —CH2- groups, amino acid residues, nucleotides, or nucleotide analogs.

As used herein, the terms "cell penetrating peptide" (CPP) or "a peptide moiety which enhances cellular uptake" are used interchangeably and refer to cationic cell penetrating peptides, also called "transport peptides", "carrier peptides", or "peptide transduction domains". The peptides, as shown herein, have the capability of inducing cell penetration within about or at least about 30%, 40%, 50%, 60%, 70%, 80%. 90%, or 100% of cells of a given cell culture population and allow macromolecular translocation within multiple tissues in vivo upon systemic administration. In some embodiments, the CPPs are of the formula —[(C(O)CHR'NH)m]R" wherein R' is a side chain of a naturally occurring amino acid or a one- or two-carbon homolog thereof, R" is selected from hydrogen or acyl, and m is an integer up to 50. CPPs may also have the formula —[(C(O)CHR'NH)m]Ra wherein R' is a side chain of a naturally occurring amino acid or a one- or two-carbon homolog thereof, and where Ra is selected from Hydrogen, acyl, benzoyl, or stearoyl. CPPs of any structure may be linked to the 3' or 5' end of an antisense oligomer via a "linker" such as, for example, —C(O)(CH2)5NH—, —C(O)(CH2)2NH—, —C(O)(CH2)2NH—C(O)(CH2)5NH—, or —C(O)CH2NH—. Additional CPPs are well-known in the art and are disclosed, for example, in U.S. Patent Publication No. 2010/0016215, which is incorporated by reference in its entirety. In other embodiments, m is an integer selected from 1 to 50 where, when m is 1, the moiety is a single amino acid or derivative thereof.

As used herein, "amino acid" refers to a compound consisting of a carbon atom to which are attached a primary amino group, a carboxylic acid group, a side chain, and a hydrogen atom. For example, the term "amino acid" includes, but is not limited to, Glycine, Alanine, Valine, Leucine, Isoleucine, Asparagine, Glutamine, Lysine and Arginine. Additionally, as used herein, "amino acid" also includes derivatives of amino acids such as esters, and amides, and salts, as well as other derivatives, including derivatives having pharmacoproperties upon metabolism to an active form. Accordingly, the term "amino acid" is understood to include naturally occurring and non-naturally occurring amino acids.

As used herein, an "electron pair" refers to a valence pair of electrons that are not bonded or shared with other atoms.

As used herein, "homology" refers to the percentage number of amino acids that are identical or constitute conservative substitutions. Homology may be determined using sequence comparison programs such as GAP (see: Deveraux et al., 1984, Nucleic Acids Research 12, 387-395). In this way sequences of a similar or substantially different length to those cited herein could be compared by insertion of gaps into the alignment, such gaps being determined, for example, by the comparison algorithm used by GAP.

As used herein, "isolated" means material that is substantially or essentially free from components that normally accompany it in its native state. For example, an "isolated polynucleotide," "isolated oligonucleotide," or "isolated oligomer" as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

As used herein, the terms "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or more antisense compounds or compositions to produce or cause a greater physiological response (i.e., downstream effects) in a cell or a subject relative to the response caused by either no antisense compound or a control compound. Relevant physiological or cellular responses (in vivo or in vitro) will be apparent to persons skilled in the art. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times), including all integers and decimal points in between and above 1 (e.g., 1.5, 1.6, 1.7, 1.8), the amount produced by no antisense compound (the absence of an agent) or a control compound. The term "reduce" or "inhibit" may relate generally to the ability of one or more antisense compounds or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in the symptoms or pathology of a glycogen storage disease such as Pompe disease, for example, a decrease in the accumulation of glycogen in one or more tissues. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

As used herein, "nucleobase" (Nu), "base pairing moiety" or "base" are used interchangeably to refer to a purine or pyrimidine base found in native DNA or RNA (uracil, thymine, adenine, cytosine, and guanine), as well as analogs of the naturally occurring purines and pyrimidines, that confer improved properties, such as binding affinity to the oligomer. Exemplary analogs include hypoxanthine (the base component of the nucleoside inosine); 2, 6-diaminopurine; 5-methyl cytosine; C5-propynyl-modified pyrimidines; 9-(aminoethoxy)phenoxazine (G-clamp) and the like. Further examples of base pairing moieties include, but are not limited to, uracil, thymine, adenine, cytosine, guanine and hypoxanthine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313, are also contemplated. Further examples of base pairing moieties include, but are not limited to, expanded-size nucleobases in which one or more benzene rings has been added. Nucleic base replacements described in the Glen Research catalog (www.glenresearch.com); Krueger A T et al, Acc. Chem. Res., 2007, 40, 141-150; Kool, ET, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, are contemplated as useful for the synthesis of the oligomers described herein. Examples of expanded-size nucleobases are shown below:

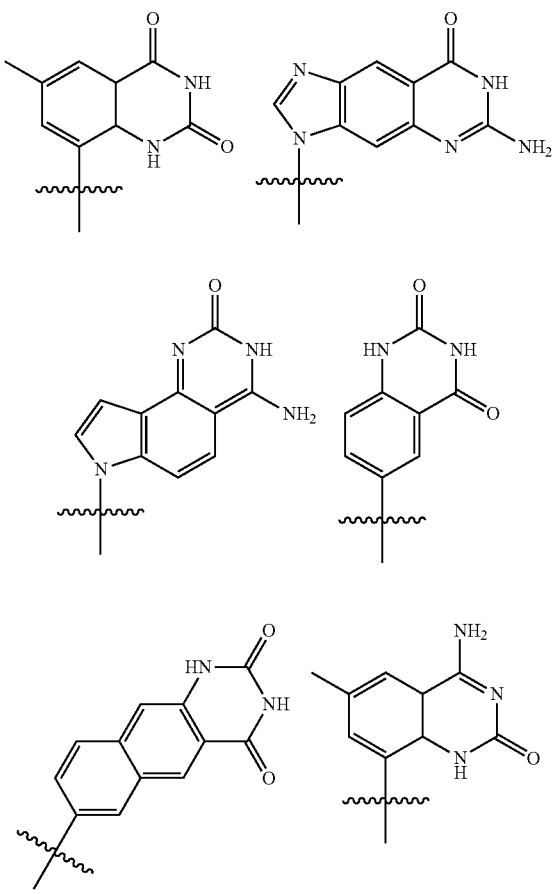

-continued

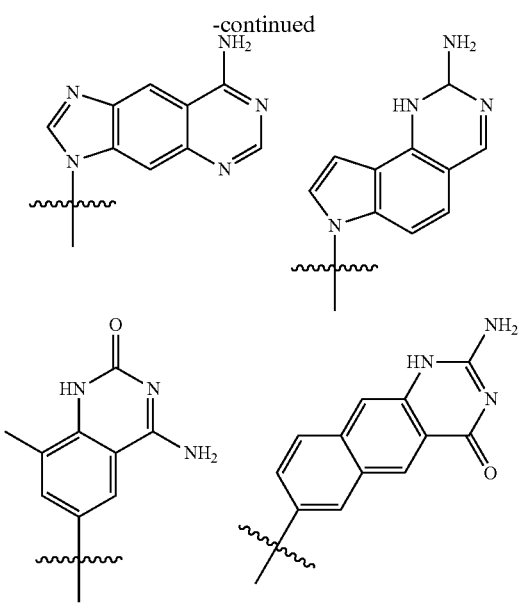

A nucleobase covalently linked to a ribose, sugar analog or morpholino comprises a nucleoside. "Nucleotides" are composed of a nucleoside together with one phosphate group. The phosphate groups covalently link adjacent nucleotides to one another to form an oligomer.

As used herein, any of the terms "deletion sequence", "gapmer", or "blebmer" generally refer to an oligomer sequence of nucleobases that has at least one fewer nucleobase compared to its target sequence. In various aspects and embodiments, any of the terms "deletion sequence", "gapmer", or "blebmer" specifically refer to a targeting sequence having a region complementary to at least one string of three or more identical contiguous nucleobases in a target sequence, wherein the target sequence comprises at least one additional nucleobase compared to the region of the targeting sequence and the at least one additional nucleobase has no complementary nucleobase in the region of the targeting sequence, and wherein the targeting region complementary to the at least one string of three or more identical contiguous nucleobases is internal to the targeting sequence. In the alternative or in addition to the preceding, in further aspects and embodiments, any of the terms "deletion sequence", "gapmer", or "blebmer" can also specifically refer to a targeting sequence having a region complementary to at least one biological palindrome sequence in a target sequence, wherein the target sequence comprises at least one additional nucleobase has no complementary nucleobase in the region of the targeting sequence, and wherein the targeting region complementary to the at least one biological palindrome sequence is internal to the targeting sequence.

As used herein, the term "biological palindrome sequence" refers to an oligonucleotide sequence wherein a portion of the oligonucleotide sequence, when read in reverse, is anti-sense to another portion of the oligonucleotide sequence.

As used herein, an oligomer "specifically hybridizes" to a target polynucleotide if the oligomer hybridizes to the target under physiological conditions, with a Tm substantially greater than 40° C. or 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Such hybridization may occur with "near" or "substantial" complementarity of the antisense oligomer to the target sequence, as well as with exact complementarity.

As used herein, "sufficient length" refers to an antisense oligomer or a targeting sequence thereof that is complementary to at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 or more, such as 8-40, and such as 15-40 contiguous nucleobases in a region, for example, of GAA intron 1, exon 2, or intron 2, or a region spanning any of the foregoing. An antisense oligomer of sufficient length has at least a minimal number of nucleotides to be capable of specifically hybridizing to a region, for example, of the GAA pre-mRNA repeat in the mutant RNA. Preferably an oligomer of sufficient length is from 8 to 30 nucleotides in length. More preferably, an oligomer of sufficient length is from 9 to 27 nucleotides in length. Even more preferably, an oligomer of sufficient length is from 15 to 40 nucleotides in length.

As used herein, the terms "sequence identity" or, for example, comprising a "sequence 50% identical to," refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

As used herein, a "subject" or a "subject in need thereof" includes, but is not limited to, a mammalian subject such as a human subject. Exemplary mammalian subjects have or are at risk for having GSD-II (or Pompe disease), or SMA, or DMD.

As used herein, the term "target" refers to a RNA region, and as a non-limiting example, to a region identified by the GAA gene. In a non-limiting embodiment the target is a region within intron 1 of the GAA-coding pre-mRNA, which is responsible for suppression of a signal that promotes exon 2 inclusion. In another embodiment the target region is a region of the mRNA of GAA exon 2. In a further embodiment, the target comprises one or more discrete subregions of intron 1 of the GAA-coding pre-mRNA.

As used herein, the term "target sequence" refers to a portion of the target RNA against which the oligomer analog is directed, that is, the sequence to which the oligomer analog will hybridize by Watson-Crick base pairing of a complementary sequence.

As used herein, the term "targeting sequence" is the sequence in the oligomer or oligomer analog that is complementary (meaning, in addition, substantially complementary) to the "target sequence" in the RNA genome. The entire sequence, or only a portion, of the antisense oligomer may be complementary to the target sequence. For example, in an oligomer having 20-30 bases, about 6, 7, 8, 9, 10, 11, 12, 13, 14, 15, 16, 17, 18, 19, 20, 21, 22, 23, 24, 25, 26, 27, 28, or 29 may be targeting sequences that are complementary to the target region. Typically, the targeting sequence is formed of contiguous bases in the oligomer, but may alternatively be formed of non-contiguous sequences that when placed together, e.g., from opposite ends of the oligomer, constitute sequence that spans the target sequence.

As used herein, "targeting sequence" may have "near" or "substantial" complementarity to the target sequence and still function for the purpose of the present disclosure, that is, still be "complementary." In embodiments, the oligomer analog compounds employed in the present disclosure have at most one mismatch with the target sequence out of 10 nucleotides, and preferably at most one mismatch out of 20. In embodiments, the oligomer analog compounds employed in the present disclosure have at least one mismatch with the target sequence out of 10 nucleotides, and preferably at least one mismatch out of 20. Alternatively, the antisense oligomers employed have at least 90% sequence homology, and preferably at least 95% sequence homology, with the exemplary targeting sequences as designated herein.

As used herein, the terms "TEG" or "triethylene glycol tail" refer to triethylene glycol moieties conjugated to the oligonucleotide, e.g., at its 3'- or 5'-end. For example, in some embodiments, "TEG" includes wherein, for example, T of the compound of formula (I), (VI), or (VII) is of the formula:

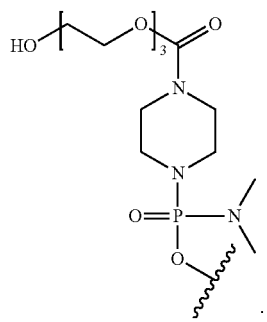

As used herein, the term "quantifying", "quantification" or other related words refer to determining the quantity, mass, or concentration in a unit volume, of a nucleic acid, polynucleotide, oligomer, peptide, polypeptide, or protein.

As used herein, "treatment" of a subject (e.g., a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

As used herein, a "heterocycle" refers to a non-aromatic ring, preferably a 5- to 7-membered ring, whose ring atoms are selected from the group consisting of carbon, nitrogen, oxygen and sulfur. Preferably, the ring atoms include 3 to 6 carbon atoms. Such heterocycles include, for example, pyrrolidine, piperidine, piperazine, and morpholine.

As used herein, a "morpholino oligomer" is an oligonucleotide analog composed of morpholino subunit structures, where (i) the structures are linked together by phosphorus-containing linkages, one to three atoms long, preferably two atoms long, and preferably uncharged, joining the morpholino nitrogen of one subunit to the 5' exocyclic carbon of an adjacent subunit, and (ii) Pi and Pj are purine or pyrimidine base-pairing moieties effective to bind, by base-specific hydrogen bonding, to a base in a polynucleotide. The purine or pyrimidine base-pairing moiety is typically adenine, cytosine; guanine, uracil or thymine. The synthesis, structures, and binding characteristics of morpholino oligomers are detailed in U.S. Pat. Nos. 5,698,685; 5,217,866; 5,142,047; 5,034,506; 5,166,315; 5,521,063; and 5,506,337, all of which are incorporated herein by reference. Desirable chemical properties of the morpholino-based oligomers include the ability to selectively hybridize with a complementary-base target nucleic acid, including target RNA, with high Tm, even with oligomers as short as 8-14 bases, the ability to be actively transported into mammalian cells, and the ability of an oligomer RNA heteroduplex to resist RNAse degradation.

As used herein, a "substantially uncharged" morpholino oligomer includes at most one charged intersubunit linkage for every four, preferably for every ten, and more preferably for every twenty, uncharged intersubunit linkages. Any charged linkages are preferably charged phosphoramidate (or thiophosphoramidate) linkages. Preferably, the morpholino oligomers are fully uncharged.

As used herein, an "amino acid subunit" is preferably an α-amino acid residue (i.e. —CO—CHR—NH—); it may also be a β- or other amino acid residue (e.g. —CO—CH2CHR—NH—), where R is a side chain.

As used herein, a "G-quartet" includes a stacked planar hydrogen-bonded guanine tetramers that can cause guanine-rich nucleic acids to adopt intermolecular and intramolecular quadruplex structures that are stabilized by the presence of the G-quartets.

As used herein, the term "non-natural amino acids" refers to those amino acids not present in proteins found in nature such as beta-alanine (β-Ala) or 6-aminohexanoic acid (Ahx).

As used herein, the abbreviation "DMD" refers to Duchenne muscular dystrophy.

As used herein, the abbreviation "SMA" refers to spinal muscular atrophy.

II. Description of the Disclosure

A. Antisense Oligomer Compounds

In an aspect, the antisense oligomer compound is a synthetic oligomer capable of base-specific binding to a target sequence of a polynucleotide, e.g., an antisense oligonucleotide analog. Such analogs, in which the backbone structure, ring structure, or, less frequently, base structure of natural polynucleotides is modified, are well known and include charged analogs, such as phosphorothioate-linked oligonucleotides, and uncharged analogs, such as methylphosphonates and peptide nucleic acids. Some analogs, such as N3'→P5' phosphoramidates, may be charged or uncharged, depending on the substation on the linking moiety.

In embodiments, the antisense oligomer compound is a morpholino oligomer, as defined above, which is about 8-40 subunits in length. More typically, the oligomer is about 10-30, or about 12-25, subunits in length. For some applications, such as antibacterial, short oligomers, e.g. from about 8-12 subunits in length, can be especially advantageous, particularly when attached to a peptide transporter as disclosed herein. Preferably, the oligomer is an uncharged phosphorodiamidate-linked morpholino oligomer (PMO), also defined above. The PMO can be of any sequence, where the supported base pairing groups include standard or modified A, T, C, G, I and U bases.

In an aspect, the target nucleic acid sequence against which the oligomer compound is directed includes a region having a string of three or more identical contiguous nucleobases. In embodiments, the three or more identical contiguous nucleobases are three identical contiguous nucleobases. In embodiments, the three or more identical contiguous nucleobases are four identical contiguous nucleobases. In embodiments, the three or more identical contiguous nucleobases are five identical contiguous nucleobases. In embodiments, the three or more identical contiguous nucleobases are six identical contiguous nucleobases. In embodiments, the three or more identical contiguous nucleobases are seven identical contiguous nucleobases. In embodiments, the three or more identical contiguous nucleobases are eight identical contiguous nucleobases. In embodiments, the three or more identical contiguous nucleobases are nine or more identical contiguous nucleobases.

In embodiments, the three or more identical contiguous nucleobases are reduced to two identical contiguous nucleobases. In embodiments, the three identical contiguous nucleobases are reduced to two identical contiguous nucleobases (i.e., one nucleobase is removed). In embodiments, the four identical contiguous nucleobases are reduced to two identical contiguous nucleobases (i.e., two nucleobases are removed). In embodiments, the five identical contiguous nucleobases are reduced to two identical contiguous nucleobases (i.e., three nucleobases are removed). In embodiments, the six identical contiguous nucleobases are reduced to two identical contiguous nucleobases (i.e., four nucleobases are removed). The same nucleobase removal approach can be made to more than six identical contiguous nucleobases.

In further embodiments, the string of three or more identical contiguous nucleobases is a string of three or more contiguous G nucleobases. In embodiments, the string of three or more contiguous G nucleobases is three contiguous G nucleobases. In embodiments, the string of three or more contiguous G nucleobases is four, five, six, seven, eight, nine, or more contiguous G nucleobases.

In embodiments, the three or more contiguous G nucleobases are reduced to two contiguous G nucleobases. In embodiments, three contiguous G nucleobases are reduced to two contiguous G nucleobases (i.e., one G nucleobase is removed). In embodiments, four contiguous G nucleobases are reduced to two contiguous G nucleobases (i.e., two G nucleobases are removed). In embodiments, five contiguous G nucleobases are reduced to two contiguous G nucleobases (i.e., three G nucleobases are removed). In embodiments, six contiguous G nucleobases are reduced to two contiguous G nucleobases (i.e., four G nucleobases are removed). The same nucleobase removal approach can be made to more than six identical contiguous G nucleobases.

According to an aspect, the target nucleic acid sequence against which the oligomer compound is directed includes a region having a biological palindrome sequence. Alternatively, the target region may include or be adjacent to a donor or acceptor splice site in a preprocessed mRNA, where it is desired to block correct splicing at that site, either for purposes of creating splice mutation polypeptides, or incomplete or inactive peptides. In still another embodiment, the target may be a cis-acting element in a viral genome, where binding of the oligomer (which may be targeted against either the + or − viral genome strand), is effective to block viral replication in virus-infected cells.

Exemplary target sequences containing a string of three or four or more nucleobases or a biological palindrome sequence in each of these target types can be found from public sequence databases known to those of skill in the art. It is to be appreciated, however, that various deletions in the targeting sequence described throughout this disclosure are illustrative of how the oligomer compound may be modified to achieve the advantages of the invention.

The transporter can be linked to the compound to be delivered by a variety of methods available to one of skill in the art. In one example, the transporter is a peptide containing a single cysteine residue whose side chain thiol is used for linking. The linkage point can be at various locations along the transporter. In selected embodiments, it is at a terminus of the transporter. Typically, it is adjacent to the hydrophobic residues of the transporter. Multiple transporters can be attached to a single compound if desired.

The linker can also be any combination of two β-Ala and/or Ahx residues attached to the 5' end of the PMO and the C-terminus of the peptide transporter. A preferred embodiment is to attach the Ahx residue to the C terminus of the peptide transporter and the β-Ala residue to the 5' terminus of the PMO.

When the compound is a PMO, the transporter can be attached at the 5' end of the PMO, e.g., via the 5'-hydroxyl group, or via an amine capping moiety. Alternatively, the transporter may be attached at the 3' end, e.g. via a morpholino ring nitrogen, or via the side chain of an intersubunit linkage, either at a terminus or an internal linkage. The linker may also comprise a direct bond between the carboxy terminus of a transporter peptide and an amine or hydroxy group of the PMO, formed by condensation promoted by e.g., carbodiimide.

Linkers can be selected from those which are non-cleavable under normal conditions of use, e.g., containing a thioether or carbamate bond. In some embodiments, it may be desirable to include a linkage between the transporter moiety and compound which is cleavable in vivo. Bonds which are cleavable in vivo are known in the art and include, for example, carboxylic acid esters, which are hydrolyzed enzymatically, and disulfides, which are cleaved in the presence of glutathione. It may also be feasible to cleave a photolytically cleavable linkage, such as an ortho-nitrophenyl ether, in vivo by application of radiation of the appropriate wavelength.

For example, the preparation of a conjugate having a disulfide linker, using the reagent N-succinimidyl 3-(2-pyridyldithio) propionate (SPDP) or succinimidyloxycarbonyl α-methyl-α-(2-pyridyldithio) toluene (SMPT). Exemplary heterobifunctional linking agents which further contain a cleavable disulfide group include N-hydroxysuccinimidyl 3-[(4-azidophenyl)dithio]propionate and others described in (See: Vanin and Ji, 1981).

In embodiments, antisense targeting sequences are designed to hybridize to a region of one or more of the target sequences. Selected antisense targeting sequences can be made shorter, e.g., about 12 bases, or longer, e.g., about 40 bases, and include a small number of mismatches, as long as the sequence is sufficiently complementary to effect splice modulation upon hybridization to the target sequence, and optionally forms with the RNA a heteroduplex having a Tm of 45° C. or greater.

In embodiments, the degree of complementarity between the target sequence and antisense targeting sequence is sufficient to form a stable duplex. The region of complementarity of the antisense oligomers with the target RNA sequence may be as short as 8-11 bases, but can be 12-15 bases or more, e.g., 10-40 bases, 12-30 bases, 12-25 bases, 15-25 bases, 12-20 bases, or 15-20 bases, including all integers in between these ranges. An antisense oligomer of about 14-15 bases is generally long enough to have a unique complementary sequence. In certain embodiments, a minimum length of complementary bases may be required to achieve the requisite binding Tm, as discussed herein.

In embodiments, oligomers as long as 40 bases may be suitable, where at least a minimum number of bases, e.g., 10-12 bases, are complementary to the target sequence. In some embodiments, facilitated or active uptake in cells is optimized at oligomer lengths of less than about 30 bases. For PMO oligomers, described further herein, an optimum balance of binding stability and uptake generally occurs at lengths of 18-25 bases. Included in the disclosure are antisense oligomers (e.g., PMOs, PMO-X, PNAs, LNAs, 2'-OMe) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to the target sequences.

In embodiments, the antisense oligomers typically comprise a base sequence which is sufficiently complementary to a sequence or region within or adjacent to intron 1, exon 2, or intron 2 of the pre-mRNA sequence of the human GAA gene. Ideally, an antisense oligomer is able to effectively modulate aberrant splicing of the GAA pre-mRNA, and thereby increase expression of active GAA protein. This requirement is optionally met when the oligomer compound has the ability to be actively taken up by mammalian cells, and once taken up, form a stable duplex (or heteroduplex) with the target mRNA, optionally with a Tm greater than about 40° C. or 45° C.

In embodiments, the antisense oligomers typically comprise a base sequence which is sufficiently complementary to a sequence or region within or adjacent to exons associated with DMD, SMA, or Pompe disease.

In embodiments, antisense oligomers may be 100% complementary to the target sequence, or may include mismatches, e.g., to accommodate variants, as long as a heteroduplex formed between the oligomer and target sequence is sufficiently stable to withstand the action of cellular nucleases and other modes of degradation which may occur in vivo. Hence, certain oligomers may have substantial complementarity, meaning, about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligomer and the target sequence. Oligomer backbones that are less susceptible to cleavage by nucleases are discussed herein. Mismatches, if present, are typically less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the v target sequence, it is effective to stably and specifically bind to the target sequence, such that splicing of the target pre-RNA is modulated.

The stability of the duplex formed between an oligomer and a target sequence is a function of the binding Tm and the susceptibility of the duplex to cellular enzymatic cleavage. The Tm of an oligomer with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligomer Hybridization Techniques, Methods Enzymol. Vol. 154 pp. 94-107. In certain embodiments, antisense oligomers may have a binding Tm, with respect to a complementary-sequence RNA, of greater than about body temperature and preferably greater than about 45° C. or 50° C. Tm's in the range 60-80° C. or greater are also included. According to well-known principles, the Tm of an oligomer, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high Tm (45-50° C. or greater) at a length of 25 bases or less are generally preferred over those requiring greater than 25 bases for high Tm values.

The activity of antisense oligomers and variants thereof can be assayed according to routine techniques in the art. For example, splice forms and expression levels of surveyed RNAs and proteins may be assessed by any of a wide variety of well-known methods for detecting splice forms and/or expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e., a transcribed polynucleotide) from a cell, tissue or organism, and by hybridizing the mRNA/cDNA with a reference polynucleotide that is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcript(s).

B. Antisense Oligomer Chemistries i. General Characteristics

Certain antisense oligomers of the present disclosure specifically hybridize to an intronic splice silencer element or an exonic splice silencer element. In certain embodiments, the antisense oligomer comprises a non-natural chemical backbone selected from a phosphoramidate or phosphorodiamidate morpholino oligomer (PMO), a peptide nucleic acid (PNA), a locked nucleic acid (LNA), a phosphorothioate oligomer, a tricyclo-DNA oligomer, a tricyclo-phosphorothioate oligomer, a 2'O-Me-modified oligomer, or any combination of the foregoing, and a targeting sequence complementary to a region within intron 1, intron 2, or exon 2 of a pre-mRNA of the human acid alpha-glucosidase (GAA) gene.

Antisense oligomers of the present disclosure generally comprise a plurality of nucleotide subunits each bearing a nucleobase which taken together form or comprise a targeting sequence. Accordingly, in some embodiments, the antisense oligomers range in length from about 10 to about 40 subunits, more preferably about 10 to 30 subunits, and typically 15-25 subunits. For example, antisense compounds of the disclosure may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subunits in length, or range from 10 subunits to 40 subunits, 10 subunits to 30 subunits, 14 subunits to 25 subunits, 15 subunits to 30 subunits, 17 subunits to 30 subunits, 17 subunits to 27 subunits, 10 subunits to 27 subunits, 10 subunits to 25 subunits, and 10 subunits to 20 subunits. In certain embodiments, the antisense oligomer is about 10 to about 40 or about 5 to about 30 nucleotides in length. In some embodiments, the antisense oligomer is about 14 to about 25 or about 17 to about 27 nucleotides in length.

In various embodiments, an antisense oligomer comprises a completely modified backbone, for example, 100% of the backbone is modified (for example, a 25 mer antisense oligomer comprises its entire backbone modified with any combination of the backbone modifications as described herein). In various embodiments, an antisense oligomer may comprise about 100% to 2.5% of its backbone modified. In various embodiments, an antisense oligomer may comprise about 99%, 95%, 90%, 85%, 80%, 75%, 70%, 65%, 60%, 55%, 50%, 45%, 40%, 35%, 30%, 25%, 20%, 15%, 10%, 5%, or 2.5% of its backbone modified, and iterations in between. In other embodiments, an antisense oligomer may comprise any combination of backbone modifications as described herein.

In various embodiments, an antisense oligomer comprises, consists of, or consists essentially of phosphoramidate morpholino oligomers and phosphorodiamidate morpholino oligomers (PMO), phosphorothioate modified oligomers, 2' O-methyl modified oligomers, peptide nucleic acid (PNA), locked nucleic acid (LNA), phosphorothioate oligomers, 2' O-MOE modified oligomers, 2'-fluoro-modified oligomer, 2'O,4'C-ethylene-bridged nucleic acids (ENAs), tricyclo-DNAs, tricyclo-DNA phosphorothioate nucleotides, 2'-O-[2-(N-methylcarbamoyl)ethyl] modified oligomers, morpholino oligomers, peptide-conjugated phosphoramidate morpholino oligomers (PPMO), phosphorodiamidate morpholino oligomers having a phosphorous atom with (i) a covalent bond to the nitrogen atom of a morpholino ring, and (ii) a second covalent bond to a (1,4-piperazin)-1-yl substituent or to a substituted (1,4-piperazin)-1-yl (PMOplus), and phosphorodiamidate morpholino oligomers having a phosphorus atom with (i) a covalent bond to the nitrogen atom of a morpholino ring and (ii) a second covalent bond to the ring nitrogen of a 4-aminopiperdin-1-yl (i.e., APN) or a derivative of 4-aminopiperdin-1-yl (PMO-X) chemistries, including combinations of any of the foregoing.

In an aspect, the antisense oligomers described herein comprise an antisense PPMO oligomer. In embodiments, the antisense PPMO oligomer comprises three, four, five, six, seven, eight, nine or more internal contiguous nucleobases. In embodiments, removal of one or more of the contiguous nucleobases is made such that there are only two contiguous nucleobases, which results in a removal of aggregated structures.

In embodiments, the antisense PPMO oligomer comprises three, four, five, six, seven, eight, nine or more internal contiguous G nucleobases. In embodiments, removal of one or more of the contiguous G nucleobases is made such that there are only two contiguous G nucleobases, which results in a removal of aggregated structures.

In various embodiments, the backbone of the antisense oligomer is substantially uncharged, and is optionally recognized as a substrate for active or facilitated transport across the cell membrane. In some embodiments, all the internucleoside linkages are uncharged. The ability of the oligomer to form a stable duplex with the target RNA may also relate to other features of the backbone, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell cytoplasm.

In certain embodiments, the antisense oligomer has at least one internucleoside linkage that is positively charged or cationic at physiological pH. In some embodiments, the antisense oligomer has at least one internucleoside linkage that exhibits a pKa between about 5.5 and about 12. In further embodiments, the antisense oligomer contains about, at least about, or no more than about 1, 2, 3, 4, 5, 6, 7, 8, 9, or 10 internucleoside linkages that exhibits a pKa between about 4.5 and about 12. In some embodiments, the antisense oligomer contains about or at least about 10%, 15%, 20%, 25%, 30%, 35%, 40%, 45%, 50%, 55%, 60%, 65%, 70%, 75%, 80%, 85%, 90%, 95%, or 100% internucleoside linkages that exhibit a pKa between about 4.5 and about 12. Optionally, the antisense oligomer has at least one internucleoside linkage with both a basic nitrogen and an alkyl, aryl, or aralkyl group. In particular embodiments, the cationic internucleoside linkage or linkages comprise a 4-aminopiperdin-1-yl (APN) group, or a derivative thereof. While not being bound by any one theory, it is believed that the presence of a cationic linkage or linkages (e.g., APN group or APN derivative) in the oligomer facilitates binding to the negatively charged phosphates in the target nucleotide. Thus, the formation of a heteroduplex between mutant RNA and the cationic linkage-containing oligomer may be held together by both an ionic attractive force and Watson-Crick base pairing.

In some embodiments, the number of cationic linkages is at least 2 and no more than about half the total internucleoside linkages, e.g., about or no more than about 1, 2, 3, 4, 5, 6, 7, 8, 9, 10, 11, 12, 13, 14, 15, 16, 17, 18, 19, 20 cationic linkages. In some embodiments, however, up to all of the internucleoside linkages are cationic linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are cationic linkages. In specific embodiments, an oligomer of about 19-20 subunits may have 2-10, e.g., 4-8, cationic linkages, and the remainder uncharged linkages. In other specific embodiments, an oligomer of 14-15 subunits may have 2-7, e.g., 2, 3, 4, 5, 6, or 7 cationic linkages and the remainder uncharged linkages. The total number of cationic linkages in the oligomer can thus vary from about 1 to 10 to 15 to 20 to 30 or more (including all integers in between), and can be interspersed throughout the oligomer.

In various embodiments, an antisense oligomer may have about or up to about 1 cationic linkage per every 2-5 or 2, 3, 4, or 5 uncharged linkages, such as about 4-5 or 4 or 5 per every 10 uncharged linkages.

Certain embodiments include antisense oligomers that contain about 10%, 15%, 20%, 25%, 30%, 35%, 40%, 45%, 50%, 55%, 60%, 65%, 70%, 75%, 80%, 85%, 90%, 95%, or 100% cationic linkages. In certain embodiments, optimal improvement in antisense activity may be seen if about 25% of the backbone linkages are cationic. In certain embodiments, enhancement may be seen with a small number e.g., 10-20% cationic linkages, or where the number of cationic linkages is in the range 50-80%, such as about 60%.

In various embodiments, the cationic linkages are interspersed along the backbone. Such oligomers optionally contain at least two consecutive uncharged linkages; that is, the oligomer optionally does not have a strictly alternating pattern along its entire length. In specific instances, each one or two cationic linkage(s) is/are separated along the backbone by at least 1, 2, 3, 4, or 5 uncharged linkages.

Also included are oligomers having blocks of cationic linkages and blocks of uncharged linkages. For example, a central block of uncharged linkages may be flanked by blocks of cationic linkages, or vice versa. In some embodiments, the oligomer has approximately equal-length 5', 3' and center regions, and the percentage of cationic linkages in the center region is greater than about 50%, 60%, 70%, or 80% of the total number of cationic linkages.

In certain antisense oligomers, the bulk of the cationic linkages (e.g., 70, 75%, 80%, 90% of the cationic linkages) are distributed close to the "center-region" backbone linkages, e.g., the 6, 7, 8, 9, 10, 11, 12, 13, 14, or 15 centermost linkages. For example, a 16, 17, 18, 19, 20, 21, 22, 23, or 24-mer oligomer with may have at least 50%, 60%, 70%, or 80% of the total cationic linkages localized to the 8, 9, 10, 11, or 12 centermost linkages.

ii. Backbone Chemistry Features

The antisense oligomers can employ a variety of antisense chemistries. Examples of oligomer chemistries include, without limitation, phosphoramidate morpholino oligomers and phosphorodiamidate morpholino oligomers (PMO), phosphorothioate modified oligomers, 2' O-methyl modified oligomers, peptide nucleic acid (PNA), locked nucleic acid (LNA), phosphorothioate oligomers, 2' O-MOE modified oligomers, 2'-fluoro-modified oligomer, 2'O,4'C-ethylene-bridged nucleic acids (ENAs), tricyclo-DNAs, tricyclo-DNA phosphorothioate nucleotides, 2'-O-[2-(N-methylcarbamoyl)ethyl] modified oligomers, morpholino oligomers, peptide-conjugated phosphoramidate morpholino oligomers (PPMO), phosphorodiamidate morpholino oligomers having a phosphorous atom with (i) a covalent bonds to the nitrogen atom of a morpholino ring, and (ii) a second covalent bond to a (1,4-piperazin)-1-yl substituent or to a substituted (1,4-piperazin)-1-yl (PMOplus), and phosphorodiamidate morpholino oligomers having a phosphorus atom with (i) a covalent bond to the nitrogen atom of a morpholino ring and (ii) a second covalent bond to the ring nitrogen of a 4-aminopiperdin-1-yl (i.e., APN) or a derivative of 4-aminopiperdin-1-yl (PMO-X) chemistries, including combinations of any of the foregoing. In general, PNA and LNA chemistries can utilize shorter targeting sequences because of their relatively high target binding strength relative to PMO and 2'O-Me modified oligomers. Phosphorothioate and 2'O-Me-modified chemistries can be combined to generate a 2'O-Me-phosphorothioate backbone. See, e.g., PCT Publication Nos. WO/2013/112053 and WO/2009/008725, which are hereby incorporated by reference in their entireties.

In some instances, antisense oligomers such as PMOs can be conjugated to cell penetrating peptides (CPPs) to facilitate intracellular delivery. Peptide-conjugated PMOs are called PPMOs and certain embodiments include those described in PCT Publication No. WO/2012/150960, incorporated herein by reference in its entirety. In some embodiments, an arginine-rich peptide sequence conjugated or linked to, for example, the 3' terminal end of an antisense oligomer as described herein may be used. In certain embodiments, an arginine-rich peptide sequence conjugated or linked to, for example, the 5' terminal end of an antisense oligomer as described herein may be used.

1. Peptide Nucleic Acids (PNAs)

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligomers obeying Watson-Crick base-pairing rules, and mimic DNA in terms of base pair recognition (See: Egholm, Buchardt et al., 1993). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases. A non-limiting example of a PNA is depicted below:

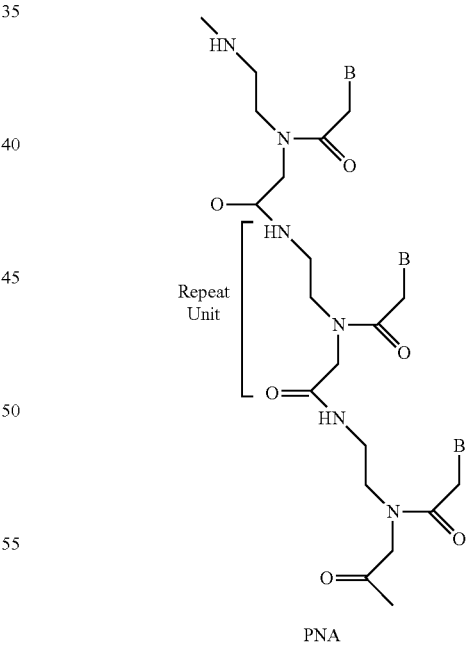

PNA

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969, 766, 7,211,668, 7,022,851, 7,125,994, 7,145,006 and 7,179, 896. See also U.S. Pat. Nos. 5,539; 082; 5,714,331; and 5,719,262 for the preparation of PNAs. Further teaching of PNA compounds can be found in Nielsen et al., Science, 254:1497-1500, 1991. Each of the foregoing is incorporated by reference in its entirety.

2. Locked Nucleic Acids (LNAs)

Antisense oligomer compounds may also contain "locked nucleic acid" subunits (LNAs). "LNAs" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., Chemical Communications (1998) 455; Tetrahedron (1998) 54:3607, and Accounts of Chem. Research (1999) 32:301); Obika, et al., Tetrahedron Letters (1997) 38:8735; (1998) 39:5401, and Bioorganic Medicinal Chemistry (2008) 16:9230, which are hereby incorporated by reference in their entirety. A non-limiting example of an LNA is depicted below:

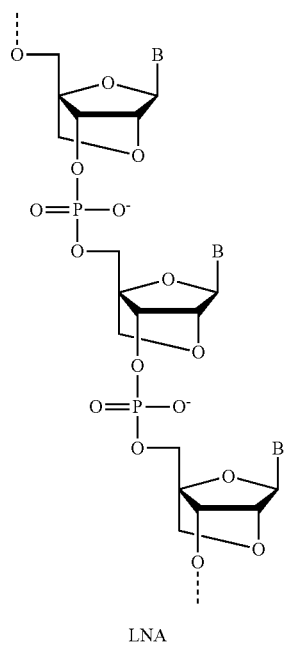

LNA

Compounds of the disclosure may incorporate one or more LNAs; in some cases, the compounds may be entirely composed of LNAs. Methods for the synthesis of individual LNA nucleoside subunits and their incorporation into oligomers are described, for example, in U.S. Pat. Nos. 7,572, 582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. Further embodiments include an LNA containing compound where each LNA subunit is separated by a DNA subunit. Certain compounds are composed of alternating LNA and DNA subunits where the intersubunit linker is phosphorothioate.

2'O,4'C-ethylene-bridged nucleic acids (ENAs) are another member of the class of BNAs. A non-limiting example is depicted below:

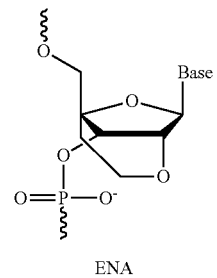

ENA

ENA oligomers and their preparation are described in Obika et al., Tetrahedron Ltt 38 (50): 8735, which is hereby incorporated by reference in its entirety. Compounds of the disclosure may incorporate one or more ENA subunits.

3. Phosphorothioates

"Phosphorothioates" (or S-oligos) are a variant of normal DNA in which one of the nonbridging oxygens is replaced by a sulfur. A non-limiting example of a phosphorothioate is depicted below:

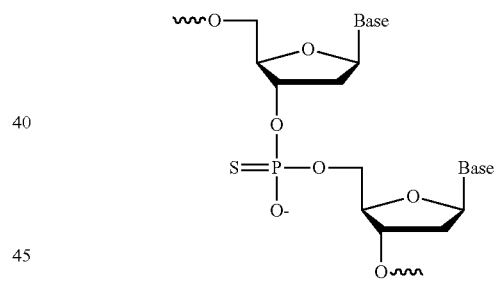

The sulfurization of the internucleotide bond reduces the action of endo- and exonucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1, 2-bensodithiol-3-one 1, 1-dioxide (BDTD) (see, e.g., Iyer et al., J. Org. Chem. 55, 4693-4699, 1990, which are hereby incorporated by reference in their entirety). The latter methods avoid the problem of elemental sulfur's insolubility in most organic solvents and the toxicity of carbon disulfide. The TETD and BDTD methods also yield higher purity phosphorothioates.

4. Triclyclo-DNAs and Tricyclo-Phosphorothioate Nucleotides

Tricyclo-DNAs (tc-DNA) are a class of constrained DNA analogs in which each nucleotide is modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs. Tricyclo-DNAs and their synthesis are described in International Patent Application Publication No. WO 2010/115993, which are hereby incorporated by reference in their entirety. Compounds of the disclosure may incorporate one or more tricyclo-DNA nucleotides; in some cases, the compounds may be entirely composed of tricycle-DNA nucleotides.

Tricyclo-phosphorothioate nucleotides are tricyclo-DNA nucleotides with phosphorothioate intersubunit linkages. Tricyclo-phosphorothioate nucleotides and their synthesis are described in International Patent Application Publication No. WO 2013/053928, which are hereby incorporated by reference in their entirety. Compounds of the disclosure may incorporate one or more tricycle-DNA nucleotides; in some cases, the compounds may be entirely composed of tricycle-DNA nucleotides. A non-limiting example of a tricycle-DNA/tricycle-phophothioate nucleotide is depicted below:

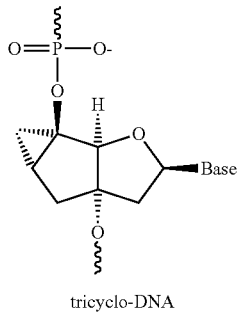

tricyclo-DNA 5. 2' O-Methyl, 2' O-MOE, and 2'-F Oligomers

"2'O-Me oligomer" molecules carry a methyl group at the 2'-OH residue of the ribose molecule. 2'-O-Me-RNAs show the same (or similar) behavior as DNA, but are protected against nuclease degradation. 2'-O-Me-RNAs can also be combined with phosphothioate oligomers (PTOs) for further stabilization. 2'O-Me oligomers (phosphodiester or phosphothioate) can be synthesized according to routine techniques in the art (see, e.g., Yoo et al., Nucleic Acids Res. 32:2008-16, 2004, which is hereby incorporated by reference in its entirety). A non-limiting example of a 2' O-Me oligomer is depicted below:

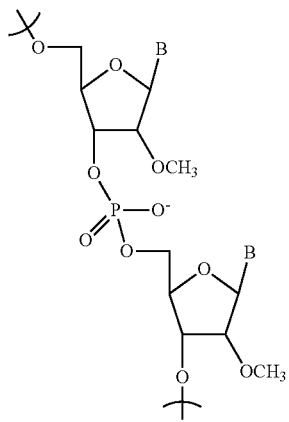

2' O-Me oligomers may also comprise a phosphorothioate linkage (2' O-Me phosphorothioate oligomers). 2' O-Methoxyethyl Oligomers (2'-O MOE), like 2' O-Me oligomers, carry a methoxyethyl group at the 2'-OH residue of the ribose molecule and are discussed in Martin et al., Helv. Chim. Acta, 78, 486-504, 1995, which are hereby incorporated by reference in their entirety. A non-limiting example of a 2' O-MOE nucleotide is depicted below:

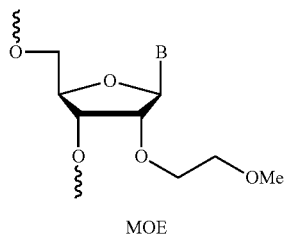

MOE

In contrast to the preceding alkylated 2'OH ribose derivatives, 2'-fluoro oligomers have a fluoro radical in at the 2' position in place of the 2'OH. A non-limiting example of a 2'-F oligomer is depicted below:

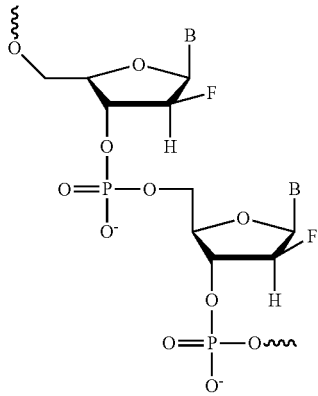

2'-fluoro oligomers are further described in WO 2004/043977, which is hereby incorporated by reference in its entirety. Compounds of the disclosure may incorporate one or more 2'O-Methyl, 2' O-MOE, and 2'-F subunits and may utilize any of the intersubunit linkages described here. In some instances, a compound of the disclosure could be composed of entirely 2'O-Methyl, 2' O-MOE, or 2'-F subunits. One embodiment of a compound of the disclosure is composed entirely of 2'O-methyl subunits.

6. 2'-O-[2-(N-methylcarbamoyl)ethyl] Oligonucleotides (MCEs)

MCEs are another example of 2'O modified ribonucleosides useful in the compounds of the disclosure. Here, the 2'OH is derivatized to a 2-(N-methylcarbamoyl)ethyl moiety to increase nuclease resistance. A non-limiting example of an MCE oligomer is depicted below:

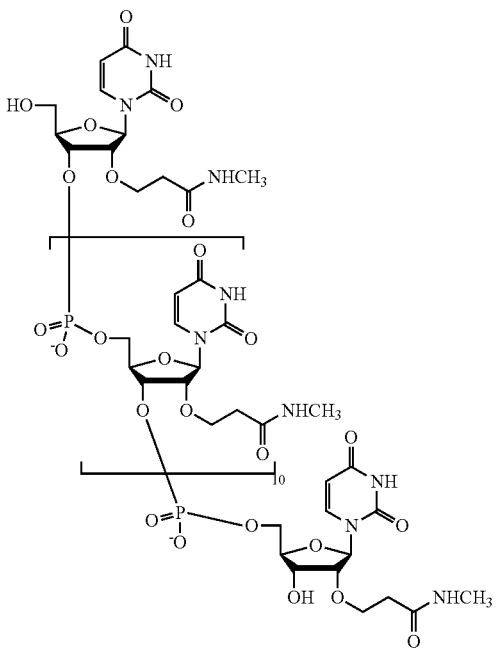

MCEs and their synthesis are described in Yamada et al., J. Org. Chem., 76(9):3042-53, which is hereby incorporated by reference in its entirety. Compounds of the disclosure may incorporate one or more MCE subunits.

7. Stereo Specific Oligomers

Stereo specific oligomers are those which the stereo chemistry of each phosphorous-containing linkage is fixed by the method of synthesis such that a substantially pure single oligomer is produced. A non-limiting example of a stereo specific oligomer is depicted below:

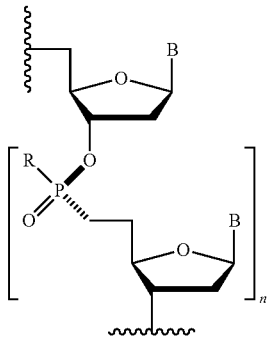

In the above example, each phosphorous of the oligomer has the same stereo chemistry. Additional examples include the oligomers described above. For example, LNAs, ENAs, Tricyclo-DNAs, MCEs, 2' O-Methyl, 2' O-MOE, 2'-F, and morpholino-based oligomers can be prepared with stereospecific phosphorous-containing internucleoside linkages such as, for example, phosphorothioate, phosphodiester, phosphoramidate, phosphorodiamidate, or other phosphorous-containing internucleoside linkages. Stereo specific oligomers, methods of preparation, chirol controlled synthesis, chiral design, and chiral auxiliaries for use in preparation of such oligomers are detailed, for example, in WO2015107425, WO2015108048, WO2015108046, WO2015108047, WO2012039448, WO2010064146, WO2011034072, WO2014010250, WO2014012081, WO20130127858, and WO2011005761, each of which is hereby incorporated by reference in its entirety.

8. Morpholino-Based Oligomers

Morpholino-based oligomers refer to an oligomer comprising morpholino subunits supporting a nucleobase and, instead of a ribose, contains a morpholine ring. Exemplary internucleoside linkages include, for example, phosphoramidate or phosphorodiamidate internucleoside linkages joining the morpholine ring nitrogen of one morpholino subunit to the 4' exocyclic carbon of an adjacent morpholino subunit. Each morpholino subunit comprises a purine or pyrimidine nucleobase effective to bind, by base-specific hydrogen bonding, to a base in an oligonucleotide.

Morpholino-based oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT Publication No. WO/2009/064471 and WO/2012/043730 and Summerton et al. 1997, Antisense and Nucleic Acid Drug Development, 7, 187-195, which are hereby incorporated by reference in their entirety. Within the oligomer structure, the phosphate groups are commonly referred to as forming the "internucleoside linkages" of the oligomer. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic intersubunit linkages of morpholino-based oligomers described herein, one nitrogen is always pendant to the backbone chain. The second nitrogen, in a phosphorodiamidate linkage, is typically the ring nitrogen in a morpholine ring structure.

"PMO-X" refers to phosphorodiamidate morpholino-based oligomers having a phosphorus atom with (i) a covalent bond to the nitrogen atom of a morpholine ring and (ii) a second covalent bond to the ring nitrogen of a 4-aminopiperdin-1-yl (i.e., APN) or a derivative of 4-aminopiperdin-1-yl. Exemplary and non-limiting PMO-X oligomers are disclosed in PCT Application No. PCT/US2011/38459 and PCT Publication No. WO 2013/074834, which are hereby incorporated by reference in their entirety. PMO-X includes "PMO-apn" or "APN," which refers to a PMO-X oligomer which comprises at least one internucleoside linkage where a phosphorus atom is linked to a morpholino group and to the ring nitrogen of a 4-aminopiperdin-1-yl (i.e., APN). In specific embodiments, an antisense oligomer comprising a targeting sequence comprises at least one APN-containing linkage or APN derivative-containing linkage. Various embodiments include morpholino-based oligomers that have about 10%, 15%, 20%, 25%, 30%, 35%, 40%, 45%, 50%, 55%, 60%, 65%, 70%, 75%, 80%, 85%, 90%, 95%, or 100% APN/APN derivative-containing linkages, where the remaining linkages (if less than 100%) are uncharged linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are APN/APN derivative-containing linkages.

In some embodiments, the antisense oligomer is a compound of formula (I):

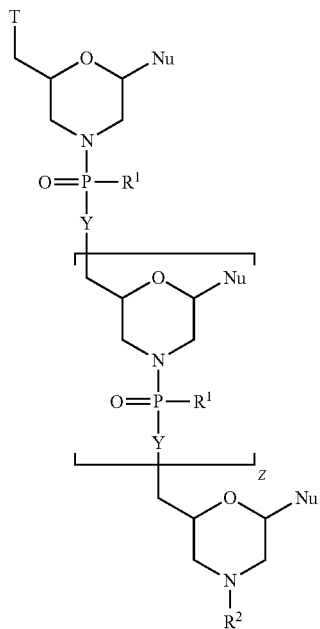

or a pharmaceutically acceptable salt thereof, wherein:

each Nu is a nucleobase which taken together form a targeting sequence;

Z is an integer from 8 to 38;

each Y is independently selected from O and $-NR^4$, wherein each $R^4$ is independently selected from H, $C_1$-$C_6$ alkyl, aralkyl, $-C(=NH)NH_2$, $-C(O)(CH_2)_nNR^5C(=NH)NH_2$, $-C(O)(CH_2)_2NHC(O)(CH_2)_5NR^5C(=NH)NH_2$, and G, wherein $R^5$ is selected from H and $C_1$-$C_6$ alkyl and n is an integer from 1 to 5;

T is selected from OH and a moiety of the formula:

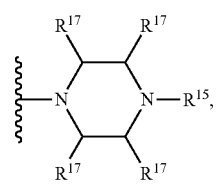

wherein:

A is selected from $-OH$, $-N(R^7)_2$, and $R^1$ wherein each $R^7$ is independently selected from H and $C_1$-$C_6$ alkyl, and $R^6$ is selected from OH, $-N(R^9)CH_2C(O)NH_2$, and a moiety of the formula:

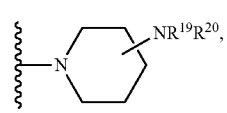

wherein:

$R^9$ is selected from H and $C_1$-$C_6$ alkyl; and $R^{10}$ is selected from G, $-C(O)-R^{11}OH$, acyl, trityl, 4-methoxytrityl, $-C(=NH)NH_2$, $-C(O)(CH_2)_mNR^{12}C(=NH)NH_2$, and $-C(O)(CH_2)_2NHC(O)(CH_2)_5NR^{12}C(=NH)NH_2$, wherein:

m is an integer from 1 to 5, $R^{11}$ is of the formula $-(O-alkyl)_y-$ wherein y is an integer from 3 to 10 and each of the y alkyl groups is independently selected from $C_2$-$C_6$ alkyl; and $R^{12}$ is selected from H and $C_1$-$C_6$ alkyl;

each instance of R' is independently selected from:

$-N(R^{13})_2$, wherein each $R^{13}$ is independently selected from H and $C_1$-$C_6$ alkyl; a moiety of formula (II):

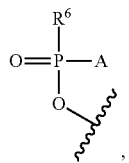

wherein:

$R^{15}$ is selected from H, G, $C_1$-$C_6$ alkyl, $-C(=NH)NH_2$, $-C(O)(CH_2)_qNR^{18}C(=NH)NH_2$, and $-C(O)(CH_2)_2NHC(O)(CH_2)_5NR^{18}C(=NH)NH_2$, wherein:

$R^{18}$ is selected from H and $C_1$-$C_6$ alkyl; and q is an integer from 1 to 5, and each $R^{17}$ is independently selected from H and methyl; and a moiety of formula(III):

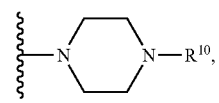

wherein:

$R^{19}$ is selected from H, $C_1$-$C_6$ alkyl, $-C(=NH)NH_2$, $-C(O)(CH_2)_rNR^{22}C(=NH)NH_2$, $-C(O)CH(NH_2)(CH_2)_3NHC(=NH)NH_2$, $-C(O)(CH_2)_2NHC(O)(CH_2)_5NR^{22}C(=NH)NH_2$, $-C(O)CH(NH_2)(CH_2)_4NH_2$ and G, wherein:

$R^{22}$ is selected from H and $C_1$-$C_6$ alkyl; and r is an integer from 1 to 5, and $R^{20}$ is selected from H and $C_1$-$C_6$ alkyl; or $R^{19}$ and $R^{20}$ together with the nitrogen atom to which they are attached form a heterocyclic or heteroaryl ring having from 5 to 7 ring atoms and optionally containing an additional heteroatom selected from oxygen, nitrogen, and sulfur; and $R^2$ is selected from H, G, acyl, trityl, 4-methoxytrityl, benzoyl, stearoyl, $C_1$-$C_6$ alkyl, $-C(=NH)NH_2$, $-C(O)-R^{23}$, $-C(O)(CH_2)_5NR^{24}C(=NH)NH_2$, $-C(O)(CH_2)_2NHC(O)(CH_2)_5NR^{24}C(=NH)NH_2$, $-C(O)CH(NH_2)(CH_2)_3NHC(=NH)NH_2$, and a moiety of the formula:

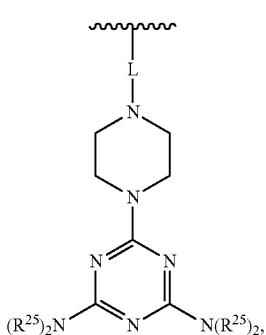

wherein,
- R²³ is of the formula —(O-alkyl)ᵥ-OH wherein v is an integer from 3 to 10 and each of the v alkyl groups is independently selected from $C_2$-$C_6$ alkyl; and
- R²⁴ is selected from H and $C_1$-$C_6$ alkyl;
- s is an integer from 1 to 5;
- L is selected from —C(O)(CH₂)₆C(O)— and —C(O)(CH₂)₂S₂(CH₂)₂C(O)—; and
- each R²⁵ is of the formula —(CH₂)₂OC(O)N(R²⁶)₂ wherein each R²⁶ is of the formula —(CH₂)₆NHC(=NH)NH₂, wherein G is a cell penetrating peptide ("CPP") and linker moiety selected from —C(O)(CH₂)₅NH—CPP, —C(O)(CH₂)₂NH—CPP, —C(O)(CH₂)₂NHC(O)(CH₂)₅NH—CPP, —C(O)CH₂NH—CPP, and:

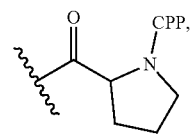

wherein the CPP is attached to the linker moiety by an amide bond at the CPP carboxy terminus, and
wherein G may be present in one occurrence or is absent.

In some embodiments, R² is a moiety of the formula:

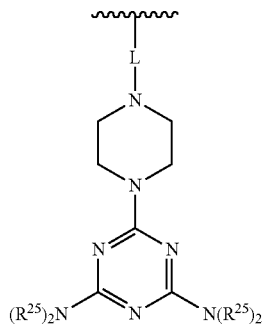

where L is selected from —C(O)(CH₂)₆C(O)— or —C(O)(CH₂)₂S₂(CH₂)₂C(O)—, and
and each R²⁵ is of the formula —(CH₂)₂OC(O)N(R²⁶)₂ wherein each R²⁶ is of the formula —(CH₂)₆NHC(=NH)NH₂. Such moieties are further described in U.S. Pat. No. 7,935,816 incorporated herein by reference in its entirety.

In certain embodiments, R² may comprise either moiety depicted below:

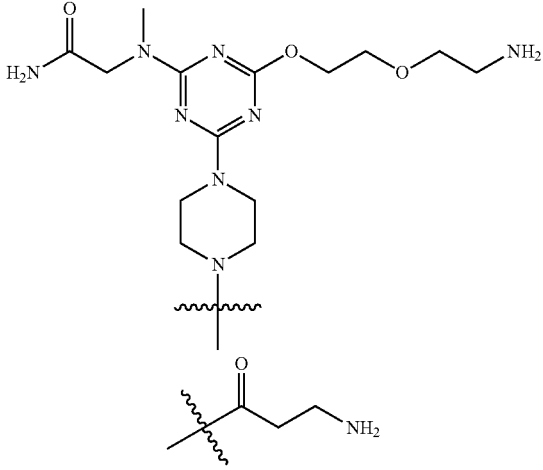

In certain embodiments, each R¹ is —N(CH₃)₂. In some embodiments, about 50-90% of the $R_1$ groups are dimethylamino (i.e. —N(CH₃)₂). In certain embodiments, about 66% of the $R_1$ groups are dimethylamino.

In some non-limiting embodiments, each R¹ is —N(CH₃)₂ and X is selected from uracil (U) or thymine (T).

In some embodiments of the disclosure, $R_1$ may be selected from:

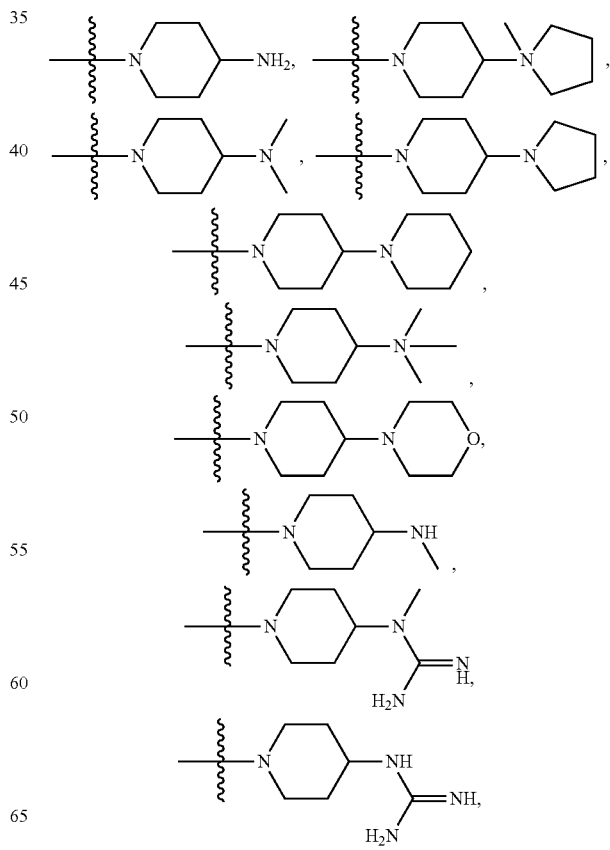

-continued
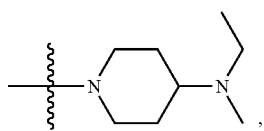
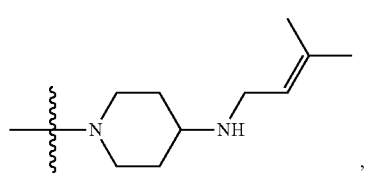
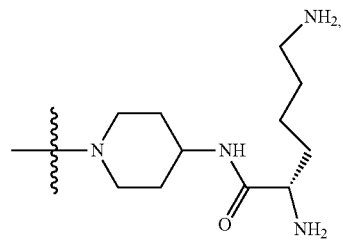
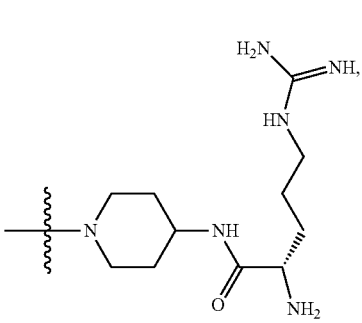
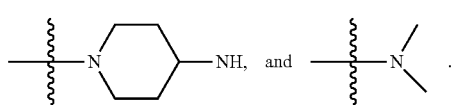
In some embodiments, at least one $R^1$ is:
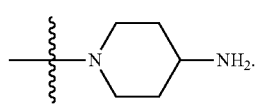
In certain embodiments, T is selected from:
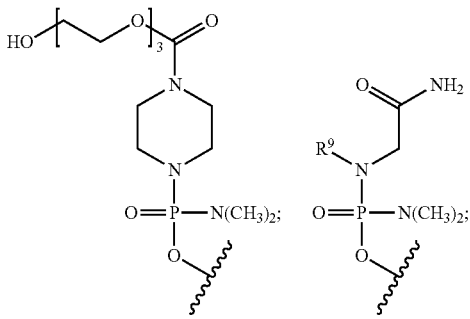
Y is O at each occurrence. In some embodiments, $R^2$ is selected from H, G, acyl, trityl, 4-methoxytrityl, benzoyl, and stearoyl.
In various embodiments, T is selected from:
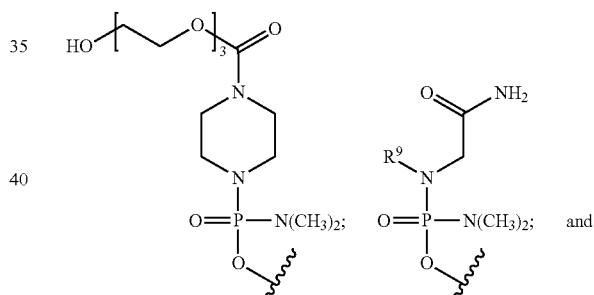
Y is O at each occurrence at each occurrence and $R^2$ is G.
In some embodiments, T is of the formula:
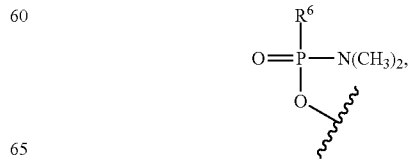

$R^6$ is of the formula:

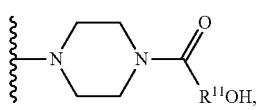

$Y$ is O at each occurrence and $R^2$ is G.

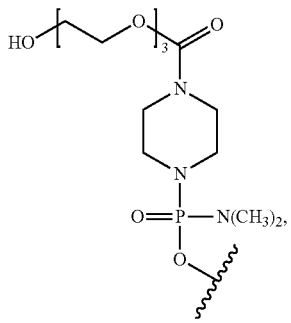

$Y$ is O at each occurrence and $R^2$ is G. In some embodiments, T is of the formula:

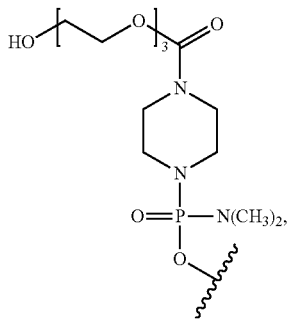

$Y$ is O at each occurrence, each $R^1$ is —$N(CH_3)_2$, and $R^2$ is G.

In certain embodiments, T is of the formula:

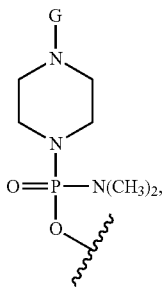

and $Y$ is O at each occurrence. In some embodiments, T is of the formula:

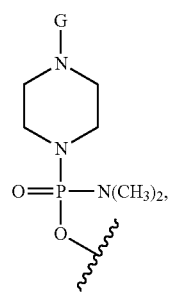

$Y$ is O at each occurrence, each $R^1$ is —$N(CH_3)_2$, and $R^2$ is acetyl.

In certain embodiments, T is of the formula:

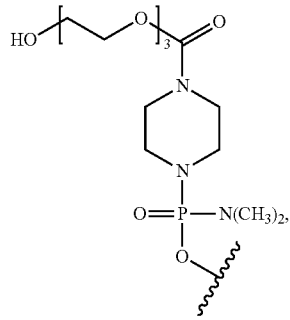

$Y$ is O at each occurrence, each $R^1$ is —$N(CH_3)_2$, and $R^2$ is H.

In some embodiments, $R^2$ is selected from H, acyl, trityl, 4-methoxytrityl, benzoyl, and stearoyl.

In various embodiments, $R^2$ is selected from H or G. In a particular embodiment, $R^2$ is G. In some embodiments, $R^2$ is H or acyl. In some embodiments, each $R^1$ is —$N(CH_3)_2$. In some embodiments, at least one instance of $R^1$ is —$N(CH_3)_2$. In certain embodiments, each instance of $R^1$ is —$N(CH_3)_2$.

In some embodiments, G is of the formula:

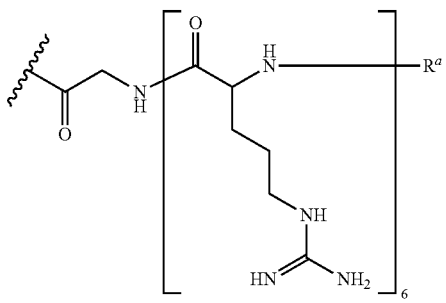

wherein $R^a$ is selected from H, acyl, benzoyl, and stearoyl. In some embodiments, $R^a$ is acetyl.

In certain embodiments, the CPP is of the formula:

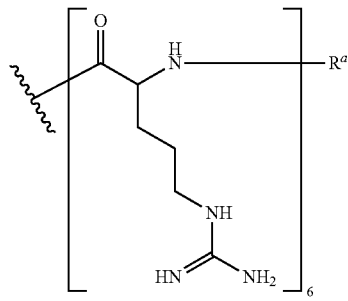

wherein $R^a$ is selected from H, acyl, benzoyl, and stearoyl. In some embodiments, $R^a$ is acetyl.

In another aspect, the antisense oligomer is a compound of formula (Ia):

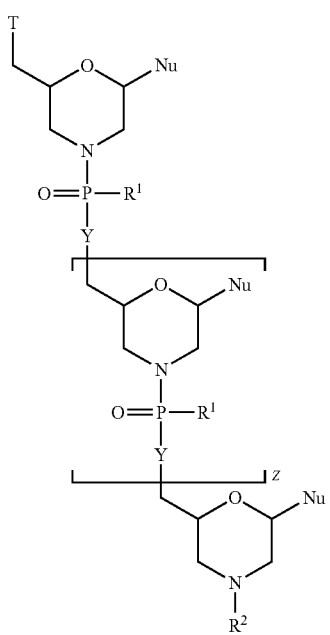

or a pharmaceutically acceptable salt thereof, wherein:
each Nu is a nucleobase which taken together form a targeting sequence;
Z is an integer from about 13 to about 38;
each Y is independently selected from O and $-NR^4$, wherein each $R^4$ is independently selected from H, $C_1-C_6$ alkyl, aralkyl, $-C(=NH)NH_2$, $-C(O)(CH_2)_nNR^5C(=NH)NH_2$, $-C(O)(CH_2)_2NHC(O)(CH_2)_5NR^5C(=NH)NH_2$, and G, wherein $R^5$ is selected from H and $C_1-C_6$ alkyl and n is an integer from 1 to 5;

T is selected from OH and a moiety of the formula:

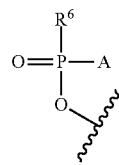

wherein:
A is selected from $-OH$, $-N(R^7)_2$, and $R^1$ wherein:
each $R^7$ is independently selected from H and $C_1-C_6$ alkyl, and
$R^6$ is selected from OH, $-N(R^9)CH_2C(O)NH_2$, and a moiety of the formula:

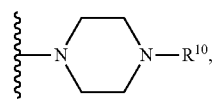

wherein:
$R^9$ is selected from H and $C_1-C_6$ alkyl; and
$R^{10}$ is selected from G, $-C(O)-R^{11}OH$, acyl, trityl, 4-methoxytrityl, $-C(=NH)NH_2$, $-C(O)(CH_2)_mNR^{12}C(=NH)NH_2$, and $-C(O)(CH_2)_2NHC(O)(CH_2)_5NR^{12}C(=NH)NH_2$, wherein:
m is an integer from 1 to 5,
$R^{11}$ is of the formula $-(O\text{-alkyl})_y-$ wherein y is an integer from 3 to 10 and each of the y alkyl groups is independently selected from $C_2-C_6$ alkyl; and
$R^{12}$ is selected from H and $C_1-C_6$ alkyl;
each instance of $R^1$ is independently selected from:
$-N(R^{13})_2$, wherein each $R^{13}$ is independently selected from H and $C_1-C_6$ alkyl;
a moiety of formula (II):

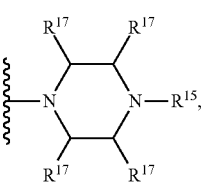

wherein:
$R^{15}$ is selected from H, G, $C_1-C_6$ alkyl, $-C(=NH)NH_2$, $-C(O)(CH_2)_qNR^{18}C(=NH)NH_2$, and $-C(O)(CH_2)_2NHC(O)(CH_2)_5NR^{18}C(=NH)NH_2$, wherein:
$R^{18}$ is selected from H and $C_1-C_6$ alkyl; and
q is an integer from 1 to 5; and
each $R^{17}$ is independently selected from H and methyl; and
a moiety of formula (III):

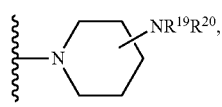

wherein:
R$^{19}$ is selected from H, C$_1$-C$_6$ alkyl, —C(=NH)NH$_2$, —C(O)(CH$_2$)$_r$NR$^{22}$C(=NH)NH$_2$, —C(O)CH(NH$_2$)(CH$_2$)$_3$NHC(=NH)NH$_2$, —C(O)(CH$_2$)$_2$NHC(O)(CH$_2$)$_5$NR$^{22}$C(=NH)NH$_2$, —C(O)CH(NH$_2$)(CH$_2$)$_4$NH$_2$ and G, wherein:
R$^{22}$ is selected from H and C1-C6 alkyl; and
r is an integer from 1 to 5, and
R$^{20}$ is selected from H and C$_1$-C$_6$ alkyl; or
R$^{19}$ and R$^{20}$ together with the nitrogen atom to which they are attached form a heterocyclic or heteroaryl ring having from 5 to 7 ring atoms and optionally containing an additional heteroatom selected from oxygen, nitrogen, and sulfur; and R$^2$ is selected from H, G, acyl, trityl, 4-methoxytrityl, benzoyl, stearoyl, C$_1$-C$_6$ alkyl, —C(=NH)NH$_2$, —C(O)—R$^{23}$, —C(O)(CH$_2$)$_5$NR$^{24}$C(=NH)NH$_2$, —C(O)(CH$_2$)$_2$NHC(O)(CH$_2$)$_5$NR$^{24}$C(=NH)NH$_2$, —C(O)CH(NH$_2$)(CH$_2$)$_3$NHC(=NH)NH$_2$, and a moiety of the formula:

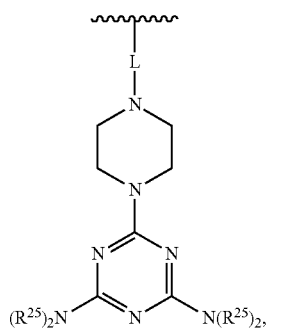

wherein,
R$^{23}$ is of the formula —(O-alkyl)$_v$-OH wherein v is an integer from 3 to 10 and each of the v alkyl groups is independently selected from C$_2$-C$_6$ alkyl; and
R$^{24}$ is selected from H and C$_1$-C$_6$ alkyl;
s is an integer from 1 to 5;
L is selected from —C(O)(CH$_2$)$_6$C(O)— and —C(O)(CH$_2$)$_2$S$_2$(CH$_2$)$_2$C(O)—; and
each R$^{25}$ is of the formula —(CH$_2$)$_2$OC(O)N(R$^{26}$)$_2$ wherein each R$^{26}$ is of the formula —(CH$_2$)$_6$NHC(=NH)NH$_2$,
wherein G is a cell penetrating peptide ("CPP") and linker moiety comprising the formula —C(O)CH$_2$NH—CPP, where CPP is of the formula:

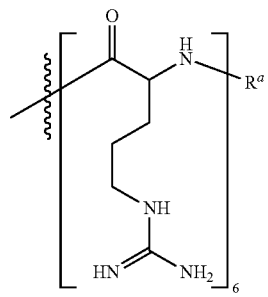

wherein R$^a$ is H or acyl, and
wherein G may be present in one occurrence or is absent.

In certain embodiments, T is selected from:

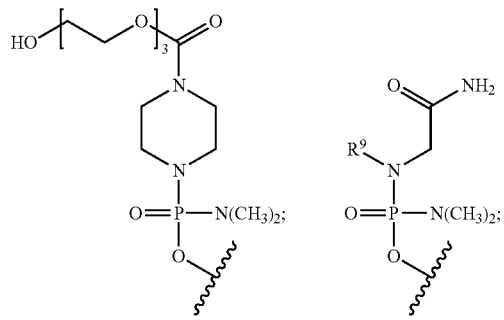

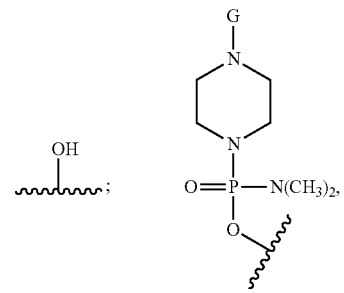

and
Y is O at each occurrence. In some embodiments, R$^2$ is selected from H, G, acyl, trityl, 4-methoxytrityl, benzoyl, and stearoyl.

In various embodiments, T is selected from:

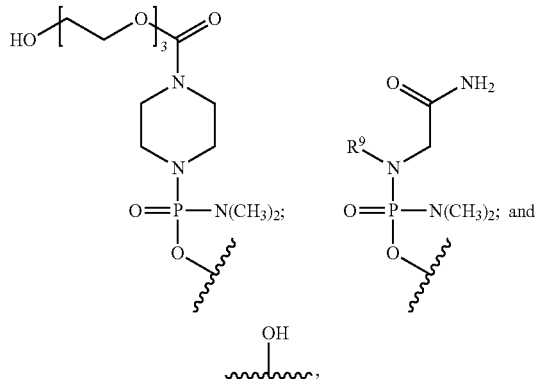

Y is O at each occurrence and R$^2$ is G.

In some embodiments, T is of the formula:

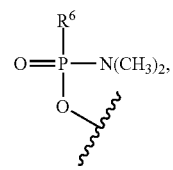

R⁶ is of the formula:

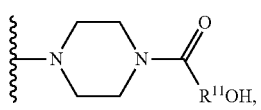

Y is O at each occurrence and R² is G.

In certain embodiments, T is of the formula:

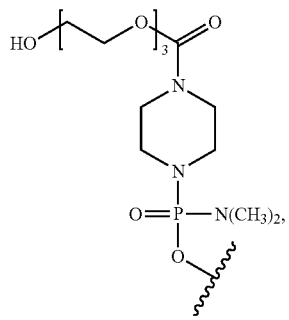

Y is O at each occurrence and R² is G. In some embodiments, T is of the formula:

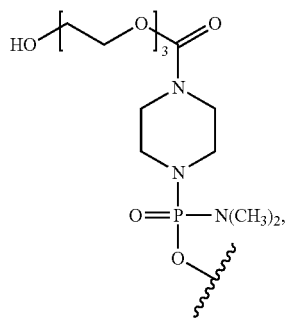

Y is O at each occurrence, each R¹ is —N(CH₃)₂, and R² is G.

In certain embodiments, T is of the formula:

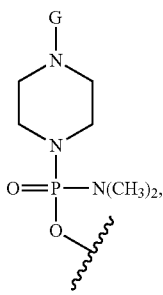

and Y is O at each occurrence. In some embodiments, T is of the formula:

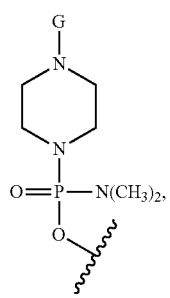

Y is O at each occurrence, each R¹ is —N(CH₃)₂, and R² is acetyl.

In certain embodiments, T is of the formula: Y

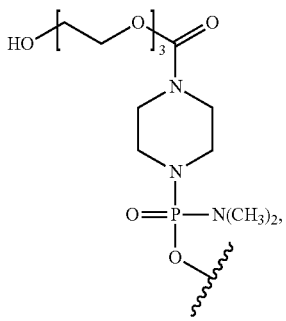

is O at each occurrence, each R¹ is —N(CH₃)₂, and R² is H.

In some embodiments, R² is selected from H, acyl, trityl, 4-methoxytrityl, benzoyl, and stearoyl.

In various embodiments, R² is selected from H or G. In a particular embodiment, R² is G. In some embodiments, R² is H or acyl. In some embodiments, each R¹ is —N(CH₃)₂. In some embodiments, at least one instance of R¹ is —N(CH₃)₂. In certain embodiments, each instance of R¹ is —N(CH₃)₂.

In some embodiments, Rᵃ is acetyl.

In embodiments including, for example, embodiments of the antisense oligomers of formula (I) and (Ia), the targeting sequence is complementary to a target region within intron 1 of a pre-mRNA of the human alpha glucosidase (GAA) gene. In embodiments including, for example, embodiments of the antisense oligomers of formula (I) and (Ia), the targeting sequence is complementary to a target region within intron 1 of a pre-mRNA of the human alpha glucosidase (GAA) gene, wherein the target region comprises at least one additional nucleobase compared to the targeting sequence, wherein the at least one additional nucleobase has no complementary nucleobase in the targeting sequence, and wherein the at least one additional nucleobase is internal to the target region.

In embodiments, a sequence with 100% complementarity is selected and one or more nucleobases is removed (or alternately are synthesized with one or more missing nucleobases) so that the resulting sequence has one or more missing nucleobases than its natural complement in the target region. With the exception of the portion where one or more nucleobases are removed, it is contemplated that the remaining portions are 100% complementary. However, it is within the scope of this invention that decreased levels of complementarity could be present.

In certain embodiments, the antisense oligomer of the disclosure is a compound of formula (IVa):

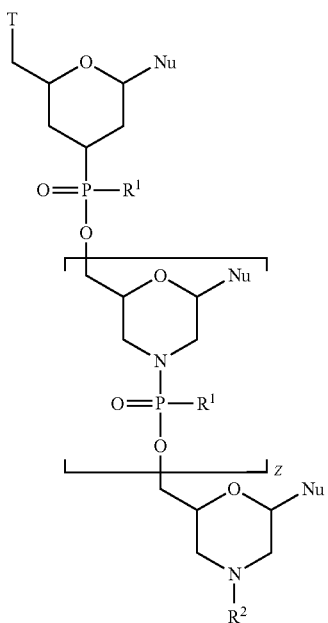

(IVa)

or a pharmaceutically acceptable salt thereof, wherein:
each Nu is a nucleobase which taken together forms a targeting sequence;
Z is an integer from 8 to 38;
T is selected from OH and a moiety of the formula:

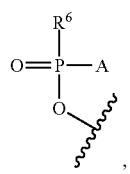

wherein:
A is selected from —OH, —N($R^7$)$_2$$R^8$, and $R^1$ wherein:
each $R^7$ is independently selected from H and $C_1$-$C_6$ alkyl, and
$R^8$ is selected from an electron pair and H, and
$R^6$ is selected from OH, —N($R^9$)CH$_2$C(O)NH$_2$, and a moiety of the formula:

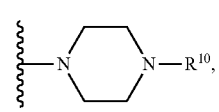

wherein:
$R^9$ is selected from H and $C_1$-$C_6$ alkyl; and
$R^{10}$ is selected from —C(O)—$R^{11}$OH, acyl, trityl, 4-methoxytrityl, —C(=NH)NH$_2$, —C(O)(CH$_2$)$_m$NR$^{12}$C(=NH)NH$_2$, and —C(O)(CH$_2$)$_2$NHC(O)(CH$_2$)$_5$NR$^{12}$C(=NH)NH$_2$,
wherein:
m is an integer from 1 to 5,
$R^{11}$ is of the formula —(O-alkyl)$_y$- wherein y is an integer from 3 to 10 and
each of the y alkyl groups is independently selected from $C_2$-$C_6$ alkyl; and
$R^{12}$ is selected from H and $C_1$-$C_6$ alkyl;
each instance of $R^1$ is independently —N($R^{13}$)$_2$$R^{14}$, wherein each $R^{13}$ is independently selected from H and $C_1$-$C_6$ alkyl, and $R^m$ is selected from an electron pair and H; and $R^2$ is selected from H, acyl, trityl, 4-methoxytrityl, benzoyl, stearoyl, and $C_1$-$C_6$ alkyl.

In certain embodiments, T is selected from:

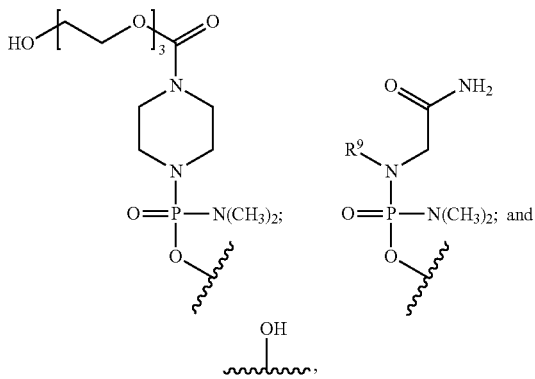

and
Y is O at each occurrence. In some embodiments, $R^2$ is selected from H, acyl, trityl, 4-methoxytrityl, benzoyl, and stearoyl.

In various embodiments, T is selected from:

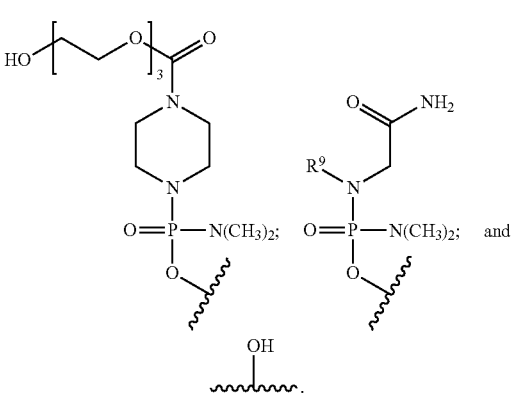

In some embodiments, T is of the formula:

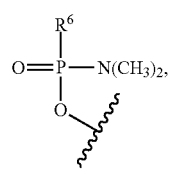

and $R^6$ is of the formula:

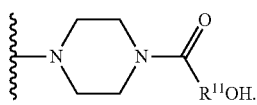

In certain embodiments, T is of the formula:

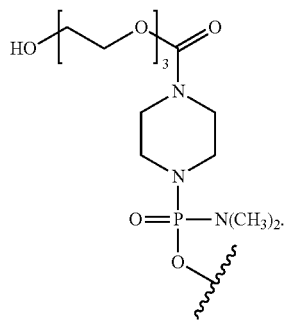

In some embodiments, $R^2$ is H, trityl, or acyl. In some embodiments, at least one instance of $R^1$ is $-N(CH_3)_2$. In some embodiments, each $R^1$ is $-N(CH_3)_2$.

In certain embodiments, the antisense oligomer of the disclosure is a compound of formula (IVb):

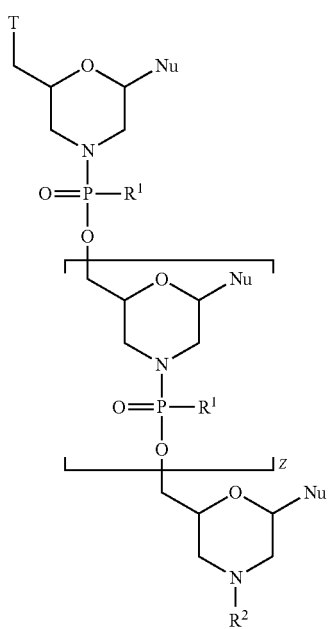

(IVb)

or a pharmaceutically acceptable salt thereof, where:

each Nu is a nucleobase which taken together forms a targeting sequence;

Z is an integer from 8 to 38;

T is selected from a moiety of the formula:

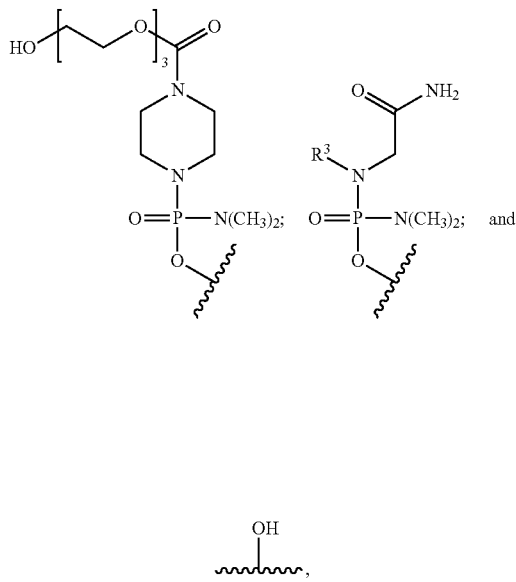

wherein $R^3$ is selected from H and $C_1$-$C_6$ alkyl;

each instance of $R^1$ is independently $-N(R^4)_2$, wherein each $R^4$ is independently selected from H and $C_1$-$C_6$ alkyl; and $R^2$ is selected from H, acyl, trityl, 4-methoxytrityl, benzoyl, stearoyl, and $C_1$-$C_6$ alkyl.

In various embodiments, $R^2$ is selected from H or acyl. In some embodiments, $R^2$ is H.

In certain embodiments; T is of the formula:

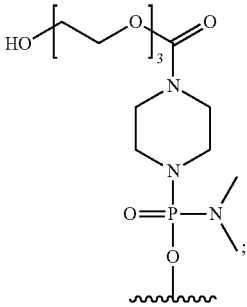

and $R^2$ is hydrogen.

In certain embodiments, the antisense oligomer of the disclosure is a compound of formula (IVc):

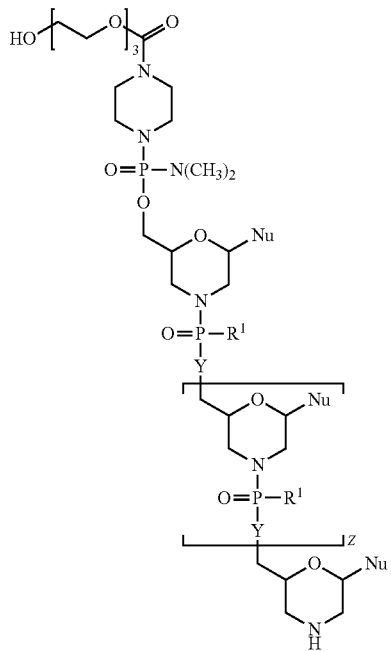

(IVc)

or a pharmaceutically acceptable salt thereof wherein:
  each Nu is a nucleobase which taken together form a targeting sequence;
  Z is an integer from 8 to 38;
  each Y is O;
  each R¹ is independently selected from the group consisting of:

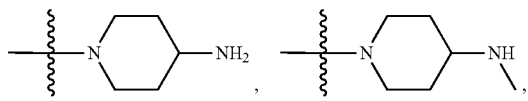

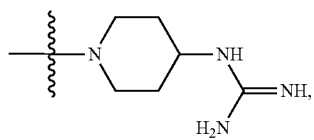

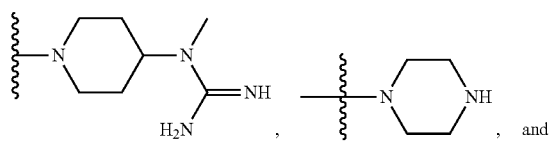

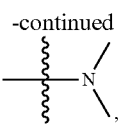

wherein at least one R¹ is —N(CH₃)₂.

In some embodiments, X is selected from uracil (U) or thymine (T). In some embodiments, each R¹ is —N(CH₃)₂.

In certain embodiments, the antisense oligomer is a compound of formula (V):

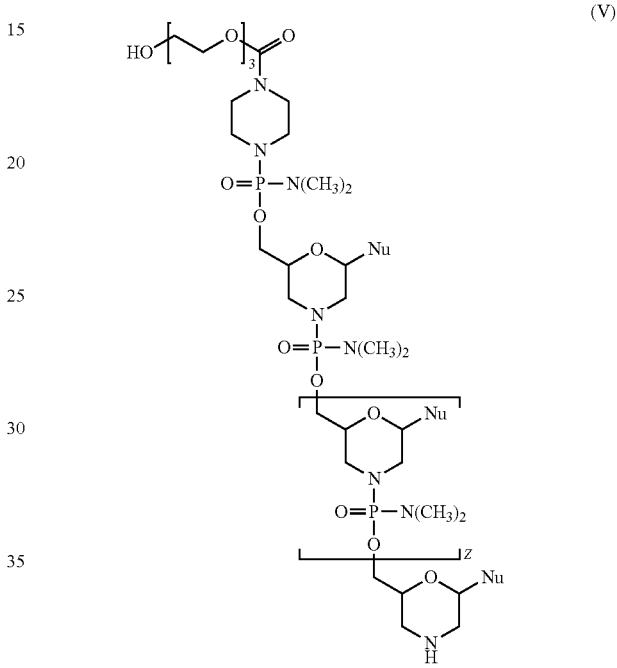

(V)

or a pharmaceutically acceptable salt thereof, wherein:
  each Nu is a nucleobase which taken together form a targeting sequence; and
  Z is an integer from 8 to 38.

In some embodiments including, for example, embodiments of the antisense oligomers of formula (IVa), (IVb), (IVc) and (V), the targeting sequence is complementary to a target region that comprises an exon target associated with Duchenne muscular dystrophy. In certain embodiments, the targeting sequence is complementary to a target sequence that comprises exon 44 in the processing of human dystrophin pre-processed mRNA. Further, in certain embodiments, a sequence with 100% complementarity is selected and one or more nucleobases is removed (or alternately are synthesized with one or more missing nucleobases) so that the resulting sequence has one or more missing nucleobases than its natural complement in the target region. With the exception of the portion where one or more nucleobases are removed, it is contemplated that the remaining portions are 100% complementary. However, it is within the scope of this invention that decreased levels of complementarity could be present. In embodiments, at least one nucleobase is removed when the targeting sequence would otherwise include a string of three or four of more identical contiguous nucleobases or a biological palindrome sequence.

In some embodiments including, for example, embodiments of the antisense oligomers of formula (IVa), (IVb), (IVc) and (V), the targeting sequence is complementary to a target region that comprises an exon target associated with spinal muscular atrophy. In certain embodiments, the targeting sequence is complementary to a target sequence that comprises a region adjacent to exon 7 in the processing of human SMN2 pre-processed mRNA. Further, in certain embodiments, a sequence with 100% complementarity is selected and one or more nucleobases is removed (or alternately are synthesized with one or more missing nucleobases) so that the resulting sequence has one or more missing nucleobases than its natural complement in the target region. With the exception of the portion where one or more nucleobases are removed, it is contemplated that the remaining portions are 100% complementary. However, it is within the scope of this invention that decreased levels of complementarity could be present. In embodiments, at least one nucleobase is removed when the targeting sequence would otherwise include a string of three or four of more identical contiguous nucleobases or a biological palindrome sequence.

In some embodiments including, for example, embodiments of the antisense oligomers of formula (IVa), (IVb), (IVc) and (V), the targeting sequence is complementary to a target region within intron 1 of a pre-mRNA of the human alpha glucosidase (GAA) gene. In various embodiments including, for example, embodiments of the antisense oligomers of formula (IVa), (IVb), (IVc) and (V), the targeting sequence is complementary to a target region associated with exon 2 of a pre-mRNA of the human alpha glucosidase (GAA) gene, wherein the target region comprises at least one additional nucleobase compared to the targeting sequence, wherein the at least one additional nucleobase has no complementary nucleobase in the targeting sequence, and wherein the at least one additional nucleobase is internal to the target region. Further, in certain embodiments, a sequence with 100% complementarity is selected and one or more nucleobases is removed (or alternately are synthesized with one or more missing nucleobases) so that the resulting sequence has one or more missing nucleobases than its natural complement in the target region. With the exception of the portion where one or more nucleobases are removed, it is contemplated that the remaining portions are 100% complementary. However, it is within the scope of this invention that decreased levels of complementarity could be present. In embodiments, at least one nucleobase is removed when the targeting sequence would otherwise include a string of three or four of more identical contiguous nucleobases or a biological palindrome sequence.

In various aspects, the antisense oligomers comprise the deletion sequence of any one of SEQ ID NOs: 1-128, wherein at least one nucleobase in any one of SEQ ID NOs: 1-128 has been deleted. In various embodiments, the oligonucleotide comprises CTCCAACATCAAGGAAGATGGCATTTCTAG (SEQ ID NO: 69; Eteplirsen); GTTGCCTCCGGTTCTGAAGGTGTTC (SEQ ID NO: 70; Golodirsen); or CAATGCCATCCTGGAGTTCCTG (SEQ ID NO: 71; Casimersen). In various embodiments, the deletion sequence comprises any one of SEQ ID NOs: 69-71, wherein at least one nucleobase in any one of SEQ ID NOs: 72-74 has been deleted. In embodiments, the at least one nucleobase that has been deleted is internal to the sequence of any one of SEQ ID NOs: 69-71.

In certain embodiments, the antisense oligomer is a compound of formula (VI):

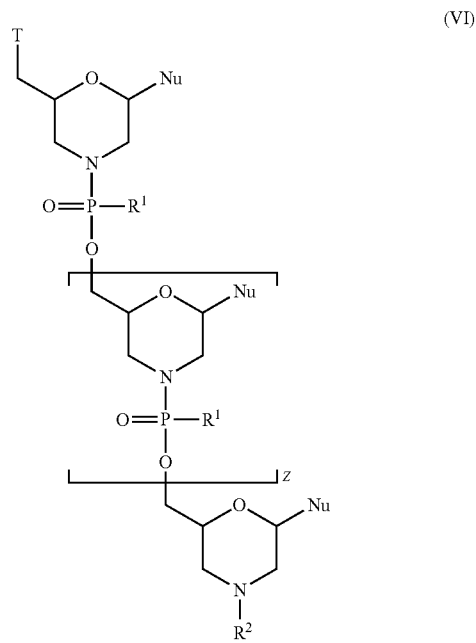

(VI)

or a pharmaceutically acceptable salt thereof, where each Nu is a nucleobase which taken together forms a targeting sequence;

Z is an integer from 8 to 38;

T is selected from:

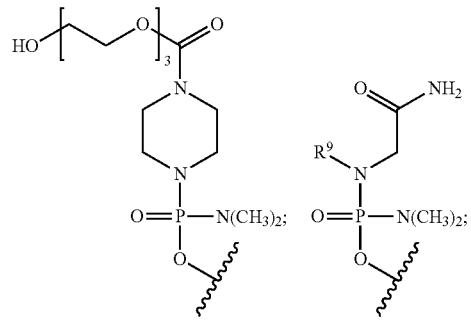

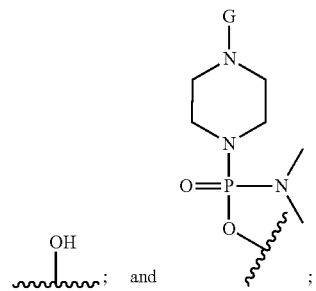

each R¹ is independently selected from the group consisting of:

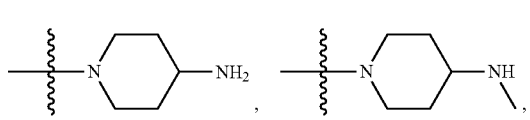

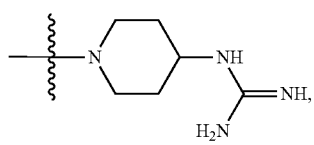

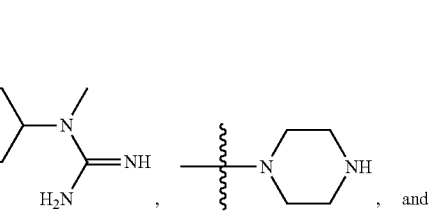

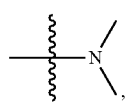

R² is selected from H, G, acyl, trityl, 4-methoxytrityl, benzoyl, and stearoyl, wherein G is a cell penetrating peptide ("CPP") and linker moiety selected from —C(O)(CH₂)₅NH—CPP, —C(O)(CH₂)₂NH—CPP, —C(O)(CH₂)₂NHC(O)(CH₂)₅NH—CPP, —C(O)CH₂NH—CPP, and:

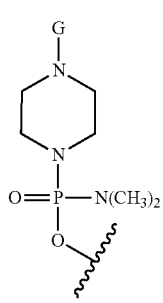

wherein the CPP is attached to the linker moiety by an amide bond at the CPP carboxy terminus, and wherein T is

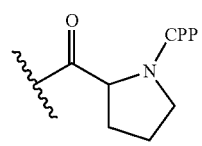

or R² is G.

In certain embodiments, T is of the formula:

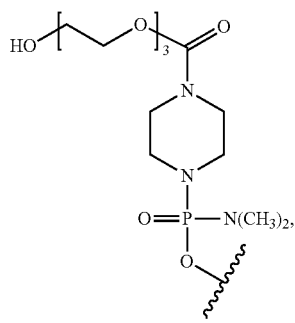

and R² is G. In certain embodiments, at least one occurrence of R¹ is —N(CH₃)₂. In some embodiments, each occurrence of R¹ is —N(CH₃)₂. In some embodiments, T is of the formula:

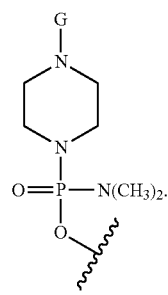

In certain embodiments, at least one occurrence of R¹ is —N(CH₃)₂. In some embodiments, each occurrence of R¹ is —N(CH₃)₂.

In some embodiments, T is of the formula:

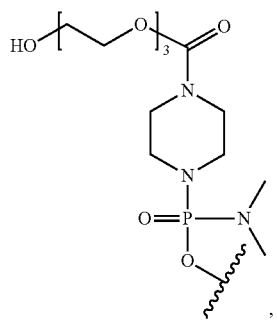

R² is G, and each occurrence of R¹ is —N(CH₃)₂.

In certain embodiments, R² is selected from H, acetyl, trityl, 4-methoxytrityl, benzoyl, and stearoyl and T is of the formula:

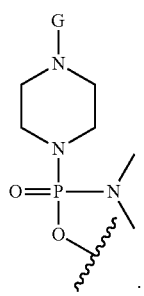

In various embodiments, R² is acetyl. In certain embodiments, at least one occurrence of R¹ is —N(CH₃)₂. In some embodiments, each occurrence of R¹ is —N(CH₃)₂.

In various embodiments, R² is selected from H, acyl, trityl, 4-methoxytrityl, benzoyl, and stearoyl.

In certain embodiments, R2 is acetyl, T is of the formula:

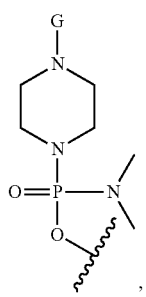

and each occurrence of R¹ is —N(CH₃)₂.

In some embodiments, wherein G is of the formula:

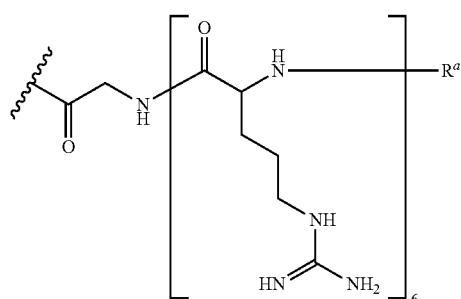

wherein $R^a$ is selected from H, acyl, benzoyl, and stearoyl.
In some embodiments, $R^a$ is acetyl.

In some embodiments, the CPP is of the formula:

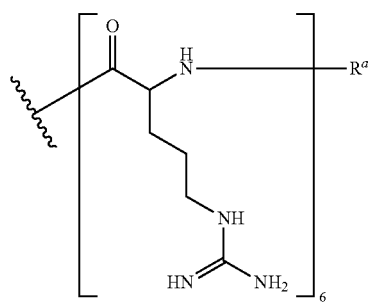

wherein $R^a$ is selected from H, acyl, benzoyl, and stearoyl.
In some embodiments, $R^a$ is acetyl.

In certain embodiments, the antisense oligomer is a compound of formula (VII):

(VII)

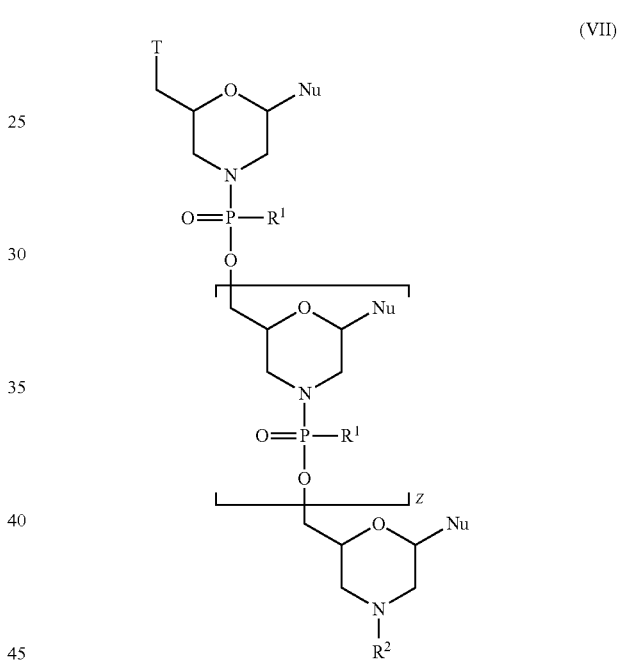

or a pharmaceutically acceptable salt thereof,
where each Nu is a nucleobase which taken together forms a targeting sequence;
Z is an integer from 8 to 38;
T is selected from:

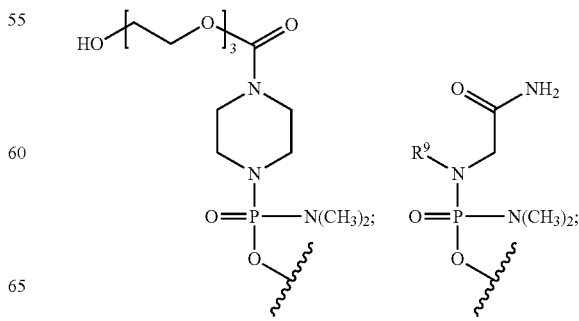

-continued

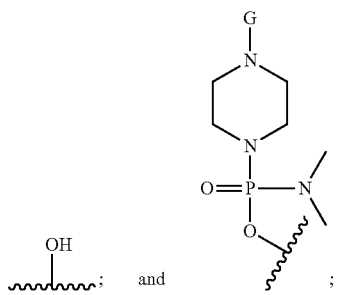

each R¹ is —N(R⁴)₂ wherein each R⁴ is independently $C_1$-$C_6$ alkyl; and

R² is selected from H, G, acyl, trityl, 4-methoxytrityl, benzoyl, and stearoyl, wherein G is a cell penetrating peptide ("CPP") and linker moiety selected from —C(O)(CH₂)₅NH—CPP, —C(O)(CH₂)₂NH—CPP, —C(O)(CH₂)₂NHC(O)(CH₂)₅NH—CPP, —C(O)CH₂NH—CPP, and:

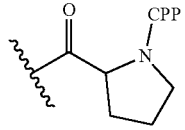

wherein the CPP is attached to the linker moiety by an amide bond at the CPP carboxy terminus, and
wherein T is

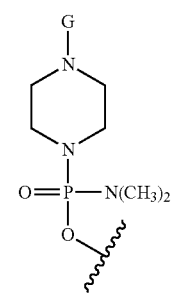

or R² is G.

In some embodiments, at least one instance of R¹ is —N(CH₃)₂. In certain embodiments, each instance of R¹ is —N(CH₃)₂.

In certain embodiments, T is of the formula:

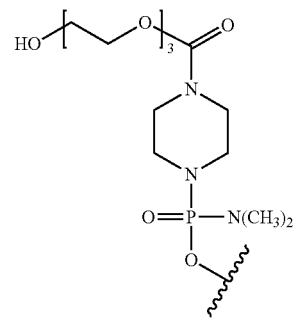

and R² is G. In some embodiments, at least one instance of R¹ is —N(CH₃)₂. In certain embodiments, each instance of R¹ is —N(CH₃)₂.

In various embodiments, G is of the formula:

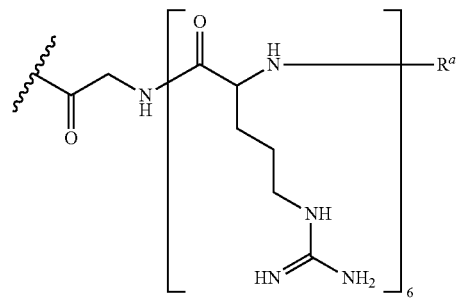

wherein Rᵃ is selected from H, acyl, benzoyl, and stearoyl. In some embodiments, Rᵃ is acetyl.

In certain embodiments, the CPP is of the formula:

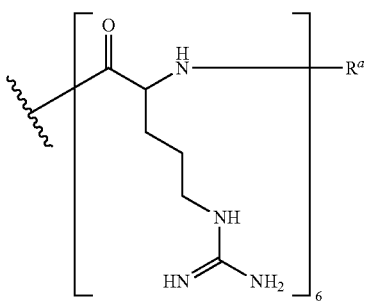

wherein Rᵃ is selected from H, acetyl, benzoyl, and stearoyl. In some embodiments, Rᵃ is acetyl.

In certain embodiments, the antisense oligomer is a compound of formula (VIIa):

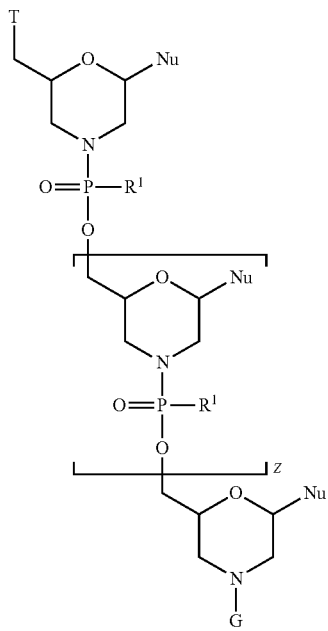

(VIIa)

or a pharmaceutically acceptable salt thereof,
where each Nu is a nucleobase which taken together forms a targeting sequence;
Z is an integer from 8 to 38;
T is selected from:

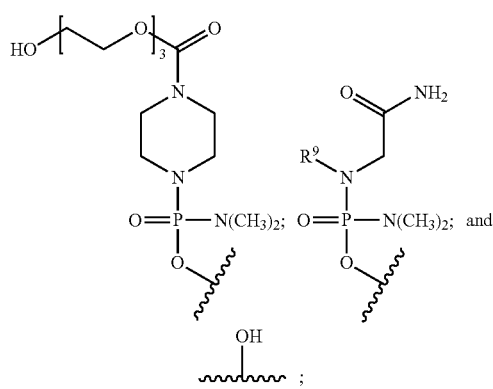

each instance of $R^1$ is $-N(R^4)_2$ wherein each $R^4$ is independently $C_1$-$C_6$ alkyl; and
G is a cell penetrating peptide ("CPP") and linker moiety selected from $-C(O)(CH_2)_5NH$—CPP, $-C(O)(CH_2)_2NH$—CPP, $-C(O)(CH_2)_2NHC(O)(CH_2)_5NH$—CPP, $-C(O)CH_2NH$—CPP, and:

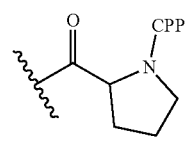

wherein the CPP is attached to the linker moiety by an amide bond at the CPP carboxy terminus.

In some embodiments, at least one instance of $R^1$ is $-N(CH_3)_2$. In certain embodiments, each instance of $R^1$ is $-N(CH_3)_2$.

In some embodiments, G is of the formula:

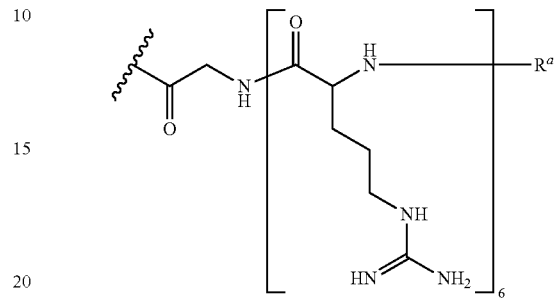

wherein $R^a$ is selected from H, acyl, benzoyl, and stearoyl. In some embodiments, $R^a$ is acetyl.

In various embodiments, each instance of $R^1$ is $-N(CH_3)_2$, G is of the formula:

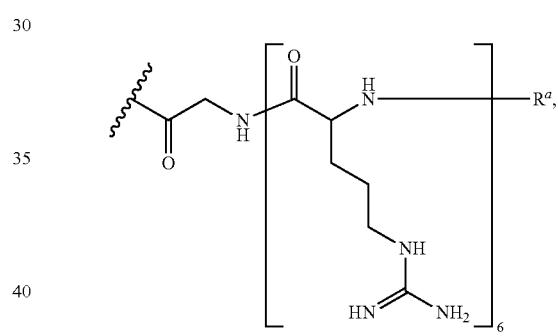

and
$R^a$ is acetyl.

In certain embodiments, the CPP is of the formula:

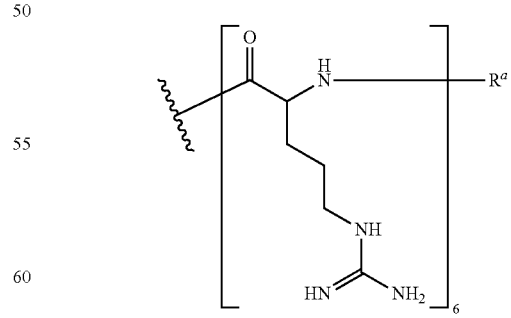

wherein $R^a$ is selected from H, acyl, benzoyl, and stearoyl. In some embodiments, $R^a$ is acetyl. In various embodiments, each instance of $R^1$ is $-N(CH_3)_2$, the CPP is of the formula:

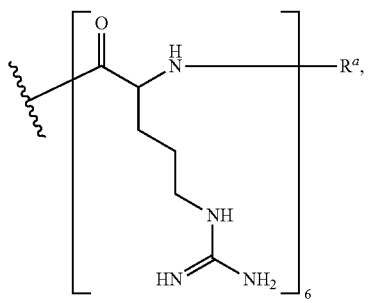

and

R$^a$ is acetyl.

In various aspects, an antisense oligonucleotide of the disclosure includes a compound of formula (VIIb):

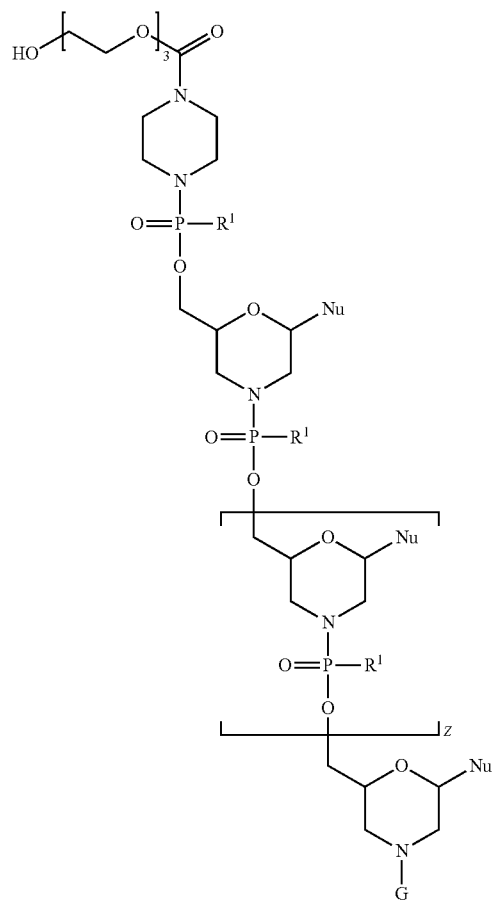

(VIIb)

or a pharmaceutically acceptable salt thereof, wherein:

where each Nu is a nucleobase which taken together forms a targeting sequence;

Z is an integer from 8 to 38;

each instance of R$^1$ is —N(R$^4$)$_2$ wherein each R$^4$ is independently C$_1$-C$_6$ alkyl; and G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, —C(O)CH$_2$NH—CPP, and:

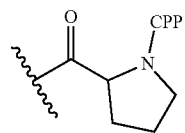

wherein the CPP is attached to the linker moiety by an amide bond at the CPP carboxy terminus.

In some embodiments, at least one instance of R$^1$ is —N(CH$_3$)$_2$. In certain embodiments, each instance of R$^1$ is —N(CH$_3$)$_2$.

In some embodiments, G is of the formula:

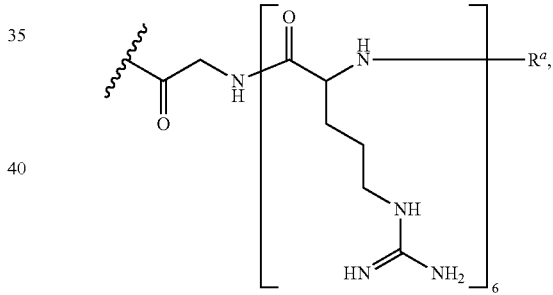

wherein R$^a$ is selected from H, acyl, benzoyl, and stearoyl. In some embodiments, R$^a$ is acetyl.

In various embodiments, each instance of R1 is —N(CH3)2, G is of the formula:

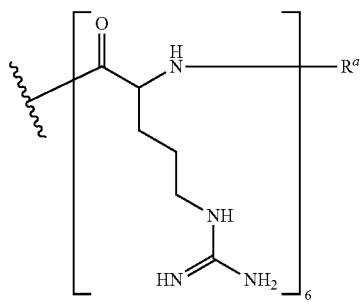

and

R$^a$ is acetyl.

In certain embodiments, the CPP is of the formula:

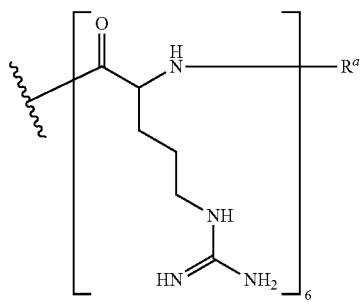

wherein R$^a$ is selected from H, acyl, benzoyl, and stearoyl. In some embodiments, R$^a$ is acetyl. In various embodiments, each instance of R$^1$ is —N(CH$_3$)$_2$, the CPP is of the formula:

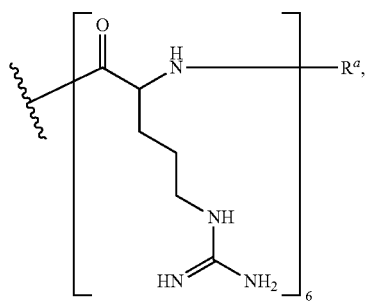

and $R^a$ is acetyl.

In various aspects, an antisense oligonucleotide of the disclosure includes a compound of formula (VIIc):

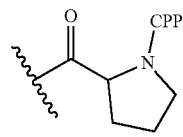

wherein the CPP is attached to the linker moiety by an amide bond at the CPP carboxy terminus.

In some embodiments, G is of the formula:

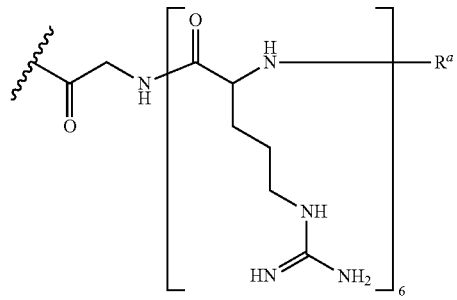

wherein $R^a$ is selected from H, acyl, benzoyl, and stearoyl. In some embodiments, $R^a$ is acetyl.

In various embodiments, G is of the formula:

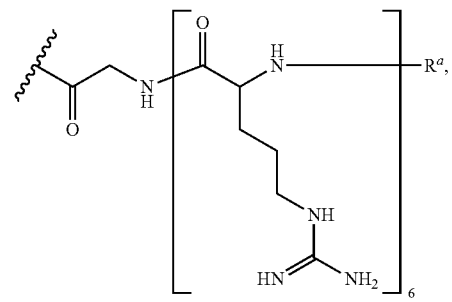

and $R^a$ is acetyl.

In certain embodiments, the CPP is of the formula:

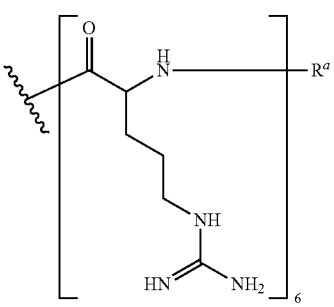

or a pharmaceutically acceptable salt thereof, wherein:

where each Nu is a nucleobase which taken together forms a targeting sequence;

Z is an integer from 8 to 38; and

G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, —C(O)CH$_2$NH—CPP, and:

wherein $R^a$ is selected from H, acyl, benzoyl, and stearoyl. In some embodiments, $R^a$ is acetyl. In various embodiments, the CPP is of the formula:

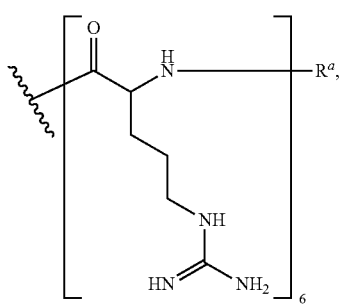

and

R<sup>a</sup> is acetyl.

In various aspects, an antisense oligomer of the disclosure is a compound of formula (VIId):

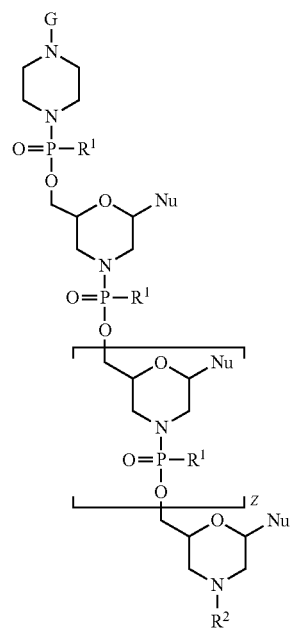

(VIId)

wherein:

each Nu is a nucleobase which taken together forms a targeting sequence;

Z is an integer from 8 to 38;

each instance of $R^1$ is $-N(R^4)_2$ wherein each $R^4$ is independently $C_1$-$C_6$ alkyl; and $R^2$ is selected from H, trityl, 4-methoxytrityl, acetyl, benzoyl, and stearoyl; and G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, —C(O)CH$_2$NH—CPP, and:

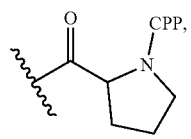

wherein the CPP is attached to the linker moiety by an amide bond at the CPP carboxy terminus.

In some embodiments, at least one instance of R1 is —N(CH$_3$)$_2$. In certain embodiments, each instance of $R^1$ is —N(CH$_3$)$_2$.

In some embodiments, G is of the formula:

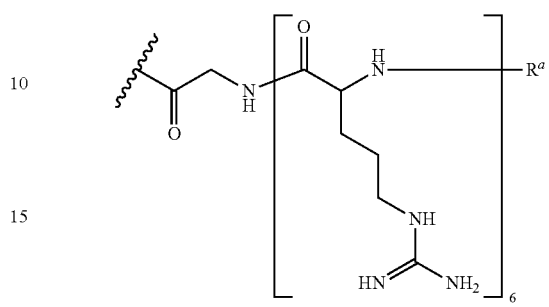

wherein $R^a$ is selected from H, acyl, benzoyl, and stearoyl. In some embodiments, $R^a$ is acetyl.

In various embodiments, each instance of $R^1$ is —N(CH$_3$)$_2$, G is of the formula:

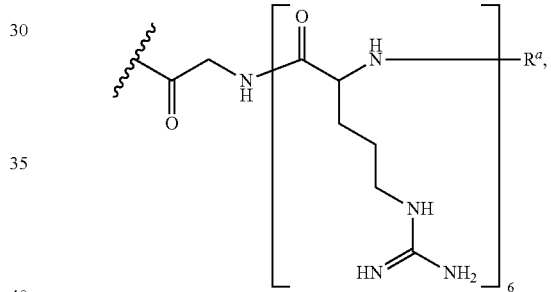

and $R^a$ is acetyl.

In certain embodiments, the CPP is of the formula:

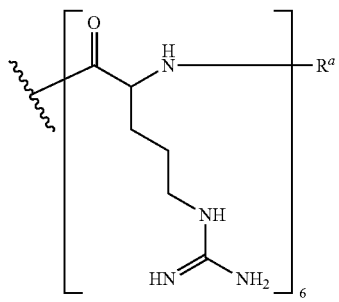

wherein $R^a$ is selected from H, acyl, benzoyl, and stearoyl. In some embodiments, $R^a$ is acetyl. In various embodiments, each instance of $R^1$ is —N(CH$_3$)$_2$, the CPP is of the formula:

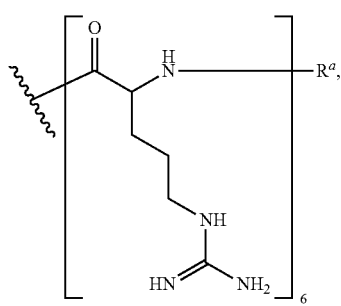

and
R$^a$ is acetyl.

In various aspects, an antisense oligonucleotide of the disclosure includes a compound of formula (VIIe):

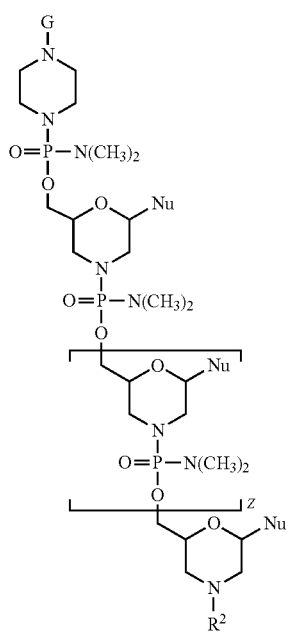

(VIIe)

or a pharmaceutically acceptable salt thereof, wherein:

each Nu is a nucleobase which taken together forms a targeting sequence;

Z is an integer from 8 to 38;

R$^2$ is selected from H, trityl, 4-methoxytrityl, acetyl, benzoyl, and stearoyl; and G is a cell penetrating peptide ("CPP") and linker moiety selected from —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, —C(O)CH$_2$NH—CPP, and:

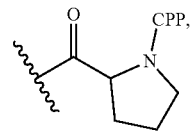

wherein the CPP is attached to the linker moiety by an amide bond at the CPP carboxy terminus.

In some embodiments, G is of the formula:

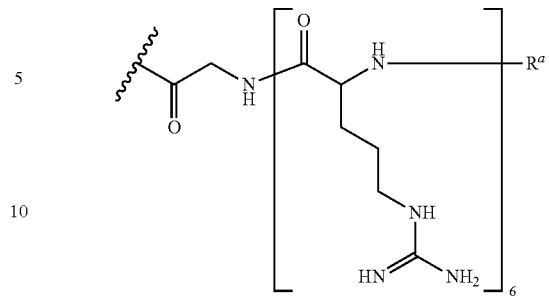

wherein R$^a$ is selected from H, acyl, benzoyl, and stearoyl. In some embodiments, R$^a$ is acetyl.

In various embodiments, G is of the formula:

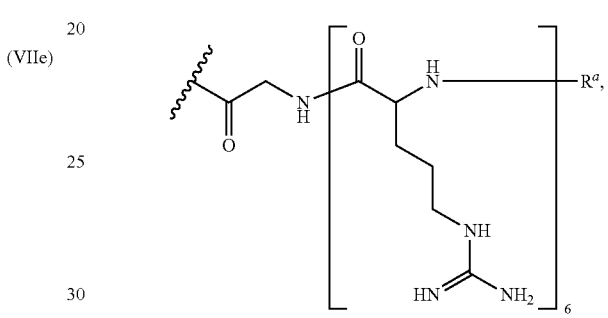

and
R$^a$ is acetyl.

In certain embodiments, the CPP is of the formula:

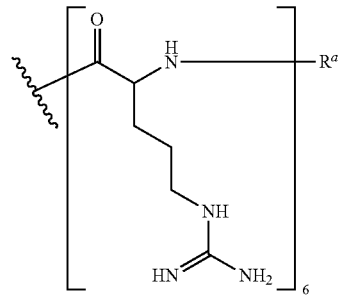

wherein R$^a$ is selected from H, acyl, benzoyl, and stearoyl. In some embodiments, R$^a$ is acetyl. In various embodiments, the CPP is of the formula:

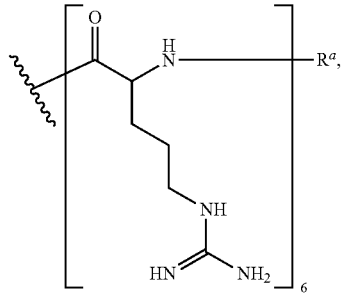

and
R$^a$ is acetyl.

In various embodiments including, for example, embodiments of the antisense oligomers of formula (VI), (VII), (VIIa), (VIIb), (VIIc), (VIId), (VIIe), and (VIII), the targeting sequence is complementary to a target region that comprises an exon target associated with Duchenne muscular dystrophy. In certain embodiments, the targeting sequence is complementary to a target sequence that comprises exon 44 in the processing of human dystrophin pre-processed mRNA. Further, in certain embodiments, a sequence with 100% complementarity is selected and one or more nucleobases is removed (or alternately are synthesized with one or more missing nucleobases) so that the resulting sequence has one or more missing nucleobases than its natural complement in the target region. With the exception of the portion where one or more nucleobases are removed, it is contemplated that the remaining portions are 100% complementary. However, it is within the scope of this invention that decreased levels of complementarity could be present. In embodiments, at least one nucleobase is removed when the targeting sequence would otherwise include a string of three or four of more identical contiguous nucleobases or a biological palindrome sequence.

In various embodiments including, for example, embodiments of the antisense oligomers of formula (VI), (VII), (VIIa), (VIIb), (VIIc), (VIId), (VIIe), and (VIII), the targeting sequence is complementary to a target region that comprises an exon target associated with spinal muscular atrophy. In certain embodiments, the targeting sequence is complementary to a target sequence that comprises a region adjacent to exon 7 in the processing of human SMN2 pre-processed mRNA. Further, in certain embodiments, a sequence with 100% complementarity is selected and one or more nucleobases is removed (or alternately are synthesized with one or more missing nucleobases) so that the resulting sequence has one or more missing nucleobases than its natural complement in the target region. With the exception of the portion where one or more nucleobases are removed, it is contemplated that the remaining portions are 100% complementary. However, it is within the scope of this invention that decreased levels of complementarity could be present. In embodiments, at least one nucleobase is removed when the targeting sequence would otherwise include a string of three or four of more identical contiguous nucleobases or a biological palindrome sequence.

In various embodiments including, for example, embodiments of the antisense oligomers of formula (VI), (VII), (VIIa), (VIIb), (VIIc), (VIId), (VIIe), and (VIII), the targeting sequence is complementary to a target region within intron 1 of a pre-mRNA of the human alpha glucosidase (GAA) gene. In various embodiments including, for example, embodiments of the antisense oligomers of formula (VI), (VII), (VIIa), (VIIb), (VIIc), (VIId), (VIIe), and (VIII), the targeting sequence is complementary to a target region associated with exon 2 of a pre-mRNA of the human alpha glucosidase (GAA) gene, wherein the target region comprises at least one additional nucleobase compared to the targeting sequence, wherein the at least one additional nucleobase has no complementary nucleobase in the targeting sequence, and wherein the at least one additional nucleobase is internal to the target region. Further, in certain embodiments, a sequence with 100% complementarity is selected and one or more nucleobases is removed (or alternately are synthesized with one or more missing nucleobases) so that the resulting sequence has one or more missing nucleobases than its natural complement in the target region. With the exception of the portion where one or more nucleobases are removed, it is contemplated that the remaining portions are 100% complementary. However, it is within the scope of this invention that decreased levels of complementarity could be present. In embodiments, at least one nucleobase is removed when the targeting sequence would otherwise include a string of three or four of more identical contiguous nucleobases or a biological palindrome sequence.

In various aspects, the antisense oligomers comprise the deletion sequence of any one of SEQ ID NOs: 1-128, wherein at least one nucleobase in any one of SEQ ID NOs: 1-128 has been deleted. In various embodiments, the oligonucleotide comprises CTCCAACATCAAGGAAGATGG-CATTTCTAG (SEQ ID NO: 69; Eteplirsen); GTTGCCTCCGGTTCTGAAGGTGTTC (SEQ ID NO: 70; Golodirsen); or CAATGCCATCCTGGAGTTCCTG (SEQ ID NO: 71; Casimersen).

In some embodiments of any of the antisense oligomers, methods, or compositions described herein, Z is an integer from 8 to 28, from 15 to 38, 15 to 28, 8 to 25, from 15 to 25, from 10 to 38, from 10 to 25, from 12 to 38, from 12 to 25, from 14 to 38, or from 14 to 25. In some embodiments of any of the antisense oligomers, methods, or compositions described herein, Z is 12, 13, 14, 15, 16, 17, 18, 19, 20, 21, 22, 23, 24, 25, 26, 27, 28, 29, 30, 31, 32, 33, 34, 35, 36, 37, or 38. In some embodiments of any of the antisense oligomers, methods, or compositions described herein, Z is 12, 13, 14, 15, 16, 17, 18, 19, 20, 21, 22, 23, 24, 25, 26, 27, or 28. In some embodiments of any of the antisense oligomers, methods, or compositions described herein, Z is 15, 16, 17, 18, 19, 20, 21, 22, 23, 24, or 25.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 8 to 28.

In some embodiments, each Z of the modified antisense oligomers of the disclosure, including compounds of formulas (I), (Ia), (IVa), (IVb), (IVc), (V), (VI), (VII). (VIIa), (VIIb), (VIIc), (VIId), (VIIe), and (VIII), is an integer from 15 to 38.

In some embodiments, each Z of the modified antisense oligomers of the disclosure, including compounds of formulas (I), (Ia), (IVa), (IVb), (IVc), (V), (VI), (VII). (VIIa), (VIIb), (VIIc), (VIId), (VIIe), and (VIII), is an integer from 15 to 28.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 8 to 25.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 15 to 25.

In some embodiments, each Z of the modified antisense oligomers of the disclosure, including compounds of formulas (I), (Ia), (IVa), (IVb), (IVc), (V), (VI), (VII), (VIIa), (VIIb), (VIIe), (VIId), (VIIe), and (VIII), is an integer from 10 to 38.

In some embodiments, each Z of the modified antisense oligomers of the disclosure, including compounds of formulas (I), (Ia), (IVa), (IVb), (IVc), (V), (VI), (VII). (VIIa), (VIIb), (VIIc), (VIId), (VIIe), and (VIII), is an integer from 10 to 25.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 12 to 38.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 12 to 25.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 14 to 38.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is an integer from 14 to 25.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (VIIe), and (VIII), is 12, 13, 14, 15, 16, 17, 18, 19, 20, 21, 22, 23, 24, 25, 26, 27, 28, 29, 30, 31, 32, 33, 34, 35, 36, 37, or 38.

In some embodiments, each Z of the modified antisense oligomers of the disclosure, including compounds of formulas (I), (Ia), (IVa), (IVb), (IVc), (V), (VI), (VII). (VIIa), (VIIb), (VIIc), (VIId), (VIIe), and (VIII), is 12, 13, 14, 15, 16, 17, 18, 19, 20, 21, 22, 23, 24, 25, 26, 27, or 28.

In some embodiments, each Z of the modified antisense oligomers of the disclosure, including compounds of formulas (I), (Ia), (IVa), (IVb), (IVc), (V), (VI), (VII), (VIIa), (VIIb), (VIIc), (VIId), (Vile), and (VIII), is 15, 16, 17, 18, 19, 20, 21, 22, 23, 24, or 25.

In some embodiments, each Nu of the antisense oligomers of the disclosure, including compounds of formula (I), (Ia), (IVa), (IVb), (IVc), (V), (VI), (VII), (VIIa), (VIIb), (VIIc), (VIId), (VIIe), and (VIII), is independently selected from the group consisting of adenine, guanine, thymine, uracil, cytosine, hypoxanthine, 2,6-diaminopurine, 5-methyl cytosine, C5-propynyl-modified pyrimidines, and 9-(aminoethoxy) phenoxazine.

In some embodiments, the targeting sequence of the antisense oligomers of the disclosure, including compounds of formula (I), (Ia), (IVa), (IVb), (IVc), (V), (VI), (VII), (VIIa), (VIIb), (VIIc), (VIId), (Vile), and (VIII), is complementary to 10 or more contiguous nucleotides in a target region within intron 1, intron 2, or exon 2 of a pre-mRNA of the human acid alpha-glucosidase (GAA) gene. In certain embodiments, the targeting sequence of the antisense oligomers of the disclosure, including compounds of formula (I), (Ia), (IVa), (IVb), (IVc), (V), (VI), (VII), (VIIa), (VIIb), (VIIc), (VIId), (VIIe), and (VIII), is a fragment of at least 12 contiguous nucleotides, or is variant having at least 90% sequence identity to a sequence (where X can be selected from uracil (U) or thymine (T).

Additional antisense oligomers/chemistries that can be used in accordance with the present disclosure include those described in the following patents and patent publications, the contents of which are incorporated herein by reference: PCT Publication Nos. WO/2007/002390; WO/2010/120820; and WO/2010/148249; U.S. Pat. No. 7,838,657; and U.S. Application No. 2011/0269820.

The antisense oligonucleotides can be prepared by stepwise solid-phase synthesis, employing methods known in the art and described herein and in the references cited herein.

iii. Preparation of PMO-X with Basic Nitrogen Internucleoside Linkers

Morpholino subunits, the modified intersubunit linkages, and oligomers comprising the same can be prepared as described, for example, in U.S. Pat. Nos. 5,185,444, and 7,943,762, which are incorporated by reference in their entireties. The morpholino subunits can be prepared according to the following general Reaction Scheme I.

Reaction Scheme 1. Preparation of Morpholino Subunit

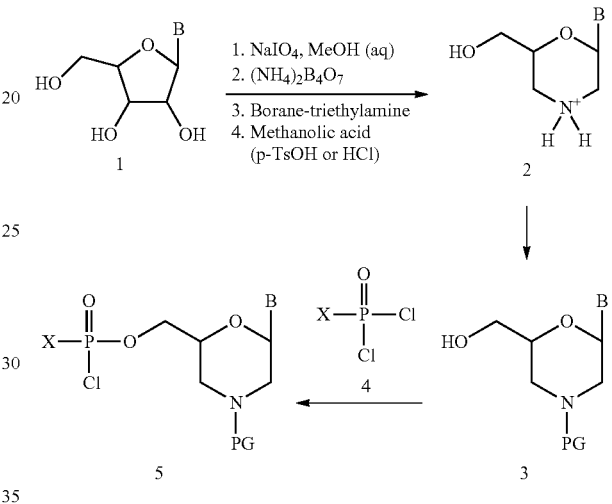

Referring to Reaction Scheme 1, wherein B represents a base pairing moiety and PG represents a protecting group, the morpholino subunits may be prepared from the corresponding ribonucleoside (1) as shown. The morpholino subunit (2) may be optionally protected by reaction with a suitable protecting group precursor, for example trityl chloride. The 3' protecting group is generally removed during solid-state oligomer synthesis as described in more detail below. The base pairing moiety may be suitably protected for sold phase oligomer synthesis. Suitable protecting groups include benzoyl for adenine and cytosine, phenylacetyl for guanine, and pivaloyloxymethyl for hypoxanthine (I). The pivaloyloxymethyl group can be introduced onto the N1 position of the hypoxanthine heterocyclic base. Although an unprotected hypoxanthine subunit, may be employed, yields in activation reactions are far superior when the base is protected. Other suitable protecting groups include those disclosed in co-pending U.S. application Ser. No. 12/271,040, which is hereby incorporated by reference in its entirety.

Reaction of 3 with the activated phosphorous compound 4, results in morpholino subunits having the desired linkage moiety 5. Compounds of structure 4 can be prepared using any number of methods known to those of skill in the art. For example, such compounds may be prepared by reaction of the corresponding amine and phosphorous oxychloride. In this regard, the amine starting material can be prepared using any method known in the art, for example those methods described in the Examples and in U.S. Pat. No. 7,943,762.

Compounds of structure 5 can be used in solid-phase automated oligomer synthesis for preparation of oligomers comprising the intersubunit linkages. Such methods are well known in the art. Briefly, a compound of structure 5 may be modified at the 5' end to contain a linker to a solid support. For example, compound 5 may be linked to a solid support by a linker comprising $L^{11}$ and $L^{15}$.

The morpholino oligomers containing any number of modified linkages may be prepared using methods described herein, methods known in the art and/or described by reference herein. Also described in the examples are global modifications of morpholino oligomers prepared as previously described (see e.g., PCT publication WO2008036127).

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxyl reactive moieties may also be blocked with hydrolytically removable protective groups such as the benzyl group, while amine groups may be blocked with base labile groups such as Fmoc. A particularly useful amine protecting group for the synthesis of compounds of Formula (I) is the trifluoroacetamide. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to the following moieties:

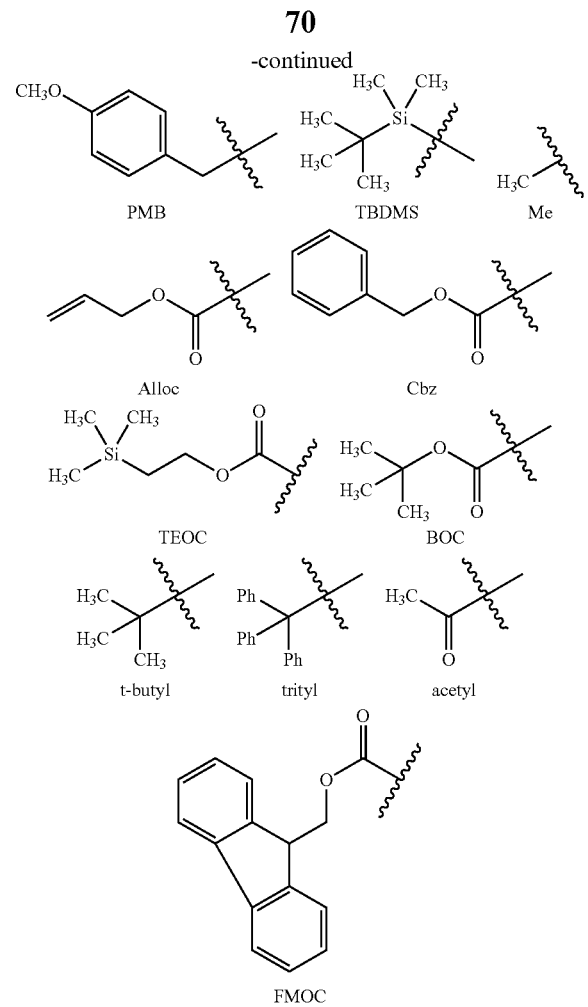

Unless otherwise noted, all chemicals were obtained from Sigma-Aldrich-Fluka. Benzoyl adenosine, benzoyl cytidine, and phenylacetyl guanosine were obtained from Carbosynth Limited, UK.

Synthesis of PMO, PMO+, PPMO, and PMO-X containing further linkage modifications as described herein was done using methods known in the art and described in pending U.S. application Ser. Nos. 12/271,036 and 12/271,040 and PCT publication number WO/2009/064471, which are hereby incorporated by reference in their entirety.

PMO with a 3' trityl modification are synthesized essentially as described in PCT publication number WO/2009/064471 with the exception that the detritylation step is omitted.

III. Formulations

The compounds of the present disclosure may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170;

5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the disclosure encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the disclosure, pharmaceutically acceptable salts of such prodrugs, and other bioequivalents.

As used herein, the term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligomers of the disclosure are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

As used herein, the term "pharmaceutically acceptable salts" refers to physiologically and pharmaceutically acceptable salts of the compounds of the disclosure: i.e., salts that retain the desired biological activity of the parent compound and do not impart undesired toxicological effects thereto. For oligomers, examples of pharmaceutically acceptable salts and their uses are further described in U.S. Pat. No. 6,287,860, which is incorporated herein in its entirety.

The present disclosure also includes pharmaceutical compositions and formulations which include the antisense compounds of the disclosure. The pharmaceutical compositions of the present disclosure may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligomers with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present disclosure, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present disclosure may be formulated into any of many possible dosage forms such as, but not limited to, tablets, capsules, gel capsules, liquid syrups, soft gels, suppositories, and enemas. The compositions of the present disclosure may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present disclosure include, but are not limited to, solutions, emulsions, foams and liposome-containing formulations. The pharmaceutical compositions and formulations of the present disclosure may comprise one or more penetration enhancers, carriers, excipients or other active or inactive ingredients.

Emulsions are typically heterogeneous systems of one liquid dispersed in another in the form of droplets usually exceeding 0.1 µm in diameter. Emulsions may contain additional components in addition to the dispersed phases, and the active drug which may be present as a solution in either the aqueous phase, oily phase or itself as a separate phase. Microemulsions are included as an embodiment of the present disclosure. Emulsions and their uses are well known in the art and are further described in U.S. Pat. No. 6,287,860, which is incorporated herein in its entirety.

Formulations of the present disclosure include liposomal formulations. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present disclosure may also include surfactants. The use of surfactants in drug products, formulations and in emulsions is well known in the art. Surfactants and their uses are further described in U.S. Pat. No. 6,287,860, which is incorporated herein in its entirety.

In some embodiments, the present disclosure employs various penetration enhancers to affect the efficient delivery of nucleic acids, particularly oligomers. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Formulations for topical administration include those in which the oligomers of the disclosure are in admixture with a topical delivery agent such as lipids, liposomes, fatty acids, fatty acid esters, steroids, chelating agents and surfactants. Lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA).

For topical or other administration, oligomers of the disclosure may be encapsulated within liposomes or may form complexes thereto, in particular to cationic liposomes. Alternatively, oligomers may be complexed to lipids, in particular to cationic lipids. Fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations are those in which oligomers of the disclosure are administered in conjunction with one or more penetration enhancers, surfactants and chelators. Surfactants include fatty acids and/or esters or salts thereof, bile acids and/or salts thereof. Bile acids/salts and fatty acids and their uses are further described in U.S. Pat. No. 6,287,860, which is incorporated herein in its entirety. In some embodiments, the present disclosure provides combinations of penetration enhancers, for example, fatty acids/salts in combination with bile acids/salts. An exemplary combination is the sodium salt of lauric acid, capric acid and UDCA. Further penetration enhancers include polyoxyethylene-9-lauryl ether, polyoxyethylene-20-cetyl ether. Oligomers of the disclosure may be delivered orally, in granular form including sprayed dried particles, or complexed to form micro or nanoparticles. Oligomer complexing agents and their uses are further described in U.S. Pat. No. 6,287,860, which is incorporated herein in its entirety. Oral formulations for oligomers and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the disclosure provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxyco-formycin, 4-hydroxyperoxycyclophosphoramide, 5-fluorouracil (5-FU). 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the disclosure, such chemotherapeutic agents may be used individually (e.g., 5-FU and oligomer), sequentially (e.g., 5-FU and oligomer for a period of time followed by MTX and oligomer), or in combination with one or more other such chemotherapeutic agents (e.g., 5-FU, MTX and oligomer, or 5-FU, radiotherapy and oligomer). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the disclosure. Combinations of antisense compounds and other non-antisense drugs are also within the scope of this disclosure. Two or more combined compounds may be used together or sequentially.

In another related embodiment, compositions of the disclosure may contain one or more antisense compounds, particularly oligomers, targeted to a first nucleic acid and one or more additional antisense compounds targeted to a second nucleic acid target. Alternatively, compositions of the disclosure may contain two or more antisense compounds targeted to different regions of the same nucleic acid target. Numerous examples of antisense compounds are known in the art. Two or more combined compounds may be used together or sequentially.

IV. Methods of Use

In further aspects, the antisense oligomer compounds described herein are used to treat diseases. In embodiments, the diseases are associated with a particular exon position or location wherein targeting at the exon position or location with the antisense oligomer compounds results in an increase or decrease of a mRNA or protein transcribed or translated from the exon position or location. In embodiments, an increase is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject. In embodiments, a decrease is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject.

In further aspects, the antisense oligomer compounds described herein are used to treat diseases associated with a particular exon position or location, wherein the particular exon position or location contains at least one string of three or more identical contiguous nucleobases in the target sequence, and wherein targeting at the exon position or location with the antisense oligomer compounds results in an increase or decrease of a mRNA or protein transcribed or translated from the exon position or location. In embodiments, an increase is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject. In embodiments, a decrease is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject.

In further aspects, the antisense oligomer compounds described herein are used to treat diseases associated with a particular exon position or location, wherein the particular exon position or location contains at least one biological palindrome sequence in the target sequence, and wherein targeting at the exon position or location with the antisense oligomer compounds results in an increase or decrease of a mRNA or protein transcribed or translated from the exon position or location. In embodiments, an increase is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject. In embodiments, a decrease is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject.

In embodiments, the antisense oligomer compounds described herein are used to treat an exon target associated with Duchenne muscular dystrophy (DMD) as described generally in PCT Publication No.: WO 2006/000057. In embodiments, the target sequence comprises exon 44 in the processing of human dystrophin pre-processed mRNA. In embodiments, the targeting sequence comprises any one of SEQ ID NOs: 2-7. In embodiments, the target sequence comprises exons 45, 51 or 53 of human dystrophin pre-processed mRNA. In embodiments, the targeting sequence comprises any one of SEQ ID NOs: 75-123. In embodiments, targeting at the described exon position or location with the antisense oligomer compounds results in an increase or decrease of a mRNA or protein transcribed or translated from the exon position or location. In embodiments, an increase is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject. In embodiments, a decrease is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject.

In embodiments, the antisense oligomer compounds described herein are used to treat an exon target associated with spinal muscular atrophy (SMA) as described generally in WO 2017/040271, the content of which is incorporated herein in its entirety. In embodiments, the target sequence comprises a region adjacent to exon 7 in the processing of human SMN2 pre-processed mRNA. In embodiments, the targeting sequence comprises any one of SEQ ID NOs: 9-25. In embodiments, targeting at the described exon position or location with the antisense oligomer compounds results in an increase or decrease of a mRNA or protein transcribed or translated from the exon position or location. In embodiments, an increase is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject. In embodiments, a decrease is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject.

In embodiments, the antisense oligomer compounds described herein are used to treat an exon target associated with glycogen storage disease type II (GSD-II) as described generally in PCT Patent Application No. PCT/US17/28002]. In embodiments, the target sequence comprises a region associated with exon 2 of the human acid alpha-glucosidase pre-processed mRNA. In embodiments, the targeting sequence comprises any one of SEQ ID NOs: 26-71. In embodiments, targeting at the described exon position or location with the antisense oligomer compounds results in an increase or decrease of a mRNA or protein transcribed or translated from the exon position or location. In embodiments, an increase is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject. In embodiments, a decrease is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, In various aspects and embodiments, the antisense oligomer compounds described herein include a deletion sequence and are used to treat diseases. In embodiments, the diseases are associated with a particular exon position or location, wherein targeting at the exon position or location with the antisense oligomer compounds results in an increase or decrease of a mRNA or protein transcribed or translated from the exon position or location. In embodiments, an increase is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject. In embodiments, a decrease is 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% relative to a control, for example, a control cell/subject. The deletion sequence comprises any one of SEQ ID NOs: 1-128, wherein at least one nucleobase in any one of SEQ ID NOs: 1-128 has been deleted. In various embodiments, the deletion sequence comprises CTCCAACATCAAGGAA-GATGGCATTTCTAG (SEQ ID NO: 69; Eteplirsen); GTTGCCTCCGGTTCTGAAGGTGTTC (SEQ ID NO: 70; Golodirsen); or CAATGCCATCCTGGAGTTCCTG (SEQ ID NO: 71; Casimersen). In various embodiments, the deletion sequence comprises any one of SEQ ID NOs: 69-71, wherein at least one nucleobase in any one of SEQ ID NOs: 69-71 has been deleted. In embodiments, the at least one nucleobase that has been deleted is internal to the sequence of any one of SEQ ID NOs: 69-71.

Accordingly, a physician or clinician may consider applying knowledge obtained in relevant pharmacogenomics studies in determining whether to administer a therapeutic agent as well as tailoring the dosage and/or therapeutic regimen of treatment with a therapeutic agent.

Effective delivery of the antisense oligomer to the target nucleic acid is one aspect of treatment. Routes of antisense oligomer delivery include, but are not limited to, various systemic routes, including oral and parenteral routes, e.g., intravenous, subcutaneous, intraperitoneal, and intramuscular, as well as inhalation, transdermal and topical delivery. The appropriate route may be determined by one of skill in the art, as appropriate to the condition of the subject under treatment. Vascular or extravascular circulation, the blood or lymph system, and the cerebrospinal fluid are some non-limiting sites where the RNA may be introduced. Direct CNS delivery may be employed, for instance, intracerebral ventribular or intrathecal administration may be used as routes of administration.

In particular embodiments, the antisense oligomer(s) are administered to the subject by intramuscular injection (IM), i.e., they are administered or delivered intramuscularly. Non-limiting examples of intramuscular injection sites include the deltoid muscle of the arm, the vastus lateralis muscle of the leg, and the ventrogluteal muscles of the hips, and dorsogluteal muscles of the buttocks. In specific embodiments, a PMO, PMO-X, or PPMO is administered by IM.

In certain embodiments, the subject in need thereof as glycogen accumulation in central nervous system tissues. Examples include instances where central nervous system pathology contributes to respiratory deficits in GSD-II (see, e.g., DeRuisseau et al., PNAS USA. 106:9419-24, 2009). Accordingly, the antisense oligomers described herein can be delivered to the nervous system of a subject by any art-recognized method, e.g., where the subject has GSD-II with involvement of the CNS. For example, peripheral blood injection of the antisense oligomers of the disclosure can be used to deliver said reagents to peripheral neurons via diffusive and/or active means. Alternatively, the antisense oligomers can be modified to promote crossing of the blood-brain-barrier (BBB) to achieve delivery of said reagents to neuronal cells of the central nervous system (CNS). Specific recent advancements in antisense oligomer technology and delivery strategies have broadened the scope of antisense oligomer usage for neuronal disorders (see, e.g., Forte, A., et al. 2005. Curr. Drug Targets 6:21-29; Jaeger, L. B., and W. A. Banks. 2005. Methods Mol. Med. 106:237-251; Vinogradov, S. V., et al. 2004. Bioconjug. Chem. 5:50-60; the foregoing is incorporated herein in their entirety by reference). For example, the antisense oligomers of the disclosure can be generated as peptide nucleic acid (PNA) compounds. PNA reagents have each been identified to cross the BBB (Jaeger, L. B., and W. A. Banks. 2005. Methods Mol. Med. 106:237-251). Treatment of a subject with, e.g., a vasoactive agent, has also been described to promote transport across the BBB (Id). Tethering of the antisense oligomers of the disclosure to agents that are actively transported across the BBB may also be used as a delivery mechanism. Administration of antisense agents together with contrast agents such as iohexol (e.g., separately, concurrently, in the same formulation) can also facilitate delivery across the BBB, as described in PCT Publication No. WO/2013/086207, incorporated by reference in its entirety.

In certain embodiments, the antisense oligomers of the disclosure can be delivered by transdermal methods (e.g., via incorporation of the antisense oligomers into, e.g., emulsions, with such antisense oligomers optionally packaged into liposomes). Such transdermal and emulsion/liposome-mediated methods of delivery are described for delivery of antisense oligomers in the art, e.g., in U.S. Pat. No. 6,965,025, the contents of which are incorporated in their entirety by reference herein.

The antisense oligomers described herein may also be delivered via an implantable device. Design of such a device is an art-recognized process, with, e.g., synthetic implant design described in, e.g., U.S. Pat. No. 6,969,400, the contents of which are incorporated in their entirety by reference herein.

Antisense oligomers can be introduced into cells using art-recognized techniques (e.g., transfection, electroporation, fusion, liposomes, colloidal polymeric particles and viral and non-viral vectors as well as other means known in the art). The method of delivery selected will depend at least on the oligomer chemistry, the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, antisense oligomers may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated by reference in its entirety).

The antisense oligomers may be administered in any convenient vehicle or carrier which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration. "Pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compounds (e.g., antisense oligomers) of the present disclosure may generally be utilized as the free acid or free base. Alternatively, the compounds of this disclosure may be used in the form of acid or base addition salts. Acid addition salts of the free amino compounds of the present disclosure may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

In addition, prodrugs are also included within the context of this disclosure. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the antisense oligomers of the disclosure. Further, in the case of a carboxylic acid (—COOH), esters may be employed, such as methyl esters, ethyl esters, and the like.

In some instances, liposomes may be employed to facilitate uptake of the antisense oligomer into cells (see, e.g., Williams, S. A., Leukemia 10(12):1980-1989, 1996; Lappalainen et al., Antiviral Res. 23:119, 1994; Uhlmann et al., antisense oligomers: a new therapeutic principle, Chemical Reviews, Volume 90, No. 4, 25 pages 544-584, 1990; Gregoriadis, G., Chapter 14, Liposomes, Drug Carriers in Biology and Medicine, pp. 287-341, Academic Press; 1979). Hydrogels may also be used as vehicles for antisense oligomer administration, for example, as described in WO 93/01286. Alternatively, the oligomers may be administered in microspheres or microparticles. (See, e.g., Wu, G. Y. and Wu, C. H., J. Biol. Chem. 262:4429-4432, 30 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In one embodiment, the antisense oligomer is administered to a mammalian subject, e.g., human or domestic animal, exhibiting the symptoms of a lysosomal storage disorder, in a suitable pharmaceutical carrier. In one aspect of the method, the subject is a human subject, e.g., a patient diagnosed as having GSD-II (Pompe disease). In one preferred embodiment, the antisense oligomer is contained in a pharmaceutically acceptable carrier, and is delivered orally. In another preferred embodiment, the oligomer is contained in a pharmaceutically acceptable carrier, and is delivered intravenously (i.v.).

In one embodiment, the antisense compound is administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-1000 mg oligomer per 70 kg. In some cases, doses of greater than 1000 mg oligomer/patient may be necessary. For i.v. administration, preferred doses are from about 0.5 mg to 1000 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

An effective in vivo treatment regimen using the antisense oligomers of the disclosure may vary according to the duration, dose, frequency and route of administration, as well as the condition of the subject under treatment (i.e., prophylactic administration versus administration in response to localized or systemic infection). Accordingly, such in vivo therapy will often require monitoring by tests appropriate to the particular type of disorder under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligomer of the disclosure may be determined from biological samples (tissue, blood, urine etc.) taken from a subject prior to, during and subsequent to administration of the antisense oligomer. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA in relation to a reference normal mRNA or protein as determined by standard techniques such as RT-PCR, Northern blotting, ELISA or Western blotting.

In some embodiments, the antisense oligomer is actively taken up by mammalian cells. In further embodiments, the antisense oligomer may be conjugated to a transport moiety (e.g., transport peptide or CPP) as described herein to facilitate such uptake.

V. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is affected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on EC50s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, ranging from 0.01 μg to 100 g per kg of body weight, once or more daily, to once every 20 years.

While the present disclosure has been described with specificity in accordance with certain of its embodiments, the following examples serve only to illustrate the disclosure and are not intended to limit the same. Each of the references, patents, patent applications, GenBank accession numbers, and the like recited in the present application are incorporated herein by reference in its entirety.

The following Examples illustrate various embodiments of the invention, without limitation.

EXAMPLES

Example 1: Oligomers Targeting Sequences with Runs of Multiple Nucleobases Form Aggregations This Example details that sequences with multiple homogeneous nucleobases present a problem during PMO manufacturing.

Specifically, the formation of intramolecular G-quartets can result in aggregation in the synthesis of G-rich PMOs such as GAA PMOs. Further, sequences that contain a series of three or more homogeneous nucleobases such as adenine, thymine, or cytosine, present similar problems of aggregation or other manufacturing issues and inefficiencies.

GAA PMOs, or other PMOs that have homogeneous strings of nucleobases, when analyzed by analytical strong cation exchange (SCX) HPLC result in several different peaks with quite different retention times. The multiple peaks should correspond to different aggregate forms of the conjugate.

Evidence for aggregation comes from HPLC performed using a Thermo Propac SCX-20 column. The buffer system and the HPLC operating conditions are shown in Table 1. The following procedure is used to prepare a drug product test sample for a lyophilized drug product at 100 mg per vial. After warming the sample to room temperature, a 3 mL syringe and needle are used to dispense 2.1 mL WFI into a vial. The sample is vortexed so that it dissolves completely. Prior to use, the sample is incubated at room temperature. A 3 mL syringe and needle are used to aspirate 2.0 mL of air into the vial. The vial is inverted, and 2.0 mL of solution is transferred from the vial to a glass container. Using a volumetric pipette, 1 mL of sample solution is dispensed and transferred into a 50 mL volumetric flask. The flask is filled to volume with PBS and mixed.

TABLE 1

Buffer System and HPLC Operating Conditions

| | |
|---|---|
| Mobile Phase A: | 24 mM $H_3PO_4$, 25% can |
| Mobile Phase B: | 24 mM $H_3PO_4$, 1.0M KCl, 25% can |
| Flow Rate: | 1.0 mL/minute |
| Column: | Thermo ProPac SCX-20, 4 × 250 mm |
| Column Temperature: | 60° C. |
| Autosampler Temperature: | 4° C. |
| Injector Volume: | 10 µL |
| Detector Wavelength: | 260 nm |
| Needle Wash: | 50% ACN in water |
| Run Time: | 30 minutes |

| Gradient Program: | Time (Minutes) | % Mobile Phase A | % Mobile Phase B |
|---|---|---|---|
| | 2.0 | 70 | 30 |
| | 22.0 | 35 | 65 |
| | 30.0 | 0 | 100 |
| | 30.1 | 0 | 100 |
| | 40.0 | 70 | 30 |

Expected chromatographic results are that the sequences with three or more consecutive G's produce an aggregation peak that elute much later than the un-aggregated species. The later-eluting peaks correspond to multimeric aggregate forms of the conjugate.

Further, it is possible that consecutive homogeneous nucleobase strings present a problem during PMO manufacturing. As the number of homogeneous nucleobases increases, it becomes more likely that unwanted N−1 deletions will happen. For example, a sequence containing a string of four thymines could produce unwanted N−1 deletions such that the final compound will only have three thymines. Under these circumstances, the three thymine compounds would then be considered to be an impurity Methods such as mass spectrometry can be used to decipher the N−1 deletion impurities.

Example 2: Oligomers Containing Deletions that Target Sequences with Runs of Multiple Nucleobases Prevent Aggregations To mediate the problems presented by strings of homogeneous nucleobases that impact PMO manufacturing, removal of a single base or multiple bases from the string of homogeneous nucleobases should correct the aggregation or other manufacturing problems. Table 2 shows the sequences that are fully complementary and the corresponding deletion sequences that will be tested that will resolve the issue presented in Example 1. In order to disrupt the aggregation of PMO or mediate the manufacturing problems, PMOs will be synthesized with deletions for guanine and thymine.

TABLE 2

Representative deletion sequence compounds with deletions

| Compound[1] | Sequence[2] | SEQ ID NO |
|---|---|---|
| GAA-IVS1.A (−65-41) | GGC GGC ACN CAC GGG GCN CNC AAA G | 121 |
| GAA-IVS1.A (−65-41)-G | GGC GGC ACN CAC GGG CNC NCA AAG | 62 |
| GAA-IVS1.A (−65-41)-2G | GGC GGC ACN CAC GG CNC NCA AAG | 122 |
| GAA-IVS1.A (−65-41)-3G | GGC GGC ACN CAC GCN CNC AAA G | 63 |
| GAA-IVS1.A (−65-41)-4G | GGC GGC ACN CAC CNC NCA AAG | 64 |
| GAA-IVS1.A (−76-52) | CGG GGC NCN CAA AGC AGC NCN GAG A | 123 |
| GAA-IVS1.A (−76-52)-G | CGG GCN CNC AAA GCA GCN CNG AGA | 59 |
| GAA-IVS1.A (−76-52)-2G | CGG CN CNC AAA GCA GCN CNG AGA | 34 |
| GAA-IVS1.A (−76-52)-3G | CGC NCN CAA AGC AGC NCN GAG A | 60 |

TABLE 2-continued

Representative deletion sequence compounds with deletions

| Compound[1] | Sequence[2] | SEQ ID NO |
|---|---|---|
| GAA-IVS1.A (-76-52)-4G | CCN CNC AAA GCA GCN CNG AGA | 61 |
| GAA-IVS1.A.(-180,-156) | NGG GGA GAG GGC CAG AAG GAA GGG C | 124 |
| GAA-IVS1.A.(-180,-156)-G | NGG GGA GAG GGC CAG AAG GAA GGC | 52 |
| GAA-IVS1.A.(-180,-156)-2G | NGG GGA GAG GGC CAG AAG GAA GC | 53 |
| GAA-IVS1.A.(-180,-156)-3G | NGG GGA GAG GGC CAG AAG GAA C | 54 |
| GAA-IVS1.A.(-189,-165) | GGC CAG AAG GAA GGG CGA GAA AAG C | 125 |
| GAA-IVS1.A.(-189,-165)-G | GGC CAG AAG GAA GGC GAG AAA AGC | 126 |
| GAA-IVS1.A.(-189,-165)-2G | GGC CAG AAG GAA GCG AGA AAA GC | 127 |
| GAA-IVS1.A.(-189,-165)-3G | GGC CAG AAG GAA CGA GAA AAG C | 128 |

[1]Reference to "A" in a Compound such as in GAA-IVS1A (0180,-156) et seq is reference to an acceptor splice site.
[2]Reference to "N" in a Sequence includes the independent selection of thymine (T) or uracil (U).

Analysis is performed under highly aggregating SCX HPLC conditions or mass spectrometry as specified in Example 1.

The deletion of guanines or thymines based on Table 2 sequences should have an effect on the relative amount of aggregation or efficiency of PMO manufacturing. With the deletion of just one or two nucleobases, the percent conjugate in the aggregate form should decrease from that of the fully complementary form or the percentage of product that is the desired structure should increase compared to the fully complementary structure.

Based on the unexpected results from other Examples described herein which demonstrate that internal deletions of nucleobases do not significantly decrease PMO activity (exon skipping or inclusion), it is rationally expected that deletion of one or two nucleobases to decrease the number of homogeneous nucleobases in Table 2 will not impact their functional activity.

Example 3: Exon Skipping Percentages for Certain Deletion Sequence Compounds that Target Exon 44

Deletion sequence oligomers were prepared having the sequences shown in Table 3.

TABLE 3

Deletion sequence oligomers targeting exon 44

| Compound[1] | Sequence[2] | SEQ ID NO |
|---|---|---|
| H44A (-01+24) Fully complementary | NNC NCA ACA GAN CNG NCA AAN CGC C | 1 |
| H44A (-1+24) bleb1 | NNC NCA ACG ANC NGN CAA ANC GCC | 2 |
| H44A (-1+24) bleb3 | NNC NCA ACA GNC NGN CAA ANC GCC | 3 |
| H44A (-1+24) bleb4 | NNC NCA ACA GAC NGN CAA ANC GCC | 4 |
| H44A (-1+24) bleb2 | NNC NCA ACA ANC NGN CAA ANC GCC | 5 |
| H44A (-1+24) bleb6 | NNC NCA ACA GAN CGN CAA ANC GCC | 6 |
| H44A (-1+24) bleb5 | NNC NCA ACA GAN NGN CAA ANC GCC | 7 |

[1]Reference to "A" in a Compound such as in H44A (-1+24) bleb1 et seq is reference to an acceptor splice site.
[2]Reference to "N" in a Sequence includes the independent selection of thymine (T) or uracil (U).

Varying concentrations (20 µM, 10 µM, 5 µM, 2.5 µM, 1.25 µM and 0.625 µM) of the compounds were tested and values of exon skipping % were determined according to PCT Patent Publication No. WO 2014/153220, the content of which is incorporated herein in its entirety. The results are shown in FIG. 1. Additionally, as shown in FIG. 1, the fold increase in potency over control for the compounds identified in Table 3 was determined as shown in Table 4.

TABLE 4

Fold increase for deletion sequence oligomers targeting exon 44

| Compound[1] | Fold increase in potency over control |
|---|---|
| H44A (-01 + 24) Fully complementary | 7.4 |
| H44A (-1 + 24) bleb1 | 8.5 |
| H44A (-1 + 24) bleb3 | 7.2 |
| H44A (-1 + 24) bleb4 | 6.1 |
| H44A (-1 + 24) bleb2 | 6.0 |
| H44A (-1 + 24) bleb6 | 5.9 |
| H44A (-1 + 24) bleb5 | 3.3 |

[1]Reference to "A" in a Compound such as in H44A (-1 + 24) bleb1 et seq is reference to an acceptor splice site.

Example 4: Exon Inclusion Percentages for Certain Deletion Sequence Compounds that Target Exon 7

Figure 2:
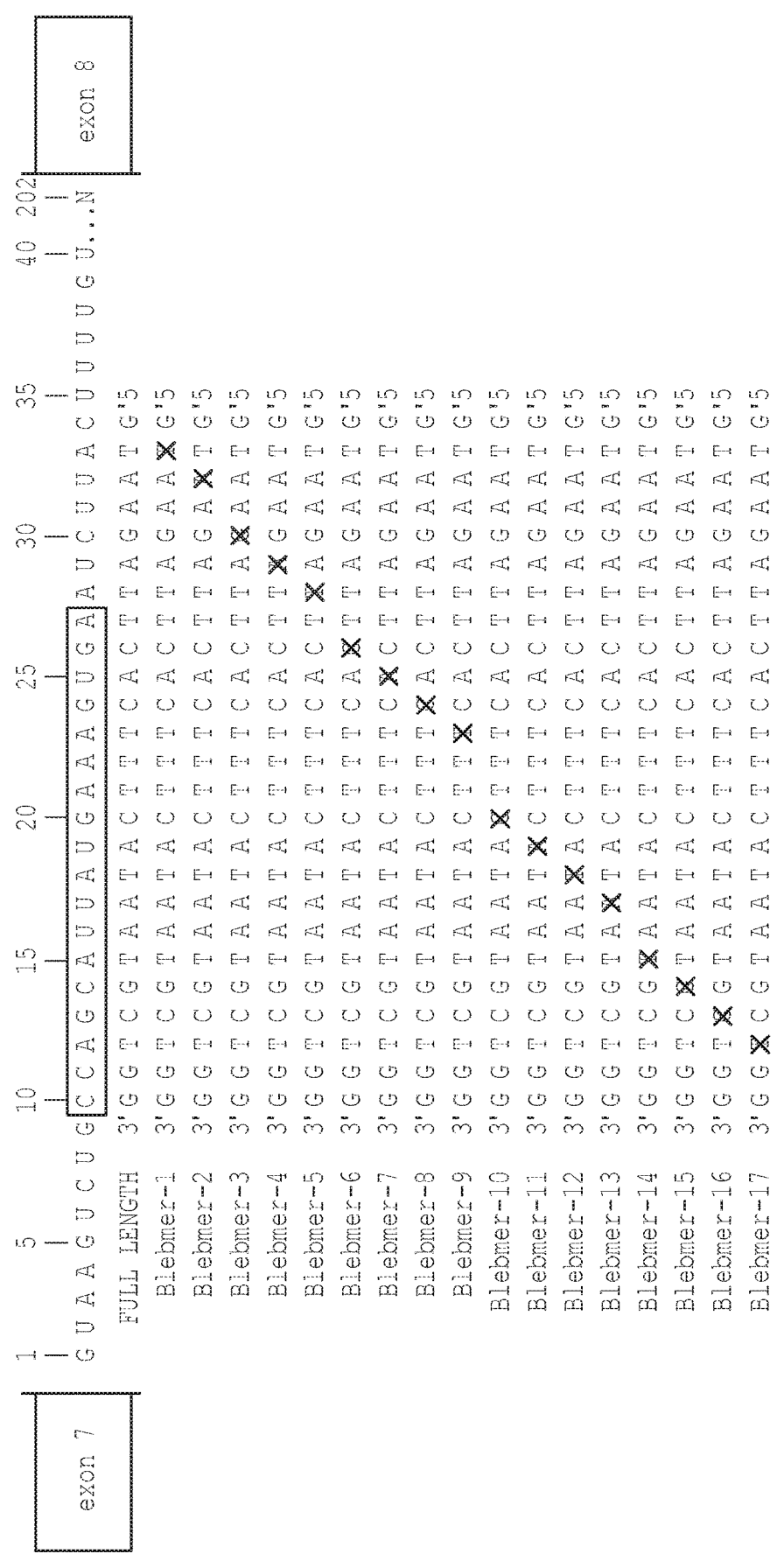

Deletion sequence oligomers were prepared having the sequences shown in Table 5 and FIG. 2.

TABLE 5

Deletion sequence oligomers targeting exon 7

| Compound[1] | Sequence[2,3] | SEQ ID NO |
|---|---|---|
| SMN2.7D 10C-10-34 | 3'-GGNCGNAANACNN NCACNNAGAANG-5' | 8 |
| SMN2.7D(-10-34) blebmer1 | 3'-GGNCGNAANACNN NCACNNAGAAXG-5' | 9 |
| SMN2.7D(-10-34) blebmer2 | 3'-GGNCGNAANACNN NCACNNAGAXNG-5' | 10 |
| SMN2.7D(-10-34) blebmer3 | 3'-GGNCGNAANACNN NCACNNAXAANG-5' | 11 |
| SMN2.7D(-10-34) blebmer4 | 3'-GGNCGNAANACNN NCACNNXGAANG-5' | 12 |
| SMN2.7D(-10-34) blebmer5 | 3'-GGNCGNAANACNN NCACNXAGAANG-5' | 13 |
| SMN2.7D(-10-34) blebmer6 | 3'-GGNCGNAANACNN NCAXNNAGAANG-5' | 14 |
| SMN2.7D(-10-34) blebmer7 | 3'-GGNCGNAANACNN NCXCNNAGAANG-5' | 15 |
| SMN2.7D(-10-34) blebmer8 | 3'-GGNCGNAANACNN NXACNNAGAANG-5' | 16 |
| SMN2.7D(-10-34) blebmer9 | 3'-GGNCGNAANACNN XCACNNAGAANG-5' | 17 |
| SMN2.7D(-10-34) blebmer10 | 3'-GGNCGNAANAXNN NCACNNAGAANG-5' | 18 |
| SMN2.7D(-10-34) blebmer11 | 3'-GGNCGNAANXCNN NCACNNAGAANG-5' | 19 |
| SMN2.7D(-10-34) blebmer12 | 3'-GGNCGNAAXACNN NCACNNAGAANG-5' | 20 |
| SMN2.7D(-10-34) blebmer13 | 3'-GGNCGNAXNACNN NCACNNAGAANG-5' | 21 |
| SMN2.7D(-10-34) blebmer14 | 3'-GGNCGXAANACNN NCACNNAGAANG-5' | 22 |
| SMN2.7D(-10-34) blebmer15 | 3'-GGNCXNAANACNN NCACNNAGAANG-5' | 23 |
| SMN2.7D(-10-34) blebmer16 | 3'-GGNXGNAANACNN NCACNNAGAANG-5' | 24 |
| SMN2.7D(-10-34) blebmer17 | 3'-GGXCGNAANACNN NCACNNAGAANG-5' | 25 |

[1]Reference to "D" in a Compound such as in SMN2.7D(-10-34) blebmer1 et seq is reference to a donor splice site.
[2]Reference to "N" in a Sequence includes the independent selection of thymine (T) or uracil (U).
[3]Reference to "X" in a Sequence signifies a deletion at that nucleobase position.

Figure 3:
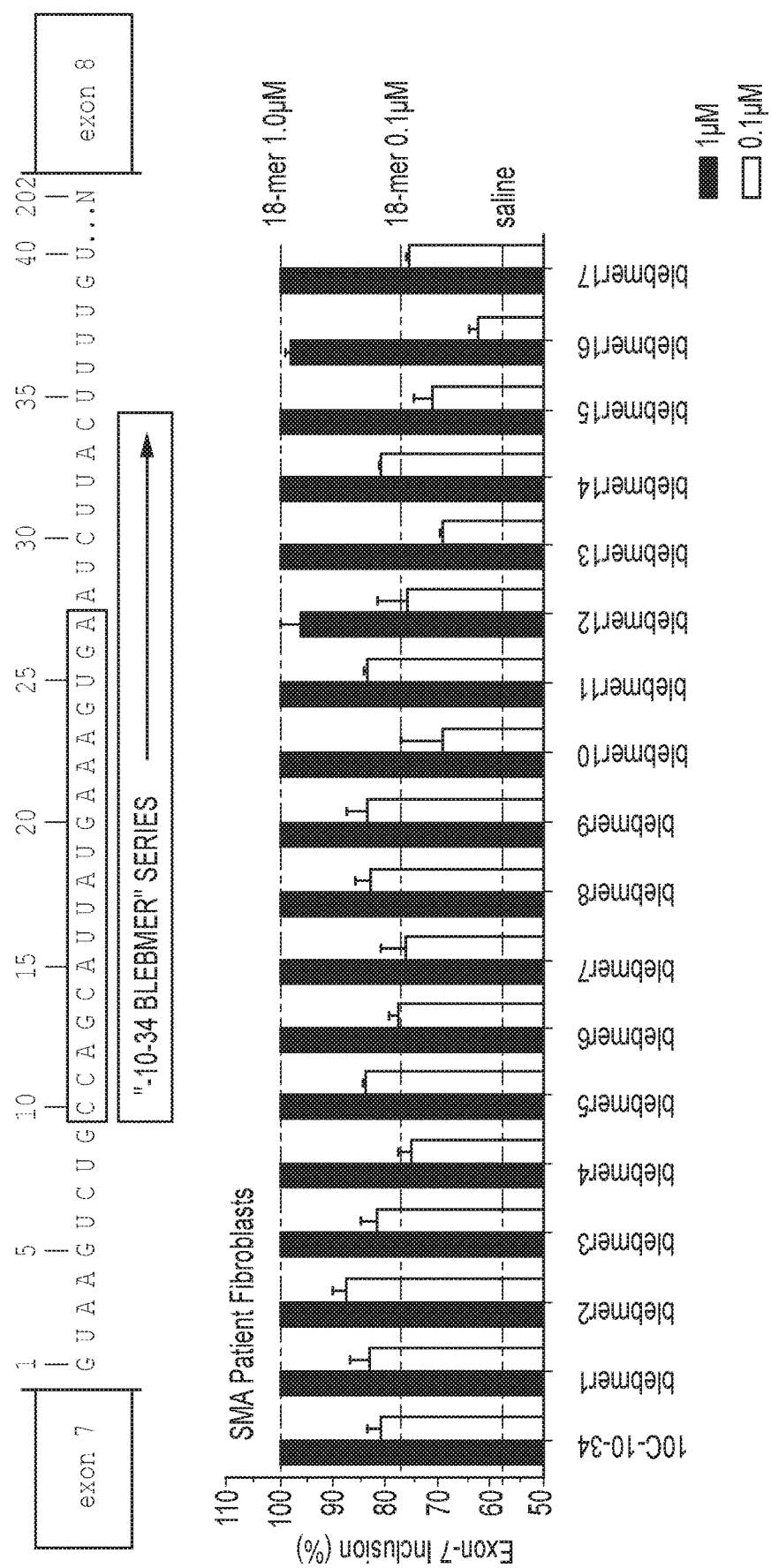
FIG. 3 details exon skipping percentages for deletion sequences detailed in FIG. 2 against a region adjacent to exons 7 and 8.

Varying concentrations (1 μM and 0.1 μM) of the compounds were tested and values for exon 7 inclusion % were determined according to WO 2017/040271, the content of which is incorporated herein in its entirety. The results are shown in FIG. 3. Gapmer/blebmer sequences 1, 2, 3, 5, 8, 9, 11, and 14 showed the best activities.

Example 5: Exon Inclusion Percentages for Certain Deletion Sequence Compounds that Target Exon 7

Figure 4:
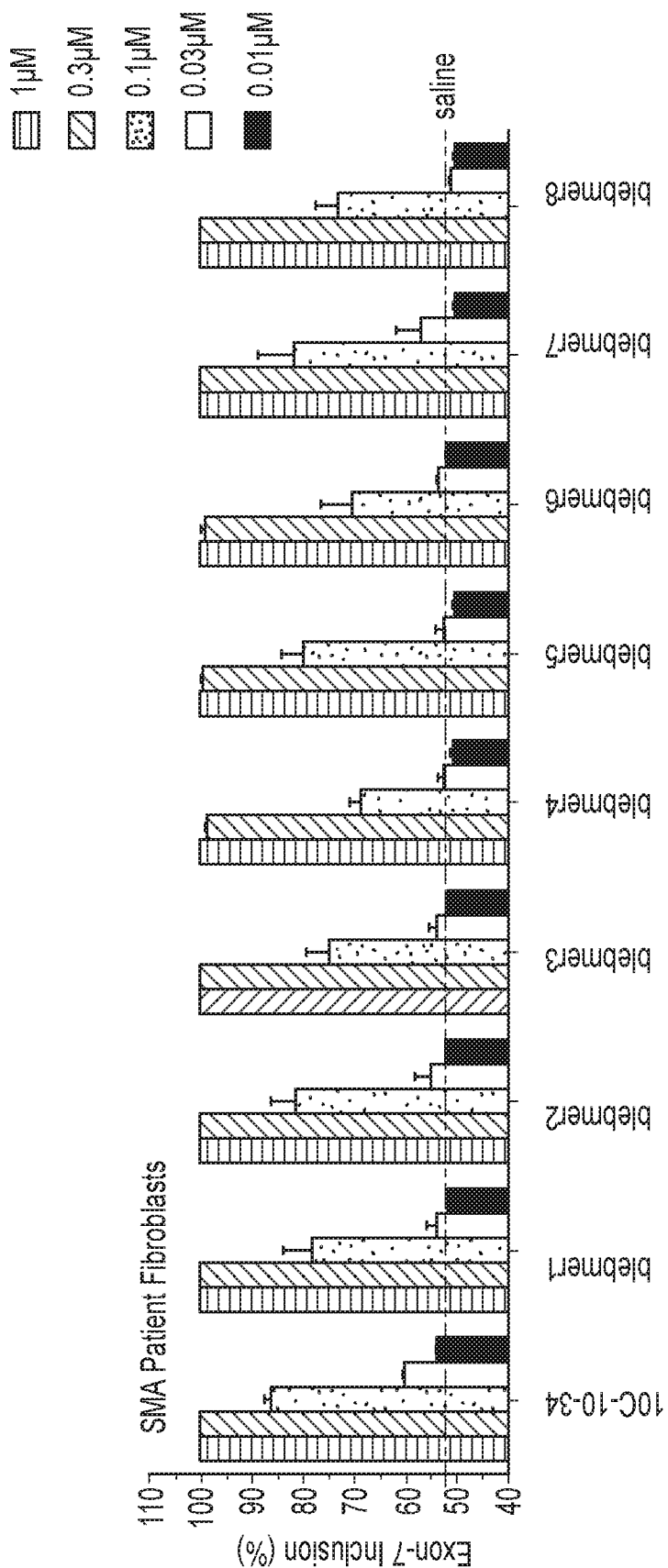
FIGS. 4 and 5 detail full-dose response experiments that identify a subset of 1-base-deletion sequences with high activity.

Oligomers were prepared having the sequences shown in Table 5 herein. Varying concentrations (1 μM, 0.3 μM, 0.1 μM, 0.03 μM, and 0.01 μM) of a subset of the compounds were tested and values for exon 7 inclusion % were determined according to WO 2017/040271, the content of which is incorporated herein in its entirety. The results are shown in FIG. 4.

Figure 5:
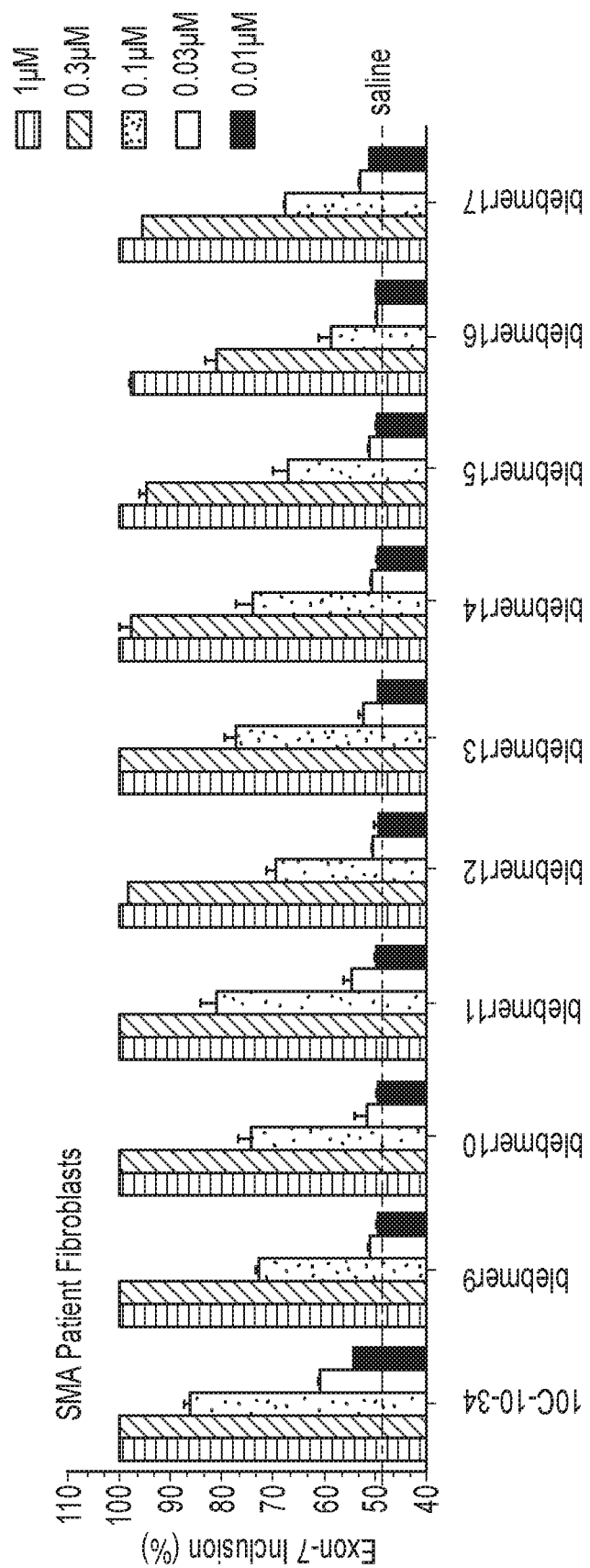

Further, in a separate set of experiments, varying concentrations (1 μM, 0.3 μM, 0.1 μM, 0.03 μM, and 0.01 μIV) of a subset of the compounds were tested and values for exon 7 inclusion % were determined. The results are shown in FIG. 5. Gapmer/blebmer sequences 2, 7, and 11 showed the best activities in the data depicted in FIGS. 4 and 5.

Example 6: Modulating GAA Enzyme Activity for Certain Deletion Sequence Compounds that Target Exon 2

Deletion sequences have been designed to treat Pompe disease (also referred to herein as glycogen storage disease type II). Detailed in Table 6 are representative oligomers designed for treating Pompe disease.

TABLE 6

Representative deletion sequences for treating Pompe disease

| Coordinates[1] | Targeting Sequence (TS)[2] (5'-3') | SEQ ID NO |
|---|---|---|
| GAA-IVS1.A. (-189,-165)-G | GGC CAG AAG GAA GGC GAG AAA AGC | 26 |
| GAA-IVS1.A. (-190,-166)-G | GCC AGA AGG AAG GC GAG AAA AGC N | 27 |
| GAA-IVS1.A. (-191,-167)-G | CCA GAA GGA AGG CGA GAA AAG CNC | 28 |
| GAA-IVS1.A. (-192,-168)-G | CAG AAG GAA GGC GAG AAA AGC NCC | 29 |
| GAA-IVS1.A. (-193,-169)-G | AGA AGG AAG GCG AGA AAA GCN CCA | 30 |
| GAA-IVS1.A. (-194,-170)-G | GAA GGA AGG CGA GAA AAG CNC CAG | 31 |
| GAA-IVS1.A. (-195,-171)-G | AAG GAA GGC GAG AAA AGC NCC AGC | 32 |
| GAA-IVS1.A. (-196,-172)-G | AGG AAG GCG AGA AAA GCN CCA GCA | 33 |
| GAA-IVS1.A. (-76-52)-2G | CGG CNC NCA AAG CAG CNC NGA GA | 34 |
| GAA-IVS1.A. (-75-51)-2G | ACG GCN CNC AAA GCA GCN CNG AG | 35 |
| GAA-IVS1.A. (-74-50)-2G | CAC GGC NCN CAA AGC AGC NCN GA | 36 |
| GAA-IVS1.A. (-73-49)-2G | NCA CGG CNC NCA AAG CAG CNC NG | 37 |
| GAA-IVS1.A. (-72-48)-2G | CNC ACG GCN CNC AAA GCA GCN CN | 38 |
| GAA-IVS1.A. (-71-47)-2G | ACN CAC GGC NCN CAA AGC AGC NC | 39 |

TABLE 6-continued

Representative deletion sequences for treating Pompe disease

| Coordinates[1] | Targeting Sequence (TS)[2] (5'-3') | SEQ ID NO |
|---|---|---|
| GAA-IVS1.A.(-66-42)-2G | GCG GCA CNC ACG GCN CNC AAA GC | 40 |
| GAA-IVS1.A.(-65-41)-2G | GGC GGC ACN CAC GGC NCN CAA AG | 41 |
| GAA-IVS1.A.(-67-43)-2G | CGG CAC NCA CGG CNC NCA AAG CA | 42 |
| GAA-IVS1.A.(-69-45)-2G | GCA CNC ACG GCN CNC AAA GCA GC | 43 |
| GAA-IVS1.A.(-68-44)-2G | GGC ACN CAC GGC NCN CAA AGC AG | 44 |
| GAA-IVS1.A.(-70-46)-2G | CAC NCA CGG CNC NCA AAG CAG CN | 45 |
| GAA-IVS1.A.(-189,-166)-G | GCC AGA AGG AAG GCG AGA AAA GC | 46 |
| GAA-IVS1.A.(-189,-167)-G | CCA GAA GGA AGG CGA GAA AAG C | 47 |
| GAA-IVS1.A.(-189,-168)-G | CAG AAG GAA GGC GAG AAA AGC | 48 |
| GAA-IVS1.A.(-188,-165)-G | GGC CAG AAG GAA GGC GAG AAA AG | 49 |
| GAA-IVS1.A.(-187,-165)-G | GGC CAG AAG GAA GGC GAG AAA A | 50 |
| GAA-IVS1.A.(-186,-165)-G | GGC CAG AAG GAA GGC GAG AAA | 51 |
| GAA-IVS1.A.(-67-43)-2G | CGG CAC NCA CGGC NCN CAA AGC A | 42 |
| GAA-IVS1.A.(-66-42)-2G | GCG GCA CNC ACGG CNC NCA AAG C | 40 |
| GAA-IVS1.A.(-65-41)-2G | GGC GGC ACN CAC G GCN CNC AAA G | 41 |
| GAA-IVS1.A.(-180,-156)-G | NGG GGA GAG GGC CAG AAG GAA GGC | 52 |
| GAA-IVS1.A.(-180,-156)-2G | NGG GGA GAG GGC CAG AAG GAA GC | 53 |
| GAA-IVS1.A.(-180,-156)-3G | NGG GGA GAG GGC CAG AAG GAA C | 54 |
| GAA-IVS1.A.(-189,-165)-2G | GGC CAG AAG GAA GCG AGA AAA GC | 55 |
| GAA-IVS1.A.(-189,-165)-3G | GGC CAG AAG GAA CGA GAA AAG C | 56 |
| GAA-IVS1.A.(-196,-172)-2G | AGG AAG CGA GAA AAG CNC CAG CA | 57 |
| GAA-IVS1.A.(-196,-172)-3G | AGG AAG GAG AAA AGC NCC AGC A | 58 |
| GAA-IVS1.A.(-76-52)-G | GGG GCN CNC AAA GCA GCN CNG AGA | 59 |
| GAA-IVS1.A.(-76-52)-3G | GGG NCN CAA AGC AGC NCN GAG A | 60 |
| GAA-IVS1.A.(-76-52)-4G | CCN CNC AAA GCA GCN CNG AGA | 61 |
| GAA-IVS1.A.(-65-41)-G | GGC GGC ACN CAC GGG CNC NCA AAG | 62 |
| GAA-IVS1.A.(-65-41)-3G | GGC GGC ACN CAC GCN CNC AAA G | 63 |
| GAA-IVS1.A.(-65-41)-4G | GGC GGC ACN CAC CNC NCA AAG | 64 |
| GAA-IVS1.A.(-57-33)-G | GCG GGA GGG GCG GCA CNC ACG GGC | 65 |
| GAA-IVS1.A.(-57-33)-2G | GCG GGA GGG GCG GCA CNC ACG GC | 66 |
| GAA-IVS1.A.(-57-33)-3G | GCG GGA GGG GCG GCA CNC ACG C | 67 |
| GAA-IVS1.A.(-57-33)-4G | GCG GGA GGG GCG GCA CNC ACC | 68 |

[1]Reference to "A" in a Compound such as in GAA-IVS1.A.(-75-51)-2G et seq is reference to an acceptor splice site.
[2]For any of the sequences detailed herein, each "N" is independently selected from thymine (T) or uracil (U).

Oligomers are prepared having the sequences shown in Table 6 herein. Varying concentrations of a subset of the compounds are tested and changes in GAA enzyme activity are measured according to PCT Application No. PCT/US17/28002, the content of which is incorporated herein in its entirety.

Example 7: Exon Skipping Percentages for Certain Deletion Sequence Compounds that Target Exons 51, 53, and 45

Deletion sequences have been designed to targeting exons 51, 53, and 45 of the dystrophin gene. Detailed in Table 7 are representative oligomers designed to targeting exons 51, 53, and 45.

TABLE 7

Representative deletion sequences for targeting exons 51, 53, and 45 of the dystrophin gene

| Coordinates[1] | Targeting Sequence (TS)[2] (5'-3') | SEQ ID NO |
|---|---|---|
| H51A(+66+95)D1 | CCCAACANCAAGGAAGANGGCANNNCNAG | 72 |
| H51A(+66+95)D2 | CNCAACANCAAGGAAGANGGCANNNCNAG | 73 |
| H51A(+66+95)D3 | CNCCACANCAAGGAAGANGGCANNNCNAG | 74 |
| H51A(+66+95)D4 | CNCCAAANCAAGGAAGANGGCANNNCNAG | 75 |

TABLE 7-continued

Representative deletion sequences for targeting exons 51, 53, and 45 of the dystrophin gene

| Coordinates[1] | Targeting Sequence (TS)[2] (5'-3') | SEQ ID NO |
|---|---|---|
| H51A(+66+95)D5 | CNCCAACNCAAGGAAGANGGCANNNCNAG | 76 |
| H51A(+66+95)D6 | CNCCAACACAAGGAAGANGGCANNNCNAG | 77 |
| H51A(+66+95)D7 | CNCCAACANAAGGAAGANGGCANNNCNAG | 78 |
| H51A(+66+95)D8 | CNCCAACANCAGGAAGANGGCANNNCNAG | 79 |
| H51A(+66+95)D9 | CNCCAACANCAAGAAGANGGCANNNCNAG | 80 |
| H51A(+66+95)D10 | CNCCAACANCAAGGAGANGGCANNNCNAG | 81 |
| H51A(+66+95)D11 | CNCCAACANCAAGGAAANGGCANNNCNAG | 82 |
| H51A(+66+95)D12 | CNCCAACANCAAGGAAGNGGCANNNCNAG | 83 |
| H51A(+66+95)D13 | CNCCAACANCAAGGAAGAGGCANNNCNAG | 84 |
| H51A(+66+95)D14 | CNCCAACANCAAGGAAGANGCANNNCNAG | 85 |
| H51A(+66+95)D15 | CNCCAACANCAAGGAAGANGGANNNCNAG | 86 |
| H51A(+66+95)D16 | CNCCAACANCAAGGAAGANGGCNNNCNAG | 87 |
| H51A(+66+95)D17 | CNCCAACANCAAGGAAGANGGCANNCNAG | 88 |
| H51A(+66+95)D18 | CNCCAACANCAAGGAAGANGGCANNNAG | 89 |
| H51A(+66+95)D19 | CNCCAACANCAAGGAAGANGGCANNNCAG | 90 |
| H51A(+66+95)D20 | CNCCAACANCAAGGAAGANGGCANNNCNG | 91 |
| H53A(+36+60)D1 | GNGCCNCCGGNNCNGAAGGNGNNC | 92 |
| H53A(+36+60)D2 | GNNCCNCCGGNNCNGAAGGNGNNC | 93 |
| H53A(+36+60)D3 | GNNGCNCCGGNNCNGAAGGNGNNC | 94 |
| H53A(+36+60)D4 | GNNGCCCCGGNNCNGAAGGNGNNC | 95 |
| H53A(+36+60)D5 | GNNGCCNCGGNNCNGAAGGNGNNC | 96 |
| H53A(+36+60)D6 | GNNGCCNCCGNNCNGAAGGNGNNC | 97 |
| H53A(+36+60)D7 | GNNGCCNCCGGNCNGAAGGNGNNC | 98 |
| H53A(+36+60)D8 | GNNGCCNCCGGNNGAAGGNGNNC | 99 |
| H53A(+36+60)D9 | GNNGCCNCCGGNNCGAAGGNGTNNC | 100 |
| H53A(+36+60)D10 | GNNGCCNCCGGNNCNAAGGNGNNC | 101 |
| H53A(+36+60)D11 | GNNGCCNCCGGNNCNGAGGNGNNC | 102 |
| H53A(+36+60)D12 | GNNGCCNCCGGNNCNGAAGNGNNC | 103 |
| H53A(+36+60)D13 | GNNGCCNCCGGNNCNGAAGGGNNC | 104 |
| H53A(+36+60)D14 | GNNGCCNCCGGNNCNGAAGGNNNC | 105 |
| H53A(+36+60)D15 | GNNGCCNCCGGNCNGAAGGNGNC | 106 |
| H45A(-03+16)D1 | CANGCCANCCNGGAGNNCCNG | 107 |
| H45A(-03+16)D2 | CAAGCCANCCNGGAGNNCCNG | 108 |
| H45A(-03+16)D3 | CAANCCANCCNGGAGNNCCNG | 109 |
| H45A(-03+16)D4 | CAANGCANCCNGGAGNNCCNG | 110 |
| H45A(-03+16)D5 | CAANGCCNCCNGGAGNNCCNG | 111 |
| H45A(-03+16)D6 | CAANGCCACCNGGAGNNCCNG | 112 |
| H45A(-03+16)D7 | CAANGCCANCNGGAGNNCCNG | 113 |
| H45A(-03+16)D8 | CAANGCCANCCGGAGNNCCNG | 114 |
| H45A(-03+16)D9 | CAANGCCANCCNGAGNNCCNG | 115 |
| H45A(-03+16)D10 | CAANGCCANCCNGGGNNCCNG | 116 |
| H45A(-03+16)D11 | CAANGCCANCCNGGANNCCNG | 117 |
| H45A(-03+16)D12 | CAANGCCANCCNGGAGNCCNG | 118 |
| H45A(-03+16)D13 | CAANGCCANCCNGGAGNNCNG | 119 |
| H45A(-03+16)D14 | CAANGCCANCCNGGAGNNCCG | 120 |

[1] Reference to "A" in a Compound such as in H51A(+66+95)D1 et seq is reference to an acceptor splice site.

[2] Reference to "N" in a Sequence includes the independent selection of thymine (T) or uracil (U).

Oligomers are prepared having the sequences shown in Table 7 herein. Varying concentrations of the compounds were tested and values of exon skipping % are determined according to PCT Patent Publication No. WO 2014/153220, the content of which is incorporated herein in its entirety.

Example 8: Reduced Aggregation after Intral-G Deletion(s) in Targeting Sequences Removal of an internal-G nucleotide(s) from targeting sequences results in reduced aggregation. HPLC was performed on SEQ ID NO: 125 and SEQ ID NO: 126. These sequences are identical except that SEQ ID NO: 126 has an internal G deletion relative to SEQ ID NO: 125. Both sequences were tested as part of the PMO and PPMO backbone structures. HPLC was performed according to the procedure described in Example 1 using the buffer system and HPLC operating conditions described in Table 1.

Figure 6B:
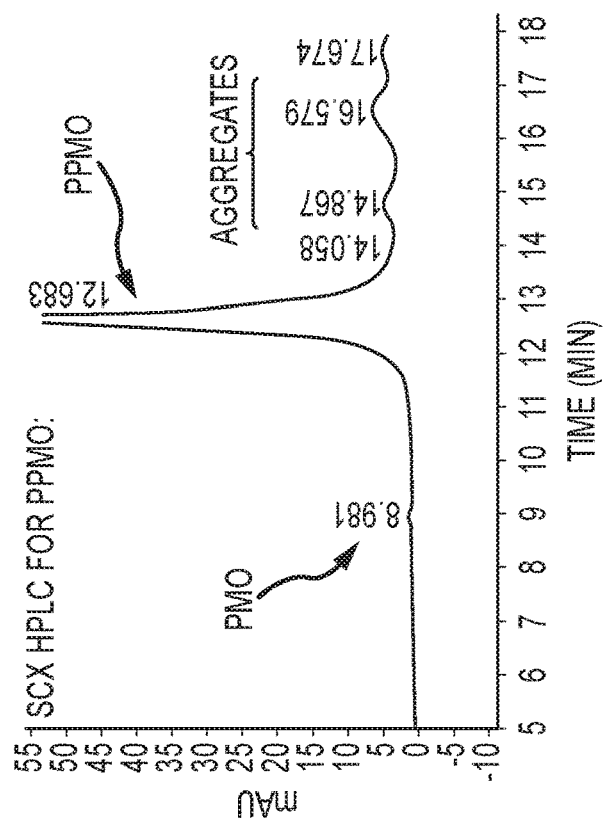
FIGS. 6A and 6B details SCX HPLC chromatograms (PMO and PPMO) for SEQ ID NO: 125. (A) details a chromatogram for SEQ ID NO: 125 PMO. (B) details a chromatogram for SEQ ID NO: 125 as a PPMO, showing unconjugated PMO, the expected main peak of conjugated PPMO, and higher molecular weight aggregates with the SEQ ID NO: 125 PPMO.
Figure 6A:
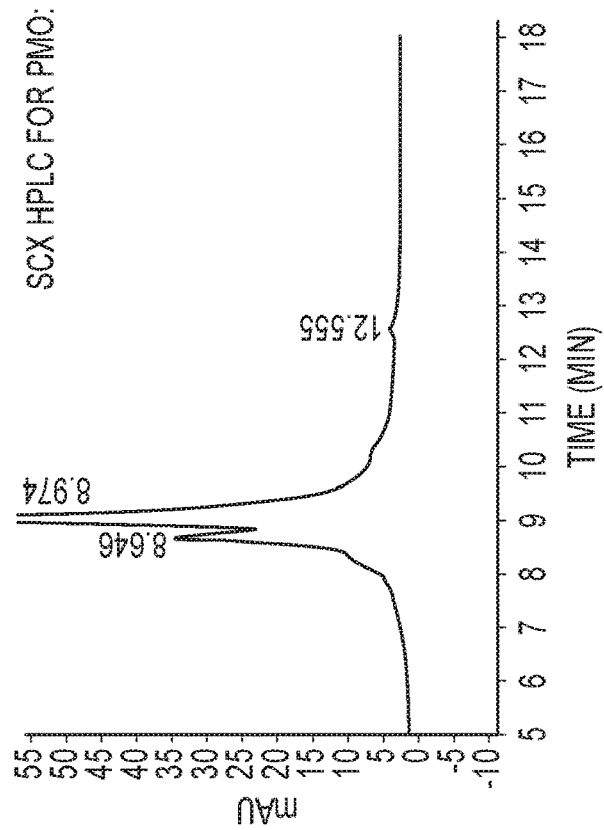
Figure 7A:
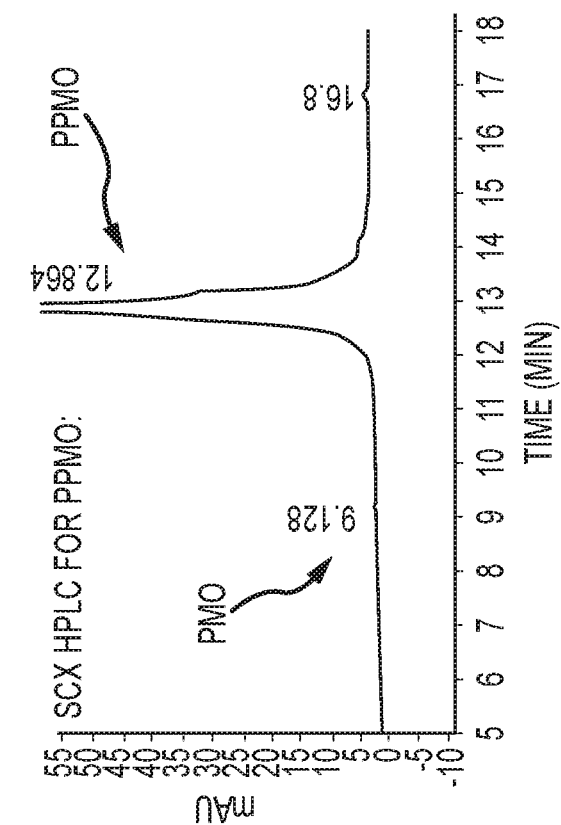
FIGS. 7A and 7B details SCX HPLC chromatograms (PMO and PPMO) for SEQ ID NO: 126. (A) details a chromatogram for SEQ ID NO: 126 PMO. (B) details a chromatogram for SEQ ID NO: 126 as a PPMO, showing unconjugated PMO, the expected main peak of conjugated PPMO, and, showing higher molecular weight aggregates with the SEQ ID NO: 126 PPMO.
Figure 7B:
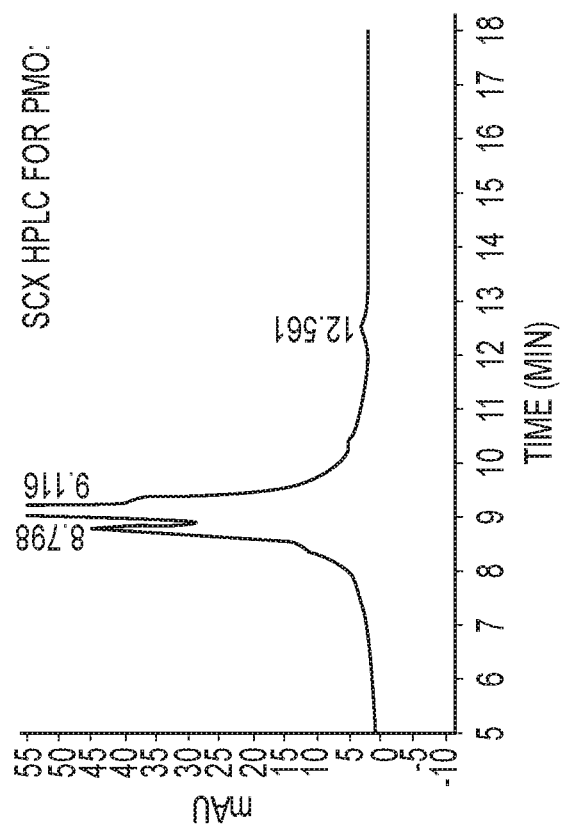

As shown in FIG. 6B, there is separation between the SEQ ID NO: 125 PMO peak (8.961 mAU) and the SEQ ID NO: 125 PPMO peak (12.683 mAU); however, higher molecular weight aggregates are present (see, peaks at 14.058, 14.867, 16.579, and 17.674 mAUs). This is in contrast to SEQ ID NO: 126 PPMO in which the higher molecular weight aggregates have been resolved (FIG. 7B). No higher molecular weight aggregates are present in either the SEQ ID NO: 125 PMO or the SEQ ID NO: 126 PMO (FIGS. 6A and 7A)

What is claimed is:

1. A modified antisense oligonucleotide, or a pharmaceutically acceptable salt thereof, of about 10 to about 40 nucleobases comprising a targeting sequence consisting of any one of SEQ ID NOs: 9-25.

2. The modified antisense oligonucleotide or pharmaceutically acceptable salt thereof of claim 1, wherein the modified antisense oligonucleotide is conjugated to a peptide.

3. The modified antisense oligonucleotide or pharmaceutically acceptable salt thereof of claim 1, wherein the modified antisense oligonucleotide enhances exon 7 inclusion in the processing of human SMN2 pre-processed mRNA.

4. A modified antisense oligonucleotide, or pharmaceutically acceptable salt thereof, of about 10 to about 40 nucleobases comprising a deletion sequence wherein the deletion sequence consists of at least one base sequence according to any one of SEQ ID NOs: 9-25.

5. The modified antisense oligonucleotide or pharmaceutically acceptable salt thereof of claim 4, wherein the modified antisense oligonucleotide enhances exon 7 inclusion in the processing of human SMN2 pre-processed mRNA.

6. A pharmaceutical composition, comprising a modified antisense oligonucleotide of claim 1, or a pharmaceutically acceptable salt thereof, and a pharmaceutically acceptable carrier.

7. A pharmaceutical composition, comprising a modified antisense oligomer of claim 4, or a pharmaceutically acceptable salt thereof, and a pharmaceutically acceptable carrier.

8. A method for treating spinal muscular atrophy in a patient in need thereof, comprising administering to the patient a modified antisense antisense oligonucleotide, or a pharmaceutically acceptable salt thereof, of claim 1.

9. A method for treating spinal muscular atrophy in a patient in need thereof, comprising administering to the patient a modified antisense antisense oligonucleotide, or a pharmaceutically acceptable salt thereof, of claim 4.

* * * * *

SEQUENCE LISTING

<160> NUMBER OF SEQ ID NOS: 129

<210> SEQ ID NO 1
<211> LENGTH: 25
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(25)
<223> OTHER INFORMATION: n is t or u

<400> SEQUENCE: 1
nncncaacag ancngncaaa ncgcc                                              25

<210> SEQ ID NO 2
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 2
nncncaacga ncngncaaan cgcc                                               24

<210> SEQ ID NO 3
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 3
nncncaacag ncngncaaan cgcc                                               24

<210> SEQ ID NO 4
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 4
nncncaacag acngncaaan cgcc                                               24

<210> SEQ ID NO 5
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 5

-continued

```
nncncaacaa ncngncaaan cgcc                                          24

<210> SEQ ID NO 6
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 6
nncncaacag ancgncaaan cgcc                                          24

<210> SEQ ID NO 7
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 7
nncncaacag anngncaaan cgcc                                          24

<210> SEQ ID NO 8
<211> LENGTH: 25
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(25)
<223> OTHER INFORMATION: n is t or u

<400> SEQUENCE: 8
gnaagannca cnnncanaan gcngg                                         25

<210> SEQ ID NO 9
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 9
gaaganncac nnncanaang cngg                                          24

<210> SEQ ID NO 10
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u
```

```
<400> SEQUENCE: 10
gnaganncac nnncanaang cngg                                          24

<210> SEQ ID NO 11
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 11
gnaaanncac nnncanaang cngg                                          24

<210> SEQ ID NO 12
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 12
gnaagnncac nnncanaang cngg                                          24

<210> SEQ ID NO 13
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 13
gnaagancac nnncanaang cngg                                          24

<210> SEQ ID NO 14
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 14
gnaagannac nnncanaang cngg                                          24

<210> SEQ ID NO 15
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u
```

```
<400> SEQUENCE: 15
gnaaganncc nnncanaang cngg                                              24

<210> SEQ ID NO 16
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 16
gnaagannca nnncanaang cngg                                              24

<210> SEQ ID NO 17
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 17
gnaagannca cnncanaang cngg                                              24

<210> SEQ ID NO 18
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 18
gnaagannca cnnnanaang cngg                                              24

<210> SEQ ID NO 19
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 19
gnaagannca cnnncnaang cngg                                              24

<210> SEQ ID NO 20
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
```

-continued

<223> OTHER INFORMATION: n is t or u

<400> SEQUENCE: 20
gnaagannca cnnncaaang cngg          24

<210> SEQ ID NO 21
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 21
gnaagannca cnnncanang cngg          24

<210> SEQ ID NO 22
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 22
gnaagannca cnnncanaag cngg          24

<210> SEQ ID NO 23
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 23
gnaagannca cnnncanaan cngg          24

<210> SEQ ID NO 24
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 24
gnaagannca cnnncanaan gngg          24

<210> SEQ ID NO 25
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature

```
<222> LOCATION: (1)..(24)
<223> OTHER INFORMATION: n is t or u

<400> SEQUENCE: 25
gnaagannca cnnncanaan gcgg                                              24

<210> SEQ ID NO 26
<211> LENGTH: 24
<212> TYPE: DNA
<213> ORGANISM: Artificial Sequence
<220> FEATURE:
<223> OTHER INFORMATION: deletion and/or targeting sequence

<400> SEQUENCE: 26
ggccagaagg aaggcgagaa aagc                                              24

<210> SEQ ID NO 27
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 27
gccagaagga aggcgagaaa agcn                                              24

<210> SEQ ID NO 28
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 28
ccagaaggaa ggcgagaaaa gcnc                                              24

<210> SEQ ID NO 29
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 29
cagaaggaag gcgagaaaag cncc                                              24

<210> SEQ ID NO 30
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u
```

```
<400> SEQUENCE: 30
agaaggaagg cgagaaaagc ncca                                              24

<210> SEQ ID NO 31
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 31
gaaggaaggc gagaaaagcn ccag                                              24

<210> SEQ ID NO 32
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 32
aaggaaggcg agaaaagcnc cagc                                              24

<210> SEQ ID NO 33
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 33
aggaaggcga gaaaagcncc agca                                              24

<210> SEQ ID NO 34
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u

<400> SEQUENCE: 34
cggcncncaa agcagcncng aga                                               23

<210> SEQ ID NO 35
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u
```

<400> SEQUENCE: 35
acggcncnca aagcagcncn gag                                               23

<210> SEQ ID NO 36
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u

<400> SEQUENCE: 36
cacggcncnc aaagcagcnc nga                                               23

<210> SEQ ID NO 37
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u

<400> SEQUENCE: 37
ncacggcncn caaagcagcn cng                                               23

<210> SEQ ID NO 38
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u

<400> SEQUENCE: 38
cncacggcnc ncaaagcagc ncn                                               23

<210> SEQ ID NO 39
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u

<400> SEQUENCE: 39
acncacggcn cncaaagcag cnc                                               23

<210> SEQ ID NO 40
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)

<223> OTHER INFORMATION: n is t or u

<400> SEQUENCE: 40
gcggcacnca cggcncncaa agc                                    23

<210> SEQ ID NO 41
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u

<400> SEQUENCE: 41
ggcggcacnc acggcncnca aag                                    23

<210> SEQ ID NO 42
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u

<400> SEQUENCE: 42
cggcacncac ggcncncaaa gca                                    23

<210> SEQ ID NO 43
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u

<400> SEQUENCE: 43
gcacncacgg cncncaaagc agc                                    23

<210> SEQ ID NO 44
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u

<400> SEQUENCE: 44
ggcacncacg gcncncaaag cag                                    23

<210> SEQ ID NO 45
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature

```
<222> LOCATION: (1)..(23)
<223> OTHER INFORMATION: n is t or u

<400> SEQUENCE: 45
cacncacggc ncncaaagca gcn                                            23

<210> SEQ ID NO 46
<211> LENGTH: 23
<212> TYPE: DNA
<213> ORGANISM: Artificial Sequence
<220> FEATURE:
<223> OTHER INFORMATION: deletion and/or targeting sequence

<400> SEQUENCE: 46
gccagaagga aggcgagaaa agc                                            23

<210> SEQ ID NO 47
<211> LENGTH: 22
<212> TYPE: DNA
<213> ORGANISM: Artificial Sequence
<220> FEATURE:
<223> OTHER INFORMATION: deletion and/or targeting sequence

<400> SEQUENCE: 47
ccagaaggaa ggcgagaaaa gc                                             22

<210> SEQ ID NO 48
<211> LENGTH: 21
<212> TYPE: DNA
<213> ORGANISM: Artificial Sequence
<220> FEATURE:
<223> OTHER INFORMATION: deletion and/or targeting sequence

<400> SEQUENCE: 48
cagaaggaag gcgagaaaag c                                              21

<210> SEQ ID NO 49
<211> LENGTH: 23
<212> TYPE: DNA
<213> ORGANISM: Artificial Sequence
<220> FEATURE:
<223> OTHER INFORMATION: deletion and/or targeting sequence

<400> SEQUENCE: 49
ggccagaagg aaggcgagaa aag                                            23

<210> SEQ ID NO 50
<211> LENGTH: 22
<212> TYPE: DNA
<213> ORGANISM: Artificial Sequence
<220> FEATURE:
<223> OTHER INFORMATION: deletion and/or targeting sequence

<400> SEQUENCE: 50
ggccagaagg aaggcgagaa aa                                             22

<210> SEQ ID NO 51
<211> LENGTH: 21
<212> TYPE: DNA
<213> ORGANISM: Artificial Sequence
<220> FEATURE:
<223> OTHER INFORMATION: deletion and/or targeting sequence

<400> SEQUENCE: 51
ggccagaagg aaggcgagaa a                                              21
```

```
<210> SEQ ID NO 52
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 52
nggggagagg gccagaagga aggc                                          24

<210> SEQ ID NO 53
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u

<400> SEQUENCE: 53
nggggagagg gccagaagga agc                                           23

<210> SEQ ID NO 54
<211> LENGTH: 22
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(22)
<223> OTHER INFORMATION: n is t or u

<400> SEQUENCE: 54
nggggagagg gccagaagga ac                                            22

<210> SEQ ID NO 55
<211> LENGTH: 23
<212> TYPE: DNA
<213> ORGANISM: Artificial Sequence
<220> FEATURE:
<223> OTHER INFORMATION: deletion and/or targeting sequence

<400> SEQUENCE: 55
ggccagaagg aagcgagaaa agc                                           23

<210> SEQ ID NO 56
<211> LENGTH: 22
<212> TYPE: DNA
<213> ORGANISM: Artificial Sequence
<220> FEATURE:
<223> OTHER INFORMATION: deletion and/or targeting sequence

<400> SEQUENCE: 56
ggccagaagg aacgagaaaa gc                                            22

<210> SEQ ID NO 57
<211> LENGTH: 23
<212> TYPE: DNA
<213> ORGANISM: Artificial Sequence
<220> FEATURE:
<223> OTHER INFORMATION: deletion and/or targeting sequence
```

```
<220> FEATURE:
<221> NAME/KEY: misc_feature
<222> LOCATION: (1)..(23)
<223> OTHER INFORMATION: n is t or u

<400> SEQUENCE: 57
aggaagcgag aaaagcncca gca                                              23

<210> SEQ ID NO 58
<211> LENGTH: 22
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(22)
<223> OTHER INFORMATION: n is t or u

<400> SEQUENCE: 58
aggaacgaga aaagcnccag ca                                               22

<210> SEQ ID NO 59
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 59
cgggcncnca aagcagcncn gaga                                             24

<210> SEQ ID NO 60
<211> LENGTH: 22
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(22)
<223> OTHER INFORMATION: n is t or u

<400> SEQUENCE: 60
cgcncncaaa gcagcncnga ga                                               22

<210> SEQ ID NO 61
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 61
ccncncaaag cagcncngag a                                                21

<210> SEQ ID NO 62
<211> LENGTH: 24
<212> TYPE: DNA
<213> ORGANISM: Artificial Sequence
<220> FEATURE:
```

```
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 62
ggcggcacnc acgggcncnc aaag                                              24

<210> SEQ ID NO 63
<211> LENGTH: 22
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(22)
<223> OTHER INFORMATION: n is t or u

<400> SEQUENCE: 63
ggcggcacnc acgcncncaa ag                                                22

<210> SEQ ID NO 64
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 64
ggcggcacnc accncncaaa g                                                 21

<210> SEQ ID NO 65
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 65
gcgggagggg cggcacncac gggc                                              24

<210> SEQ ID NO 66
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u

<400> SEQUENCE: 66
gcgggagggg cggcacncac ggc                                               23

<210> SEQ ID NO 67
<211> LENGTH: 22
<212> TYPE: DNA
<213> ORGANISM: Artificial Sequence
```

-continued

```
<220> FEATURE:
<223> OTHER INFORMATION: deletion and/or targeting sequence
<220> FEATURE:
<221> NAME/KEY: misc_feature
<222> LOCATION: (1)..(22)
<223> OTHER INFORMATION: n is t or u

<400> SEQUENCE: 67
gcgggagggg cggcacncac gc                                              22

<210> SEQ ID NO 68
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 68
gcgggagggg cggcacncac c                                               21

<210> SEQ ID NO 69
<211> LENGTH: 30
<212> TYPE: DNA
<213> ORGANISM: Artificial Sequence
<220> FEATURE:
<223> OTHER INFORMATION: Eteplirsen

<400> SEQUENCE: 69
ctccaacatc aaggaagatg gcatttctag                                      30

<210> SEQ ID NO 70
<211> LENGTH: 25
<212> TYPE: DNA
<213> ORGANISM: Artificial Sequence
<220> FEATURE:
<223> OTHER INFORMATION: Golodirsen

<400> SEQUENCE: 70
gttgcctccg gttctgaagg tgttc                                           25

<210> SEQ ID NO 71
<211> LENGTH: 22
<212> TYPE: DNA
<213> ORGANISM: Artificial Sequence
<220> FEATURE:
<223> OTHER INFORMATION: Casimersen

<400> SEQUENCE: 71
caatgccatc ctggagttcc tg                                              22

<210> SEQ ID NO 72
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 72
cccaacanca aggaagangg cannncnag                                       29
```

```
<210> SEQ ID NO 73
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 73
cncaacanca aggaagangg canncnag                                      29

<210> SEQ ID NO 74
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 74
cnccacanca aggaagangg canncnag                                      29

<210> SEQ ID NO 75
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 75
cnccaaanca aggaagangg canncnag                                      29

<210> SEQ ID NO 76
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 76
cnccaacnca aggaagangg canncnag                                      29

<210> SEQ ID NO 77
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 77
cnccaacaca aggaagangg canncnag                                      29
```

```
<210> SEQ ID NO 78
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 78
cnccaacana aggaagangg canncnag                                          29

<210> SEQ ID NO 79
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 79
cnccaacanc aggaagangg canncnag                                          29

<210> SEQ ID NO 80
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 80
cnccaacanc aagaagangg canncnag                                          29

<210> SEQ ID NO 81
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 81
cnccaacanc aaggagangg canncnag                                          29

<210> SEQ ID NO 82
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 82
```
cnccaacanc aaggaaangg cannncnag                                             29

<210> SEQ ID NO 83
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 83
cnccaacanc aaggaagngg cannncnag                                             29

<210> SEQ ID NO 84
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 84
cnccaacanc aaggaagagg cannncnag                                             29

<210> SEQ ID NO 85
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 85
cnccaacanc aaggaagang cannncnag                                             29

<210> SEQ ID NO 86
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 86
cnccaacanc aaggaagang gannncnag                                             29

<210> SEQ ID NO 87
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 87
cnccaacanc aaggaagang gcnnncnag                                29

<210> SEQ ID NO 88
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 88
cnccaacanc aaggaagang gcanncnag                                29

<210> SEQ ID NO 89
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 89
cnccaacanc aaggaagang gcannnnag                                29

<210> SEQ ID NO 90
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 90
cnccaacanc aaggaagang gcannncag                                29

<210> SEQ ID NO 91
<211> LENGTH: 29
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(29)
<223> OTHER INFORMATION: n is t or u

<400> SEQUENCE: 91
cnccaacanc aaggaagang gcannncng                                29

<210> SEQ ID NO 92
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

```
<400> SEQUENCE: 92
gngccnccgg nncngaaggn gnnc                                               24

<210> SEQ ID NO 93
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 93
gnnccnccgg nncngaaggn gnnc                                               24

<210> SEQ ID NO 94
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 94
gnngcnccgg nncngaaggn gnnc                                               24

<210> SEQ ID NO 95
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 95
gnngccccgg nncngaaggn gnnc                                               24

<210> SEQ ID NO 96
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 96
gnngccncgg nncngaaggn gnnc                                               24

<210> SEQ ID NO 97
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u
```

<400> SEQUENCE: 97
gnngccnccg nncngaaggn gnnc        24

<210> SEQ ID NO 98
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 98
gnngccnccg gncngaaggn gnnc        24

<210> SEQ ID NO 99
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 99
gnngccnccg gnnngaaggn gnnc        24

<210> SEQ ID NO 100
<211> LENGTH: 25
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(25)
<223> OTHER INFORMATION: n is t or u

<400> SEQUENCE: 100
gnngccnccg gnncgaaggn gtnnc       25

<210> SEQ ID NO 101
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 101
gnngccnccg gnncnaaggn gnnc        24

<210> SEQ ID NO 102
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)

<223> OTHER INFORMATION: n is t or u

<400> SEQUENCE: 102
gnngccnccg gnncngaggn gnnc					24

<210> SEQ ID NO 103
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 103
gnngccnccg gnncngaagn gnnc					24

<210> SEQ ID NO 104
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 104
gnngccnccg gnncngaagg gnnc					24

<210> SEQ ID NO 105
<211> LENGTH: 24
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(24)
<223> OTHER INFORMATION: n is t or u

<400> SEQUENCE: 105
gnngccnccg gnncngaagg nnnc					24

<210> SEQ ID NO 106
<211> LENGTH: 23
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u

<400> SEQUENCE: 106
gnngccnccg gncngaaggn gnc					23

<210> SEQ ID NO 107
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature

```
<222> LOCATION: (1)..(21)
<223> OTHER INFORMATION: n is t or u

<400> SEQUENCE: 107
cangccancc nggagnnccn g                                          21

<210> SEQ ID NO 108
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 108
caagccancc nggagnnccn g                                          21

<210> SEQ ID NO 109
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 109
caanccancc nggagnnccn g                                          21

<210> SEQ ID NO 110
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 110
caangcancc nggagnnccn g                                          21

<210> SEQ ID NO 111
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 111
caangccncc nggagnnccn g                                          21

<210> SEQ ID NO 112
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
```

<221> NAME/KEY: misc_feature
<222> LOCATION: (1)..(21)
<223> OTHER INFORMATION: n is t or u

<400> SEQUENCE: 112
caangccacc nggagnnccn g                                              21

<210> SEQ ID NO 113
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 113
caangccanc nggagnnccn g                                              21

<210> SEQ ID NO 114
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 114
caangccanc cggagnnccn g                                              21

<210> SEQ ID NO 115
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 115
caangccanc cngagnnccn g                                              21

<210> SEQ ID NO 116
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 116
caangccanc cngggnnccn g                                              21

<210> SEQ ID NO 117
<211> LENGTH: 21
<212> TYPE: DNA
<213> ORGANISM: Artificial Sequence
<220> FEATURE:
<223> OTHER INFORMATION: deletion and/or targeting sequence

```
<220> FEATURE:
<221> NAME/KEY: misc_feature
<222> LOCATION: (1)..(21)
<223> OTHER INFORMATION: n is t or u

<400> SEQUENCE: 117
caangccanc cnggannccn g                                              21

<210> SEQ ID NO 118
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 118
caangccanc cnggagnccn g                                              21

<210> SEQ ID NO 119
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 119
caangccanc cnggagnncn g                                              21

<210> SEQ ID NO 120
<211> LENGTH: 21
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(21)
<223> OTHER INFORMATION: n is t or u

<400> SEQUENCE: 120
caangccanc cnggagnncc g                                              21

<210> SEQ ID NO 121
<211> LENGTH: 25
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(25)
<223> OTHER INFORMATION: n is t or u

<400> SEQUENCE: 121
ggcggcacnc acggggcncn caaag                                          25

<210> SEQ ID NO 122
<211> LENGTH: 23
<212> TYPE: DNA
<213> ORGANISM: Artificial Sequence
<220> FEATURE:
```

```
<223> OTHER INFORMATION: deletion and/or targeting sequence
<220> FEATURE:
<221> NAME/KEY: misc_feature
<222> LOCATION: (1)..(23)
<223> OTHER INFORMATION: n is t or u

<400> SEQUENCE: 122
ggcggcacnc acggcncnca aag                                            23

<210> SEQ ID NO 123
<211> LENGTH: 25
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(25)
<223> OTHER INFORMATION: n is t or u

<400> SEQUENCE: 123
cggggcncnc aaagcagcnc ngaga                                          25

<210> SEQ ID NO 124
<211> LENGTH: 25
<212> TYPE: DNA
<213> ORGANISM: Artificial Sequence
<220> FEATURE:
<223> OTHER INFORMATION: deletion and/or targeting sequence
<220> FEATURE:
<221> NAME/KEY: misc_feature
<222> LOCATION: (1)..(25)
<223> OTHER INFORMATION: n is t or u

<400> SEQUENCE: 124 ngggagagg gccagaagga agggc                                           25

<210> SEQ ID NO 125
<211> LENGTH: 25
<212> TYPE: DNA
<213> ORGANISM: Artificial Sequence
<220> FEATURE:
<223> OTHER INFORMATION: deletion and/or targeting sequence

<400> SEQUENCE: 125
ggccagaagg aagggcgaga aaagc                                          25

<210> SEQ ID NO 126
<211> LENGTH: 24
<212> TYPE: DNA
<213> ORGANISM: Artificial Sequence
<220> FEATURE:
<223> OTHER INFORMATION: deletion and/or targeting sequence

<400> SEQUENCE: 126
ggccagaagg aaggcgagaa aagc                                           24

<210> SEQ ID NO 127
<211> LENGTH: 23
<212> TYPE: DNA
<213> ORGANISM: Artificial Sequence
<220> FEATURE:
<223> OTHER INFORMATION: deletion and/or targeting sequence

<400> SEQUENCE: 127
ggccagaagg aagcgagaaa agc                                            23
```

```
<210> SEQ ID NO 128
<211> LENGTH: 22
<212> TYPE: DNA
<213> ORGANISM: Artificial Sequence
<220> FEATURE:
<223> OTHER INFORMATION: deletion and/or targeting sequence

<400> SEQUENCE: 128
ggccagaagg aacgagaaaa gc                                              22

<210> SEQ ID NO 129
<211> LENGTH: 40
<212> TYPE: RNA
<213> ORGANISM: Artificial Sequence
<220> FEATURE:
<223> OTHER INFORMATION: target sequence

<400> SEQUENCE: 129
guaagucugc cagcauuaug aaagugaauc uuacuuuugu                           40
```